(12) United States Patent
Umeda et al.

(10) Patent No.: US 7,910,593 B2
(45) Date of Patent: Mar. 22, 2011

(54) WATER-SOLUBLE PRODRUGS

(75) Inventors: Isao Umeda, Yokohama (JP); Jun Ohwada, Kamakura (JP); Sawako Ozawa, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 982 days.

(21) Appl. No.: 11/547,036

(22) PCT Filed: Apr. 8, 2005

(86) PCT No.: PCT/JP2005/006957
§ 371 (c)(1), (2), (4) Date: Dec. 18, 2006

(87) PCT Pub. No.: WO2005/097803
PCT Pub. Date: Oct. 20, 2005

(65) Prior Publication Data
US 2008/0015157 A1    Jan. 17, 2008

(30) Foreign Application Priority Data

Apr. 9, 2004   (JP) .................. 2004-115713

(51) Int. Cl.
| | |
|---|---|
| C07D 471/04 | (2006.01) |
| C07D 471/22 | (2006.01) |
| C07D 487/04 | (2006.01) |
| C07D 487/00 | (2006.01) |
| C07D 471/00 | (2006.01) |
| C07D 239/00 | (2006.01) |
| C07D 239/70 | (2006.01) |
| C07D 519/04 | (2006.01) |
| A01N 43/42 | (2006.01) |
| A61K 31/44 | (2006.01) |

(52) U.S. Cl. ........... 514/257; 544/245; 546/51; 514/283
(58) Field of Classification Search .................. 514/283, 514/257; 544/245; 546/51
See application file for complete search history.

(56) References Cited

U.S. PATENT DOCUMENTS

| | | | |
|---|---|---|---|
| 4,943,579 A | 7/1990 | Vishnuvajjala et al. | |
| 4,975,278 A | 12/1990 | Senter et al. | |
| 6,130,039 A | 10/2000 | Bandman et al. | |
| 6,245,750 B1 | 6/2001 | Shepard | |
| 6,265,540 B1 | 7/2001 | Isaacs et al. | |
| 6,294,344 B1 | 9/2001 | O'Brien | |
| 6,825,194 B2 | 11/2004 | Murata et al. | |
| 7,109,195 B2 | 9/2006 | Murata et al. | |
| 7,595,400 B2 | 9/2009 | Fukuda et al. | |
| 2001/0016329 A1 | 8/2001 | Shepard | |
| 2002/0012663 A1 | 1/2002 | Waksal | |
| 2003/0138864 A1* | 7/2003 | Ishitsuka et al. ............. | 435/7.23 |
| 2009/0118271 A1* | 5/2009 | Umeda et al. ............. | 514/232.8 |
| 2009/0149478 A1 | 6/2009 | Endo et al. | |
| 2009/0312554 A1 | 12/2009 | Fukuda et al. | |
| 2009/0326225 A1 | 12/2009 | Fukuda et al. | |

FOREIGN PATENT DOCUMENTS

| | | |
|---|---|---|
| AU | 199853264 B2 | 7/1998 |
| CN | 1241192 A | 1/2000 |
| CN | 1361700 A | 7/2002 |
| CN | 1424912 A | 6/2003 |
| EP | 0 074 256 B1 | 3/1983 |
| EP | 0 220 601 B1 | 5/1987 |
| EP | 0 296 597 B1 | 12/1988 |
| EP | 0 471 358 B1 | 2/1992 |
| EP | 0 495 432 B1 | 7/1992 |
| EP | 0 506 478 B1 | 9/1992 |
| EP | 0 667 165 A1 | 8/1995 |
| EP | 0 897 924 B1 | 2/1999 |
| EP | 1 757 609 A1 | 2/2007 |
| EP | 1 854 792 A1 | 11/2007 |
| GB | 2 334 256 A | 8/1999 |
| JP | 2-71836 A | 3/1990 |
| JP | 06-087746 A | 3/1994 |
| JP | 9-241298 A | 9/1997 |
| JP | 11-158080 A | 6/1999 |
| JP | 2002-505672 A | 2/2002 |
| JP | 2002-114710 A | 4/2002 |
| JP | 2003-520195 A | 7/2003 |
| JP | 2003-523980 A | 8/2003 |
| JP | 2004-535363 A | 11/2004 |

(Continued)

OTHER PUBLICATIONS

Smith, M. B. Organic Synthesis, McGraw-Hill, Inc. 1994, Chapter 1.*
Del Poeta, et al., Comparison of In Vitro Activities of Camptothecin and Nitidine Derivatives against Fungal and Cancer Cells, Antimicrobial Agents and Chemotherapy, pp. 2862-2868, vol. 43, No. 12 (1999).*
Shan et al., "Prodrug Strategies Based on Intramolecular Cyclization Reactions," Journal of Pharmaceutical Sciences, Jul. 1997, 86(7), 765-767.

(Continued)

Primary Examiner — James O Wilson
Assistant Examiner — Erich A Leeser
(74) Attorney, Agent, or Firm — Foley & Lardner LLP

(57) ABSTRACT

An objective of the present invention is to provide water-soluble prodrugs that can be administered parenterally, and which show excellent water solubility and small interspecies or individual differences and are rapidly converted to the active form by chemical conversion. This invention provides water-soluble prodrugs represented by formula (1), or pharmaceutically acceptable salts, or hydrates or solvates thereof,

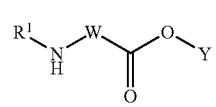

(1)

(wherein,
$R^1$ represents a hydrogen atom, or C1-C6 alkyl group;
W represents a divalent group comprising a tertiary amino group or sulfonyl group; and
Y represents a residue of a compound represented by Y—OH comprising an alcoholic hydroxyl group).

20 Claims, 4 Drawing Sheets

FOREIGN PATENT DOCUMENTS

| | | |
|---|---|---|
| JP | 2005-047934 A | 2/2005 |
| JP | 2005-511643 A | 4/2005 |
| JP | 2005-514359 A | 5/2005 |
| JP | 2005-255643 A | 9/2005 |
| WO | WO 90/03169 A1 | 4/1990 |
| WO | WO 95/22549 A1 | 8/1995 |
| WO | WO 96/38146 A1 | 12/1996 |
| WO | WO 98/13059 A1 | 4/1998 |
| WO | WO 98/28304 A1 | 7/1998 |
| WO | WO 98/35940 A1 | 8/1998 |
| WO | WO 98/51787 A2 | 11/1998 |
| WO | WO 98/56807 A1 | 12/1998 |
| WO | WO 98/57662 A2 | 12/1998 |
| WO | WO 99/05103 A2 | 2/1999 |
| WO | WO 00/51991 A1 | 9/2000 |
| WO | WO 00/63418 A1 | 10/2000 |
| WO | WO 01/20331 A1 | 3/2001 |
| WO | WO 01/49291 A1 | 7/2001 |
| WO | WO 01/62235 A2 | 8/2001 |
| WO | WO 02/00168 A2 | 1/2002 |
| WO | WO 02/10741 A2 | 2/2002 |
| WO | WO 02/056885 A1 | 7/2002 |
| WO | WO 02/070658 A2 | 9/2002 |
| WO | WO 02/100172 A1 | 12/2002 |
| WO | WO 03/043631 A2 | 5/2003 |
| WO | WO 03/045942 A2 | 6/2003 |
| WO | WO 03/045952 A2 | 6/2003 |
| WO | WO 2004/012662 A2 | 2/2004 |
| WO | WO 2004/014386 A1 | 2/2004 |
| WO | WO 2004/073601 A2 | 9/2004 |
| WO | WO 2005/097803 A1 | 10/2005 |
| WO | WO 2006/028904 A1 | 3/2006 |
| WO | WO 2006/090743 A1 | 8/2006 |

OTHER PUBLICATIONS

Albin et al., "Main Drug-metabolizing Enzyme Systems in Human Breast Tumors and Peritumoral Tissues," Cancer Research, vol. 53, Aug. 1, 1993, pp. 3541-3546.

Alevizos et al., "Oral cancer in vivo gene expression profiling assisted by laser capture microdissection and microarray analysis," Oncogene, vol. 20, Sep. 2001, pp. 6196-6204.

Batetta et al., "G6PD activity and gene expression in leukemic cells from G6PD-deficient subjects," Cancer Letters, vol. 140, Jun. 1999, pp. 53-58.

Beall et al., "Mechanisms of action of quinone-containing alkylating agents I: NQ01-directed drug development," Frontiers in Bioscience, vol. 5, Jul. 1, 2000, pp. 639-648.

Bielawska et al., "Prolidase as a prodrug converting enzyme II. Synthesis of praline analogue of anthraquinone-2-carboxylic acid and its susceptibility to the action of prolidase," Rocz. Akad. Med. Bialymst., vol. 43, 1998, pp. 201-209.

Bielawska et al., "Prodilase as a prodrug converting enzyme III. Synthesis of praline analogues of melphalan and their susceptibility to the action of prolidase," Rocz. Akad. Med. Bialymst., vol. 44, 1999, pp. 190-199.

Bielawska et al., "Prolidase-activated prodrug for cancer chemotherapy Cytotoxic activity of proline analogue of chlorambucil in breast cancer MCF-7 cells," II Farmaco, vol. 55, Nov.-Dec. 2000, pp. 736-741.

Bielawska et al., "Cytotoxicity activity of L-proline analogues of anthraquinone-2-carboxylic acid in breast cancer MCF-7 cells," Folia Histochemica et Cytobiologica, vol. 39, suppl. 2, May 2001, pp. 207-208.

Ciaccio et al., "Modulation of Detoxification Gene Expression in Human Colon HT29 Cells by Glutathione-S-Transferase Inhibitors," Mol. Pharamcol., vol. 48, No. 4, Oct. 1995, pp. 639-647.

Gasa et al., "Elevated Activities and Properties of Arylsulfatases A and B and B-Variant in Human Lung Tumors," Cancer Research, vol. 40, No. 10, Oct. 1980, pp. 3804-3809.

Greengard et al., "The Undifferentiated Enzymic Composition of Human Fetal Lung and Pulmonary Tumors," Cancer Research, vol. 3, Mar. 1977, pp. 884-891.

Herzfeld et al., "Human Colon Tumors," Cancer, vol. 42, No. 3, Sep. 1978, pp. 1280-1283.

Herzfeld et al., "Enzyme Activities in Human Fetal and Neoplastic Tissues," Cancer, vol. 46, No. 9, Nov. 1980, pp. 2047-2054.

Hsu et al., "Overexpression of dihydrodiol Dehydrogenase as a Prognostic Marker of Non-Small Cell Lung Cancer," Cancer Research, vol. 6, Mar. 15, 2001, pp. 2727-2731.

Kapitonov et al., "Cloning, Characterization, and Expression of Human Ceramide Galactosyltransferase cDNA," Biochemical and Biophysical Research Communications, vol. 232, Mar. 1997, pp. 449-453.

Karna et al., "Collagen metabolism disturbances are accompanied by an increase in prolidase activity in lung carcinoma planoepitheliale," Int. J. Exp. Path., vol. 81, No. 5, Oct. 2000, pp. 341-347.

Kashima et al., "Expression of Oligodendrocyte-associated Genes in Cell Lines Derived from Human Gliomas and Neuroblastomas," Cancer Research, vol. 53, Jan. 1, 1993, pp. 170-175.

Kirschmann et al., "Differentially expressed genes associated with the metastatic phenotype in breast cancer," Breast Cancer Research and Treatment, vol. 55, No. 2, May 1999, pp. 127-136.

Krovat et al., "Fingerprinting of cytochrome P450 and Microsomal Epoxide Hydrolase Gene Expression in Human Blood Cells," Toxicological Sciences, vol. 55, No. 2, Jun. 2000, pp. 352-360.

Kuivaniemi et al., "Deficient production of lysyl oxidase in cultures of malignantly transformed human cells," FEBS Lett, vol. 195, No. 1-2, Jan. 1986, pp. 261-264.

Kuo et al., "Human glucose-6-phosphate dehydrogenase (G6PD) gene transforms NIH 3T3 cells and induces tumors in nude mice," Int. J. Cancer, vol. 85, No. 6, Mar. 2000, pp. 857-864.

Leenders et al., "Synthesis and evaluation of novel duanomycin-phosphate-sulfate-β-glucuronide and -β-glucoside prodrugs for application in adept," Bioorganic & Medical Chemistry Letters, vol. 5, No. 24, Dec. 21, 1995, pp. 2975-2980.

Li et al., "Partial characterization of a cDNA for human stearoyl-CoA desaturase and changes in its mRNA expression in some normal and malignant tissues," Int. J. Cancer, vol. 57, No. 3, May 1, 1994, pp. 348-352.

Lin et al., "Role of Pharmacokinetics and Metabolism in Drug Discovery and Development," Pharmacological Reviews, vol. 49, No. 4, Dec. 1997, pp. 403-449.

Liu et al., "Identification of Differentially Expressed Prostate Genes: Increased Expression of Transcription Factor ETS-2 in Prostate Cancer," Prostate, vol. 30, No. 3, Feb. 15, 1997, pp. 145-153.

Lopaczynska et al., "Upregulation of pyrroline-5-carboxylate reductase in benzo(a)pyrene resistant human tumor cells (MCF-7): a redox-dependent mechanism for resistance to benzo(a)pyrene," Proc. Of the Annual Meeting of the American Assoc. for Cancer Research, vol. 36, No. 122, Mar. 1995, #724.

Lopez De Cerain et al., "Carbonyl Reductase and NADPH Cytochrome P450 Reductase Activities in Human Tumoral Versus Normal Tissues," Eur. J. Cancer, vol. 35, No. 2, Feb. 1999, pp. 320-324.

Lou et al., "Genomic Organization and Chromosomal Localization of a Novel Human Hepatic Dihydrodiol Dehydrogenase with High Affinity Bile Acid Binding," J. Biol. Chem.., vol. 269, No. 11, Mar. 18, 1994, pp. 8416-8422.

Lu et al., "Gene Expression Changes Associated with Chemically Induced Rat Mammary Carcinogenesis," Molecular Carcinogenesis, vol. 20, No. 2, Oct. 1997, pp. 204-215.

Maeda et al., "Automated determination of 5-fluorouracil and its metabolite in urine by high-performance liquid chromatorgraphy with column switching," J. Chromatogr. B, vol. 731, No. 2, Aug. 1999, pp. 267-273.

Myllyla et al., "Regulation of collagen post-translational modification in transformed human and chick-embryo cells," Biochem. J., vol. 196, No. 3, Jun. 15, 1981, pp. 683-692.

Naguib et al., "Enzymes of Uracil Catabolism in Normal and Neoplastic Human Tissues," Cancer Research, vol. 45, No. 11.1, Nov. 1, 1985, pp. 5405-5412.

Page et al., "Proteomic definition of normal human luminal and myoepithelial breast cells purified from reduction mammoplasties," Proc. Natl. Acad. Sci. USA, vol. 96, No. 22, Oct. 26, 1999, pp. 12589-12594.

Paterson et al., "Regulation of Glutamine: Fructose-6-Phosphate Amidotransferase Gene Trascription by Epidermal Growth Factor and Glucose," Endocrinology, vol. 136, No. 7, Jul. 1995, pp. 2809-2816.

Pihlajaniemi et al., "Effects of Strptozotocin Diabetes, Glucose, and Insulin on the Metabolism of Type IV Collagen and Proteoglycan in Murine Basement Membrane-forming EHS Tumor Tissue," J. Biol. Chem., vol. 257, No. 24, Dec. 25, 1982, vol. 14914-14920.

Polak et al., "Localization of Bombesin-like Peptides in Tumors," Ann. N.Y. Acad. Sci., vol. 547, 1988, pp. 322-335.

Rihn et al., "Differential gene expression in mesothelioma," FEBS Lett., vol. 480, No. 2-3, Sep. 1, 2000, pp. 95-100.

Shin et al., "Spatial and temporal expression of UDP-galactose: ceramide galactosyl transferase mRNA during rat brain development," Anat. Embryol., vol. 200, No. 2, Aug. 1999, pp. 193-201.

Skala et al., "Molecular cloning and expression of rat aldolase C messenger RNA during development and hepatocarcinogenesis," Eur. J. Biochem., vol. 163, No. 3, Mar. 16, 1987, pp. 513-518.

Wang et al., "Monitoring gene expression profile changes in ovarian carcinomas using cDNA microarray," vol. 229, No. 1-2, Mar. 18, 1999, pp. 101-108.

Yamamoto et al., "Screening and Production of Arylsulfatases for Target Therapy with Etoposide 4'-sulfate, an Antitumor Prodrug," Biosci. Biotech. Biochem., vol. 59, No. 6, Jun. 1995, pp. 1057-1061.

Yu et al., "The correlation of membranous glycoprotein-GP-170, cytoplasmic glutathione and glucose-6-phosphate dehydrogenase levels with multidrug resistance in transitional cell carcinoma cell lines of the urinary tract," J. Urol., vol. 157, No. 2, Feb. 1997, pp. 727-731.

Van Der Slot et al., "Elevated formation of pyridinoline cross-links by profibrotic cytokines is associated with enhanced lysyl hydroxylase 2b levels," Biochim. Biophys. Acta., vol. 1741, No. 1-2, Jun. 30, 2005, pp. 95-102.

Buckhaults et al., "Secreted and Cell Surface Genes Expressed in Benign and Malignant Colorectal Tumors," Cancer Research, Oct. 1, 2001, 61:6996-7001.

Zhang et al., "Mechanism of Enolase: The Crystal Structure of Assymmetric Dimer Enolase—2-Phospho-D-glycerate/Enolase—Phosophoenolpyruvate at 2.0 A Resolution," Biochemistry, 1997, 36:12526-12534.

Hooper et al., "Renal Dipeptidase is One of the membrane Proteins Released by Phosphatidylinositol-Specific Phospholipase C," Biochemistry Journal, 1987, 244:465-469.

El-Rifai et al., "Expression Profiling of Gastric Adenocarcinoma Using cDNA Array," Int. J. Cancer, Apr. 2, 2001, 93:832-838.

Defeo-Jones et al., "A Peptide-Doxorubicin 'Prodrug' Activated by Prostate-Specific Antigen Selectively Kills Prostate Tumor Cells Positive for Prostate-Specific Antigen In Vivo," Nature medicine, Nov. 2000, 11(11):1248-1252.

Okabe et al., "Genome-Wide Analysis of Gene Expression in Human Hepatocellular Carcinomas Using cDNA Microarray: Identification of Genes Involved in Viral Carcinogenesis and Tumor Progression," Cancer Research, Mar. 1, 2001, 61:2129-2137.

Welsh et al., "Analysis of Gene Expression Identifies Candidate Markers and Pharmacological Targets in Prostate Cancer," Cancer Research, Aug. 15, 2001, 61:5974-5978.

Zhou et al., "The Pattern of Gene Expression in Human CD34+ Stem/Progenitor Cells," PNAS, Nov. 20, 2001, 98(24):13966-13971.

Schena et al., Science, 1995, 270:467-470.

Miwa et al., Eur. J. Cancer, 1998, 34:1274-1281.

Ross et al., Nature Genetics, Mar. 2000, 24:227-235.

Lam et al., The Journal of Biological Chemistry, 2000, 272:19676-19684.

Greengard et al., "The Undifferentiated Enzymic Composition of Human Fetal Lung and Pulmonary Tumors," Cancer Research, vol. 37, No. 3, Mar. 1977, pp. 884-891.

Hsu et al., "Overexpression of dihydrodiol Dehydrogenase as a Prognostic Marker of Non-Small Cell Lung Cancer," Cancer Research, vol. 61, No. 6, Mar. 15, 2001, pp. 2727-2731.

Defeo-Jones et al., "A Peptide-Doxorubicin 'Prodrug' Activated by Prostate-Specific Antigen Selectively Kills Prostate Tumor Cells Positive for Prostate-Specific Antigen In Vivo," Nature medicine, Nov. 2000, vol. 6, No. 11:1248-1252.

Lam et al., The Journal of Biological Chemistry, 2000, vol. 275, No. 26:19676-19684.

Connors et al., "Prodrugs in Cancer Chemotherapy," Stem Cells, Sep. 1995, 13(5):501-511.

Eng et al., "Biological agents versus chemotherapy in the treatment of colorectal cancer," Expert Opin. Pharmacother., Jul. 2006, 7(10):1251-1271.

Englebretsen et al., "An N-Terminal Method for Peptide Solubilisation," Tetrahedron, May 21, 1999, 55(21):6623-6634.

Kawahara, Masaaki, "Irinotecan in the treatment of small cell lung cancer: a review of patient safety considerations," Expert Opin. Drug Saf., Mar. 2006, 5(2):303-312.

Kulke, Matthew H., "Advanced pancreatic cancer: is there a role for combination therapy?", Expert Rev. Anticancer Ther., Oct. 2003, 3(5):729-739.

Narahara et al., "Multi-agent combination chemotherapy comprising CPT-11," Jpn. J. Cancer Chemother., Nov. 2004, 31(12):1973-1977, and English translation, 10 pages.

Santos et al., "Cyclization-activated prodrugs. Synthesis, reactivity and toxicity of dipeptide esters of paracetamol," Bioorganic & Medicinal Chemistry Letters, Mar. 15, 2005, 15(6):1595-1598.

Sasaki, Igaku no Ayumi, Jan. 31, 1998, 184(5):375-379.

Sato et al., "Positioning of combination chemotherapy for advanced gastric cancer," Igaku no Ayumi, Jan. 31, 1998, 184(5):347-351, and English translation, 9 pages.

Wöhrer et al., "Palliative chemotherapy for advanced gastric cancer," Annals of Oncology, Nov. 2004, 15(11):1585-1595.

Chemical Encyclopedic Dictionary, K.L. Knuniants Editor, 1983, 130-131, with English translation, 4 pages.

The Global Bioresource Center, Product Description, Cell Biology, ATCC No. CCL-247, 4 pages (no date, accessed online Jan. 21, 2010).

Office Action dated Apr. 23, 2010, in Chinese Application CN20068039397, 7 pages.

Supplementary European Search Report dated Aug. 4, 2010, in EP 05728811.0, 3 pages.

Bedeschi et al., "Synthesis and Antitumor Activity of a New Class of Water Soluble Camptothecin Derivatives," Bioorganic Med. Chem. Lett., 1996, 6(6):671-674.

Gelderblom et al., "Oral Topoisomerase 1 inhibitors in adult patients: present and future," Invest. New Drugs, 1999, 17:401-415.

Gerrits et al., "Topoisomerase 1 inhibitors: the relevance of prolonged exposure for present clinical development," British J. of Cancer, 1997, 76(7):952-962.

Hatefi et al., "Camptothecin Delivery Methods," Pharm. Res., 2002, 19(10):1389-1399.

Kehrer et al., "Modulation of camptothecin analogs in the treatment of cancer: a review," Anti-Cancer Drugs, 2001, 12:89-105.

Kingsbury et al., "Synthesis of Water-Soluble (aminoalkyl)camptothecin Analogues: Inhibition of Topoisomerase I and Antitumor Activity," J. Med. Chem., 1991, 34:98-107.

Kunimoto et al., "Antitumor Activity of 7-Ethyl-10-[4-(1-piperidino)-1-piperidino]carbonyloxy-camptothecin, a Novel Water-soluble Derivative of Camptothecin, against Murine Tumors," Cancer Research, Nov. 15, 1987, 47: 5944-5947.

O'Leary et al., "Camptothecins: A Review of their Development and Schedules of Administration," Eur. J. of Cancer, 1998, 34(10):1500-1508.

Simone, Joseph V., Oncology, Introduction, Cecil Textbook of Medicine, 20th Edition, vol. 1, 1996, pp. 1004-1010.

Sugimori et al., "Antitumor Agents. VI. Synthesis and Antitumor Activity of Ring A-, Ring B- and Ring C-Modified Derivatives of Camptothecin," Heterocycles, 1994, 38(1):81-94.

Sugimori et al., "Synthesis and Antitumor Activity of Ring A- and F-Modified Hexacyclic Camptothecin Analogues," J. Med. Chem., 1998, 41(13):2308-2318.

Sugimori et al., "Antitumor Agents. 7. Synthsis and Antitumor Activity of Novel Hexacyclic Camptothecin Analogues," J. Med. Chem., 1994, 37(19):3033-3039.

Vey et al., "The Topoisomerase I Inhibitor DX-8951f is Active in a Severe Combined Immunodeficient Mouse Model of Human Acute Myelogenous Leukemia," Clin. Cancer Res., Feb. 2000, 6:731-736.

Wall et al., "Plant Antitumor Agents. I. The Isolation and Structure of Camptothecin, a Novel Alkaloidal Leukemia and Tumor Inhibitor from *Camptotheca acuminate*," J. Am. Chem. Soc., 1966, 88(16):3888-3890.

Wani et al., "Plant Antitumor Agents. 23. Synthesis and Antileukemic Activity of Camptothecin Analogues," J. Med. Chem., 1986, 29:2358-2363.

Zunino et al., "Camptothecins in clinical development," Expert Opin. Investig. Drugs, 2004, 13(3):269-284.

Notice of Allowance in U.S. Appl. No. 10/546,287 (now US 7,595,400).

Non-Final Office Action mailed May 5, 2010, in U.S. Appl. No. 12/083,831.

* cited by examiner

WATER-SOLUBLE PRODRUGS

This application is a National Stage application of PCT/JP2005/006957, filed Apr. 8, 2005, which claims priority from Japenese patent application JP 2004-115713, filed Apr. 9, 2004. The entire contents of each of the aforementioned applications are incorporated herein by reference.

TECHNICAL FIELD

The present invention relates to novel water-soluble prodrugs, or pharmaceutically acceptable salts, or hydrates or solvates thereof. The present invention also relates to pharmaceutical compositions that comprise these substances, or liquid formulations that comprise these substances in aqueous solutions.

BACKGROUND ART

Camptothecins, taxanes, anticancer nucleotides and such are active against a wide variety of tumor cells, and thus are expected to be useful as therapeutic agents, such as anticancer agents (Patent Documents 1 and 2). Many of these compounds are lipophilic, and because of their low water solubility, their use in injections (parenteral administration) is sometimes limited (Patent Document 1).

Water-soluble prodrugs have been studied in an attempt to solubilize such lipophilic pharmaceutical agents in water (Non-Patent document 1 and Patent Document 1).
[Patent Document 1] WO03/043631
[Patent Document 2] WO03/045952
[Non-Patent Document 1] Shan et al., J. Pharm. Sci., 86(7), 765-767, 1997

DISCLOSURE OF THE INVENTION

Problems to Be Solved by the Invention

Most water-soluble prodrugs of lipophilic pharmaceutical agents are converted into their active form after administration, mainly by enzymes. However, this conversion occurs after a certain period of time following administration and varies among species and individuals, and thus has been an obstacle to the development of these prodrugs. Therefore, there was a high demand to develop water-soluble prodrugs that can be administered parenterally, which do not depend on enzymatic conversion and show small interspecies or individual differences.

Furthermore, in some cases, the rate and efficiency in converting a prodrug to its active form in blood was insufficient, and therefore, there was a need to shorten the time taken for the blood concentration of pharmaceutical agents to increase.

More specifically, an objective of the present invention is to provide water-soluble prodrugs that can be administered parenterally, and whose conversion into the active form does not depend on enzymes or show small interspecies or individual differences, and has an excellent rate and efficiency of conversion.

Means to Solve the Problems

Upon extensive studies to solve the above-mentioned objective, the present inventors discovered that prodrug compounds comprising solubilizing side chains with particular structures show excellent water-solubility, and that their interspecies or individual differences are small because of the rapid chemical conversion to the active form. Thus, the present invention was completed. The present invention is particularly useful for application to water-insoluble pharmaceutical agents such as camptothecin, which comprise a secondary alcoholic hydroxyl group or a tertiary alcoholic hydroxyl group.

More specifically, the present invention comprises the following embodiments:

1. A water-soluble prodrug represented by formula (1), or a pharmaceutically acceptable salt, or a hydrate or solvate thereof,

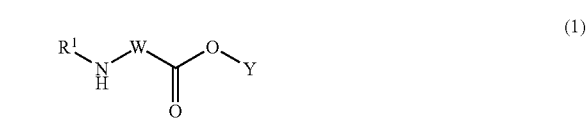

(wherein,
$R^1$ represents a hydrogen atom or C1-C6 alkyl group;
W represents a divalent group comprising a tertiary amino group or sulfonyl group;
Y represents a residue of a compound represented by Y—OH having an alcoholic hydroxyl group);

2. The water-soluble prodrug of embodiment 1, or a pharmaceutically acceptable salt, or a hydrate or solvate thereof, wherein the water-soluble prodrug is represented by formula (2):

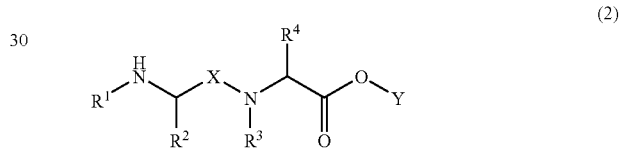

[wherein,
$R^1$ and Y are defined as in formula (1);
X represents a C=O or C1-C3 alkylene group;
$R^2$ and $R^4$ each independently represents a hydrogen atom, C1-C6 alkyl group, or amino acid side chain; and
$R^3$ represents a C1-C6 alkyl group];

3. The water-soluble prodrug of embodiment 2, or a pharmaceutically acceptable salt, or a hydrate or solvate thereof, wherein $R^1$ is a hydrogen atom, methyl group, or ethyl group;

4. The water-soluble prodrug of embodiment 2 or 3; or a pharmaceutically acceptable salt, or a hydrate or solvate thereof, wherein $R^2$ is a hydrogen atom or methyl group;

5. The water-soluble prodrug of any one of embodiments 2 to 4, or a pharmaceutically acceptable salt, or a hydrate or solvate thereof, wherein $R^3$ is a C1-C3 alkyl group;

6. The water-soluble prodrug of any one of embodiments 2 to 5, or a pharmaceutically acceptable salt, or a hydrate or solvate thereof, wherein $R^4$ is a hydrogen or methyl group;

7. The water-soluble prodrug of embodiment 1, or a pharmaceutically acceptable salt, or a hydrate or solvate thereof, wherein the water-soluble prodrug is represented by formula (3):

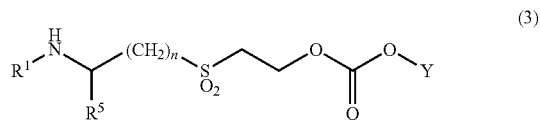

[wherein,
R¹ and Y are defined as in formula (1);
n represents an integer from 1 to 6; and
R⁵ represents a hydrogen atom or —COOR⁶ (wherein R⁶ represents a hydrogen atom or C1-C6 alkyl group)];
8. The water-soluble prodrug of embodiment 7, or a pharmaceutically acceptable salt, or a hydrate or solvate thereof, wherein R¹ is a hydrogen atom, methyl group, or ethyl group;
9. The water-soluble prodrug of embodiment 7 or 8, or a pharmaceutically acceptable salt, or a hydrate or solvate thereof, wherein n is 1, and R⁵ is a hydrogen atom or —COOR⁶ (wherein R⁶ represents a hydrogen atom or C1-C6 alkyl group);
10. The water-soluble prodrug of embodiment 7 or 8, or a pharmaceutically acceptable salt, or a hydrate or solvate thereof, wherein n is an integer from 2 to 6, and R⁵ is a hydrogen atom;
11. The water-soluble prodrug of any one of embodiments 1 to 10, or a pharmaceutically acceptable salt, or a hydrate or solvate thereof, wherein the hydroxyl group (—OH) of Y—OH is a secondary or tertiary alcoholic hydroxyl group;
12. The water-soluble prodrug of any one of embodiments 1 to 11, or a pharmaceutically acceptable salt, or a hydrate or solvate thereof, wherein Y—OH is an insoluble compound;
13. The water-soluble prodrug of any one of embodiments 1 to 12, or a pharmaceutically acceptable salt, or a hydrate or solvate thereof, wherein Y—OH is a camptothecin, azole antifungal agent, taxane, or anticancer nucleotide;
14. The water-soluble prodrug of any one of embodiments 1 to 13, or a pharmaceutically acceptable salt, or a hydrate or solvate thereof, wherein Y is a group represented by formula (4):

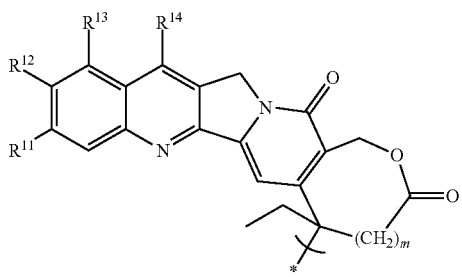

(4)

[wherein,
* indicates a linkage site;
m is either 0 or 1;
R¹¹ represents a hydrogen atom, halogen atom, or C1-C6 alkyl group;
R¹² represents a hydrogen atom, halogen atom, C1-C6 alkyl group, or hydroxyl group;
R¹³ represents a hydrogen atom, amino group, nitro group, or (dimethylamino)methyl group;
R¹⁴ represents a hydrogen atom, C1-C6 alkyl group, (4-methylpiperazinyl)methyl group, or (tert-butoxyimino)methyl group;
R¹³ and R¹⁴, and R¹¹ and R¹², may, respectively, be linked to each other to form a 5- or 6-membered ring, wherein the 5- or 6-membered ring may comprise 1 to 2 heteroatoms, and may comprise 1 to 3 substituents selected from Group A described below, wherein the substituents of Group A may further comprise 1 to 3 substituents selected from Group B described below:
Group A: a C1-C10 alkyl group, amino group, mono-C1-C8 alkylamino group, di-C1-C8 alkylamino group, C1-C8 alkoxy group, C1-C8 alkylthio group, and group represented by X═ (wherein X represents an oxygen atom or sulfur atom);
Group B: a C1-C6 alkoxy group, hydroxy group, halogen atom, amino group, mono-C1-C6 alkylamino group, di-C1-C6 alkylamino group, C3-C7 cycloalkyl group, heterocycle, and aryl ring (which may comprise 1 to 3 substituents selected from the group consisting of a hydroxy group, C1-C6 alkoxy group, halogen atom, amino group, mono-C1-C6 alkylamino group, and di-C1-C6 alkylamino group)];
15. The water-soluble prodrug of embodiment 14, or a pharmaceutically acceptable salt, or a hydrate or solvate thereof, wherein Y is a group represented by formula (5):

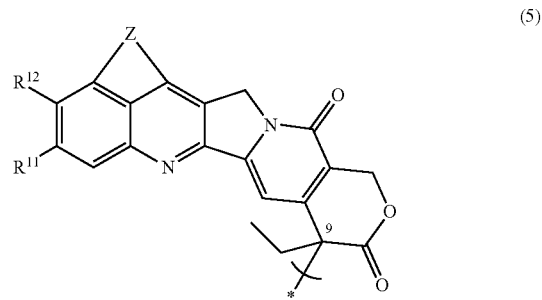

(5)

{wherein,
* indicates a linkage site;
R¹¹ and R¹² are defined as in embodiment 14; and
Z represents —NH—C(═X)—N(R²¹)— or —N═C(R²²)—N(R²¹)—
[wherein R²¹ represents a hydrogen atom or a C1-C10 alkyl group that may comprise 1-3 substituents selected from Group B described below:
Group B: a C1-C6 alkoxy group, hydroxy group, halogen atom, amino group, mono-C1-C6 alkylamino group, di-C1-C6 alkylamino group, C3-C7 cycloalkyl group, heterocycle, and aryl ring (which may comprise 1 to 3 substituents selected from the group consisting of a hydroxy group, C1-C6 alkoxy group, halogen atom, amino group, mono-C1-C6 alkylamino group, and di-C1-C6 alkylamino group);
R²² represents a hydrogen atom, amino group, or a C1-C6 alkyl group that may comprise 1 to 3 substituents selected from Group C described below, a C1-C6 alkoxy group that may comprise 1 to 3 substituents selected from Group C described below, a C1-C6 alkylthio group that may comprise 1 to 3 substituents selected from Group C described below, a mono-C1-C6 alkylamino group that may comprise 1 to 3 substituents selected from Group C described below, or a di-C1-C6 alkylamino group that may comprise 1 to 3 substituents selected from Group C described below:
Group C: a C1-C6 alkoxy group, hydroxy group, halogen atom, amino group, C3-C7 cycloalkyl group, heterocycle, and aryl ring (which may comprise 1 to 3 substituents selected from the group consisting of hydroxy group, C1-C6 alkoxy group, amino group, mono-C1-C6 alkylamino group, and di-C1-C6 alkylamino group); and X represents an oxygen atom or sulfur atom]};

16. The water-soluble prodrug of embodiment 15, or a pharmaceutically acceptable salt, or a hydrate or solvate thereof, wherein Y is a group represented by formula (6):

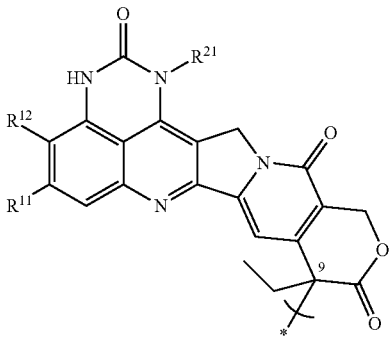

(6)

[wherein * indicates a linkage site; and
$R^{11}$, $R^{12}$, and $R^{21}$ are defined as in embodiment 15];

17. The water-soluble prodrug of embodiment 16, or a pharmaceutically acceptable salt, or a hydrate or solvate thereof, wherein $R^{11}$ and $R^{12}$ are hydrogen atoms; and
$R^{21}$ represents a hydrogen atom, or a C1-C8 alkyl group that may comprise a substituent selected from Group D described below:
Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring (which may comprise 1 to 3 substituents selected from the group consisting of a hydroxy group, C1-C3 alkoxy group, and halogen atom);

18. The water-soluble prodrug of embodiment 16 or 17, or a pharmaceutically acceptable salt, or a hydrate or solvate thereof, wherein Y is a residue of a compound (Y—OH) comprising at least one alcoholic hydroxyl group, wherein the compound is selected from the group consisting of:
a) (9S)-1-butyl-9-ethyl-9-hydroxy-1H,12H-pyrano [3",4":6',7']indolizino[1',2':6,5]pyrido[4,3,2-de]quinazoline-2,10,13(3H,9H,15H)-trione;
b) (9S)-9-ethyl-9-hydroxy-1-[2-(4-morpholino)ethyl]-1H,12H -pyrano[3",4":6',7']indolizino[1',2':6,5]pyrido[4,3,2-de]quinazoline-2,10,13(3H,9H,15H) -trione;
c) (9S)-1-[3-(dimethylamino)propyl]-9-ethyl-9-hydroxy-1H,12H -pyrano[3",4":6',7']indolizino[1',2':6,5]pyrido[4,3,2-de]quinazoline-2,10,13(3H,9H,15H) -trione;
d) (9S)-9-ethyl-9-hydroxy-1-phenethyl-1H,12H -pyrano[3",4":6',7']indolizino[1',2':6,5]pyrido[4,3,2-de]quinazoline-2,10,13(3H,9H,15H) -trione;
e) (9S)-9-ethyl-9-hydroxy-1-[2-(pyridin-2-yl)ethyl]-1H,12H -pyrano[3",4":6',7']indolizino[1',2':6,5]pyrido[4,3,2-de] quinazoline-2,10,13(3H,9H,15H) -trione;
f) (9S)-9-ethyl-1-heptyl-9-hydroxy-1H,12H -pyrano[3",4": 6',7']indolizino[1',2':6,5]pyrido[4,3,2-de]quinazoline-2, 10,13(3H,9H, 15H) -trione;
g) (9S)-9-ethyl-9-hydroxy-1-propyl-1H,12H -pyrano[3",4": 6',7']indolizino[1',2':6,5]pyrido[4,3,2-de]quinazoline-2, 10,13(3H,9H,15H) -trione;

h) (9S)-9-ethyl-9-hydroxy-1-[2-(pyridin-3-yl)ethyl]-1H, 12H -pyrano[3",4":6',7']indolizino[1',2':6,5]pyrido[4,3,2-de]quinazoline-2,10,13(3H,9H,15H) -trione;
i) (9S)-9-ethyl-9-hydroxy-1-(3-phenylpropyl)-1H,12H -pyrano[3",4":6',7']indolizino[1',2':6,5]pyrido[4,3,2-de]quinazoline-2,10,13(3H,9H,15H) trione;
j) (9S)-9-ethyl-9-hydroxy-1-(2-methylpropyl)-1H,12H -pyrano[3",4":6',7']indolizino[1',2':6,5]pyrido[4,3,2-de]quinazoline-2,10,13(3H,9H,15H) -trione;
k) (9S)-9-ethyl-1-hexyl-9-hydroxy-1H,12H -pyrano[3",4": 6',7']indolizino[1',2':6,5]pyrido[4,3,2-de]quinazoline-2, 10,13(3H,9H,15H) -trione;
l) (9S)-9-ethyl-9-hydroxy-1-pentyl-1H,12H -pyrano[3",4": 6',7']indolizino[1',2':6,5]pyrido[4,3,2-de]quinazoline-2, 10,13(3H,9H,15H) -trione;
m) (9S)-9-ethyl-9-hydroxy-1-[2-(4-methoxyphenyl)ethyl]-1H,12H -pyrano [3",4":6',7']indolizino[1',2':6,5]pyrido[4, 3,2-de]quinazoline-2,10,13(3H,9H,15H) -trione;
n) (9S)-1-benzyl-9-ethyl-9-hydroxy-1H,12H-pyrano[3",4": 6',7']indolizino[1',2':6,5]pyrido[4,3,2-de]quinazoline-2, 10,13(3H,9H,15H)-trione;
o) (9S)-9-ethyl-9-hydroxy-1-(3-methylbutyl)-1H,12H-pyrano[3",4":6',7']indolizino[1',2':6,5]pyrido[4,3,2-de] quinazoline-2,10,13(3H,9H,15H)-trione;
p) (9S)-1,9-diethyl-9-hydroxy-1H,12H-pyrano[3",4":6',7'] indolizino[1',2':6,5]pyrido[4,3,2-de]quinazoline-2,10,13 (3H,9H,15H)-trione;
q) (9S)-1-[2-(4-chlorophenyl)ethyl]-9-ethyl-9-hydroxy-1H, 12H-pyrano[3",4":6',7']indolizino[1',2':6,5]pyrido[4,3,2-de]quinazoline-2,10,13 (3H,9H,15H)-trione;
r) (9S)-9-ethyl-1-[2-(4-fluorophenyl)ethyl]-9-hydroxy-1H, 12H-pyrano[3",4":6',7']indolizino[1',2':6,5]pyrido[4,3,2-de]quinazoline-2,10,13(3H,9H,15H)-trione;
s) (9S)-9-ethyl-9-hydroxy-1-(1-methylethyl)-1H,12H-pyrano[3",4":6',7']indolizino[1',2':6,5]pyrido[4,3,2-de] quinazoline-2,10,13(3H,9H,15H)-trione; and
t) (9S)-1-(3,3-dimethylbutyl)-9-ethyl-9-hydroxy-1H,12H-pyrano[3",4":6',7']indolizino[1',2':6,5]pyrido[4,3,2-de] quinazoline-2,10,13(3H,9H,15H)-trione;

19. The water-soluble prodrug of embodiment 15, or a pharmaceutically acceptable salt, or a hydrate or solvate thereof, wherein Y is a group represented by formula (7):

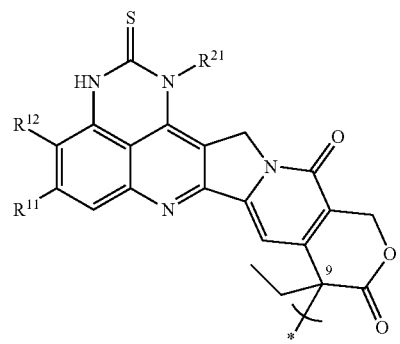

(7)

[wherein,
* indicates a linkage site; and
$R^{11}$, $R^{12}$, and $R^{21}$ are defined as in embodiment 15];

20. The water-soluble prodrug of embodiment 19, or a pharmaceutically acceptable salt, or a hydrate or solvate thereof, wherein $R^{11}$ and $R^{12}$ are hydrogen atoms; and R²¹ is a hydrogen atom, or a C1-C8 alkyl group that may comprise a substituent selected from Group D described below:
Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring (which may comprise 1 to 3 substituents selected from the group consisting of a hydroxy group, C1-C3 alkoxy group, and halogen atom);

21. The water-soluble prodrug of embodiment 19 or 20, or a pharmaceutically acceptable salt, or a hydrate or solvate thereof, wherein Y is a residue of a compound (Y—OH) comprising at least one alcoholic hydroxyl group, wherein the compound is selected from the group consisting of:
a) (9S)-9-ethyl-9-hydroxy-1-(3-methylbutyl)-1H,12H -pyrano[3",4":6',7']indolizino[1',2':6,5]pyrido[4,3,2-de]quinazoline-2(3H)-thione -10,13(9H,15H)-dione;
b) (9S)-9-ethyl-9-hydroxy-1-phenethyl-1H,12H -pyrano[3",4":6',7']indolizino[1',2':6,5]pyrido[4,3,2-de]quinazoline-2(3H)-thione -10,13(9H,15H)-dione; and
c) (9S)-9-ethyl-9-hydroxy-1-pentyl-1H,12H -pyrano[3",4":6',7']indolizino[1',2':6,5]pyrido[4,3,2-de]quinazoline-2(3H)-thione -10,13(9H,15H)-dione;

22. The water-soluble prodrug of embodiment 15, or a pharmaceutically acceptable salt, or a hydrate or solvate thereof, wherein Y is a group represented by formula (8):

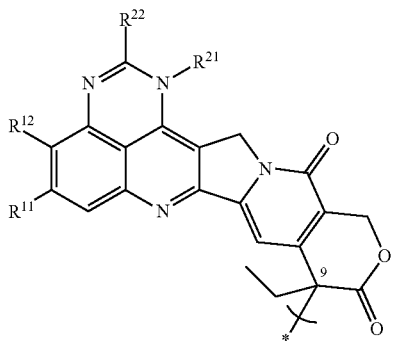

(8)

[wherein,
* indicates a linkage site; and
R¹¹, R¹², R²¹, and R²² are defined as in embodiment 15];

23. The water-soluble prodrug of embodiment 22, or a pharmaceutically acceptable salt, or a hydrate or solvate thereof, wherein R¹¹ is a hydrogen atom;
R¹² is a hydrogen atom or C1-C3 alkyl group;
R²¹ is a hydrogen atom, or a C1-C8 alkyl group that may comprise 1 to 3 substituents selected from Group D described below; and
R²² is a hydrogen atom, amino group, or a C1-C6 alkyl group that may comprise 1 to 3 substituents selected from Group D described below, a C1-C6 alkoxy group that may comprise 1 to 3 substituents selected from Group D described below, a C1-C6 alkylthio group that may comprise 1 to 3 substituents selected from Group D described below, a mono-C1-C6 alkylamino group that may comprise 1 to 3 substituents selected from Group D described below, or a di-C1-C6 alkyl amino group that may comprise 1 to 3 substituents selected from Group D described below:
Group D: a C1-C3 alkoxy group, hydroxy group, halogen atom, amino group, mono -C1-C3 alkylamino group, di-C1-C3 alkylamino group, C3-C7 cycloalkyl group, heterocycle, and aryl ring (which may comprise 1 to 3 substituents selected from the group consisting of a hydroxy group, C1-C3 alkoxy group, and halogen atom);

24. The water-soluble prodrug of embodiment 22 or 23, or a pharmaceutically acceptable salt, or a hydrate or solvate thereof, wherein Y is a residue of a compound (Y—OH) comprising at least one alcoholic hydroxyl group, wherein the compound is selected from the group consisting of:
a) (9S)-1-butyl-9-ethyl-9-hydroxy-1H,12H -pyrano[3",4":6',7']indolizino[1',2':6,5]pyrido[4,3,2-de]quinazoline-10,13 (9H,15H)-dione;
b) (9S)-9-ethyl-9-hydroxy-1-[2-(4-morpholino)ethyl]-1H,12H -pyrano[3–,4":6',7']indolizino[1',2+:6,5]pyrido[4,3,2-de]quinazoline-10,13(9H,15H)-dione;
c) (9S)-9-ethyl-9-hydroxy-1-propyl-1H,12H -pyrano[3",4":6',7']indolizino[1',2':6,5]pyrido[4,3,2-de]quinazoline-10,13(9H,15H)-dione;
d) (9S)-1-benzyl-9-ethyl-9-hydroxy-1H,12H -pyrano[3",4":6',7']indolizino[1',2':6,5]pyrido[4,3,2-de]quinazoline-10,13(9H,15H)-dione;
e) (9S)-9-ethyl-9-hydroxy-1-phenethyl-1H,12H -pyrano[3",4":6',7']indolizino[1',2':6,5]pyrido[4,3,2-de]quinazoline-10,13(9H,15H)-dione;
f) (9S)-2,9-diethyl-9-hydroxy-1-phenethyl-1H,12H -pyrano[3",4":6',7']indolizino[1',2':6,5]pyrido[4,3,2-de]quinazoline-10,13(9H,15H)-dione;
g) (9S)-9-ethyl-9-hydroxy-1-(3-phenylpropyl)-1H,12H -pyrano[3",4":6',7']indolizino[1',2':6,5]pyrido[4,3,2-de]quinazoline-10,13(9H,15H)-dione;
h) (9S)-9-ethyl-9-hydroxy-1-(3-methylbutyl)-1H,12H -pyrano[3",4":6',7']indolizino[1',2':6,5]pyrido[4,3,2-de]quinazoline-10,13(9H,15H)-dione;
i) (9S)-2,9-diethyl-9-hydroxy-1-(3-methylbutyl)-1H,12H -pyrano[3",4":6',7']indolizino[1',2':6,5]pyrido[4,3,2-de]quinazoline-10,13(9H,15H)-dione;
j) (9S)-2,9-diethyl-9-hydroxy-1-(2-methylpropyl)-1H,12H -pyrano[3",4":6',7']indolizino[1',2':6,5]pyrido[4,3,2-de]quinazoline-10,13(9H,15H)-dione;
k) (9S)-9-ethyl-1-heptyl-9-hydroxy-1H,12H -pyrano[3",4":6',7']indolizino[1',2':6,5]pyrido[4,3,2-de]quinazoline-10,13(9H,15H)-dione;
l) (9S)-9-ethyl-9-hydroxy-1-methyl-1H,12H -pyrano[3",4":6',7']indolizino[1',2':6,5]pyrido[4,3,2-de]quinazoline-10,13(9H,15H)-dione;
m) (9S)-9-ethyl-9-hydroxy-1-(2-methylpropyl)-1H,12H -pyrano[3",4":6',7']indolizino[1',2':6,5 pyrido[4,3,2-de]quinazoline-10,13(9H,15H)-dione;
n) (9S)-9-ethyl-1-hexyl-9-hydroxy-1H,12H -pyrano[3",4":6',7']indolizino[1',2':6,5]pyrido[4,3,2-de]quinazoline-10,13(9H,15H)-dione;
o) (9S)-9-ethyl-9-hydroxy-1-pentyl-1H,12H -pyrano[3",4":6',7']indolizino[1',2':6,5]pyrido[4,3,2-de]quinazoline-10,13(9H,15H)-dione;
p) (9S)-1,9-diethyl-9-hydroxy-1H,12H-pyrano[3",4":6',7']indolizino[1',2':6,5]pyrido[4,3,2-de]quinazoline-10,13(9H,15H)-dione;
q) (9S)-9-ethyl-9-hydroxy-1-[2-(4-methoxyphenyl)ethyl]-1H,12H -pyrano[3",4":6',7']indolizino[1',2':6,5]pyrido[4,3,2-de]quinazoline-10,13(9H,15H)-dione;
r) (9S)-1-[2-(4-chlorophenyl)ethyl]-9-ethyl-9-hydroxy-1H,12H -pyrano[3",4":6',7']indolizino[1',2':6,5]pyrido[4,3,2-de]quinazoline-10,13(9H,15H)-dione;
s) (9S)-9-ethyl-1-[2-(4-fluorophenyl)ethyl]-9-hydroxy-1H,12H -pyrano[3",4":6',7']indolizino[1',2':6,5]pyrido[4,3,2-de]quinazoline-10,13(9H,15H)-dione;

t) (9S)-9-ethyl-1-[2-(4-fluorophenyl)ethyl]-9-hydroxy-2-methyl-1H,12H -pyrano[3",4":6',7']indolizino[1',2':6,5]pyrido[4,3,2-de]quinazoline-10,13(9H,15H)-dione;

u) (9S)-9-ethyl-9-hydroxy-1-(1-methylethyl)-1H,12H -pyrano[3",4":6',7']indolizino[1',2':6,5pyrido[4,3,2-de]quinazoline-10,13(9H,15H)-dione;

v) (9S)-1-(3,3-dimethylbutyl)-9-ethyl-9-hydroxy-1H,12H -pyrano[3",4":6',7']indolizino[1',2':6,5]pyrido[4,3,2-de]quinazoline-10,13(9H,15H)-dione;

w) (9S)-9-ethyl-9-hydroxy-2-methoxy-1-(3-methylbutyl)-1H,12H-pyrano[3",4":6',7']indolizino[1',2':6,5]pyrido[4,3,2-de]quinazoline-10,13(9H,15H)-dione;

x) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

y) (9RS)-9-ethyl-9-hydroxy-4-methyl-1-pentyl-1H,12H-pyrano[3",4":6',7']indolizino[1',2':6,5]pyrido[4,3,2-de]quinazoline-10,13(9H,15H)-dione;

z) (9S)-9-ethyl-9-hydroxy-1-(2-hydroxyethyl)-1H,12H-pyrano[3",4":6',7']indolizino[1',2':6,5]pyrido[4,3,2-de]quinazoline-10,13(9H,15H)-dione;

aa) (9S)-9-ethyl-9-hydroxy-1-(2-hydroxyethyl)-2-methyl-1H,12H-pyrano[3",4":6',7']indolizino[1',2':6,5]pyrido[4,3,2-de]quinazoline-10,13(9H,15H)-dione;

bb) (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15 H)-dione;

cc) (9S)-2,9-diethyl-9-hydroxy-1-pentyl-1H,12H-pyrano[3",4":6',7']indolizino[1',2':6,5]pyrido[4,3,2-de]quinazoline-10,13(9H,15H)-dione;

dd) (9S)-9-ethyl-9-hydroxy-1-pentyl-2-propyl-1H,12H-pyrano[3",4":6',7']indolizino[1',2':6,5]pyrido[4,3,2-de]quinazoline-10,13(9H,15H)-dione;

ee) (9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione;

ff) (9S)-9-ethyl-9-hydroxy-2-hydroxymethyl-1-(2-methylpropyl)-1H,12H-pyrano[3",4":6',7']indolizino[1',2':6,5]pyrido[4,3,2-de]quinazoline-10,13(9H,15H)-dione;

gg) (9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione;

hh) (9S)-2-chloromethyl-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

ii) (9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H,15H)-dione;

jj) (9S)-9-ethyl-9-hydroxy-1-pentyl-2-trifluoromethyl-1H,12H-pyrano[3",4":6',7']indolizino[1',2':6,5]pyrido[4,3,2-de]quinazoline-10,13(9H,15H)-dione;

kk) (9S)-9-ethyl-9-hydroxy-1-(3-methylbutyl)-2-methylthio-1H,12H-pyrano[3",4":6',7']indolizino[1',2':6,5]pyrido[4,3,2-de]quinazoline-10,13(9H,15H)-dione;

ll) (9S)-9-ethyl-2-ethylthio-9-hydroxy-1-(3-methylbutyl)-1H,12H-pyrano[3",4":6',7']indolizino[1',2':6,5]pyrido[4,3,2-de]quinazoline-10,13(9H,15H)-dione;

mm) (9S)-2-(dimethylamino)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione; and nn) (9S)-2-(butylamino)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione.

25. The water-soluble prodrug of embodiment 13, or a pharmaceutically acceptable salt, or a hydrate or solvate thereof, wherein the azole antifungal agent is a triazole;

26. The water-soluble prodrug of embodiment 25, or a pharmaceutically acceptable salt, or a hydrate or solvate thereof, comprising at least one triazole selected from the group consisting of:

a) 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone;

b) (+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol;

c) (2R)-2-(2,4-difluorophenyl)-1-[3-[(E)-4-(2,2,3,3-tetrafluoropropoxy)-styryl]-(1,2,4-triazol-1-yl)-3-(1,2,4-triazol-1-yl)]propan-2-ol;

d) dl-threo-2-(2,4-difluorophenyl)-3-methyl-sulfonyl-1-(1H-1,2,4-triazol-1-yl)-butan-2-ol;

e) (−)-4-[4-[4-[4-[[5-(2,4-difluorophenyl)-5-(1H-1,2,4-triazol-1-ylmethyl)tetrahydrofuran-3-yl]methoxy]phenyl]piperazinyl]phenyl]-2[(1S,2S)-1-ethyl-2-hydroxypropyl]-3H-1,2,4-triazol-3-one;

f) (2R,3R)-3-[4-(4-cyanophenyl)thiazol-2-yl]]-2-(2,4-difluorophenyl)-1-(1H-1,2,4-triazol-1-yl)-butan-2-ol;

g) 3-methyl-3-methylthio-1-(1,2,4-triazol-1-yl)-2-(trifluoromethylphenyl)-butan-2-ol;

h) (2R,3R)-3-[4-(4-cyanophenyl)thiazol-2-yl]]-1-(1H-1,2,4-triazol-1-yl)-2-(2,4,5-trifluorophenyl)-butan-2-ol;

i) (2R,3R)-3-[4-(4-cyanophenyl)thiazol-2-yl]]-2-(3-fluorophenyl)-1-(1H-1,2,4-triazol-1-yl)-butan-2-ol; and j) (2R,3R)-3-[4-(4-cyanophenyl)thiazol-2-yl]]-2-(2,5-difluorophenyl)-1-(1H-1,2,4-triazol-1-yl)-butan-2-ol;

27. The water-soluble prodrug of embodiment 1 represented by the formula (1), or a pharmaceutically acceptable salt, or a hydrate or solvate thereof, comprising at least one water-soluble prodrug selected from the group consisting of:

(a) (9S)-9-ethyl-9-{[methyl-(2-methylamino-ethyl)-amino]-acetoxy}-1-pentyl-1H,12H-pyrano[3",4":6',7']indolizino[1',2':6,5]pyrido[4,3,2-de]quinazoline-10,13(9H,15H)-dione;

(b) (9S)-9-ethyl-9-(glycyl-sarcosyloxy)-1-pentyl-1H,12H-pyrano[3",4":6',7']indolizino[1',2':6,5]pyrido[4,3,2-de]quinazoline-10,13(9H,15H)-dione;

(c) (9S)-9-{[(2-amino-ethyl)-methyl-amino-acetoxy}-9-ethyl-1-pentyl-1H,12H-pyrano[3",4":6',7']indolizino[1',2':6,5]pyrido[4,3,2-de]quinazoline-10,13(9H,15H)-dione;

(d) (9S)-9-ethyl-9-(sarcosyl-sarcosyloxy)-1-pentyl-1H,12H-pyrano[3",4":6',7']indolizino[1',2':6,5]pyrido[4,3,2-de]quinazoline-10,13(9H,15H)-dione;

(e) (9S)-9-[2-(2-aminoethanesulfonyl)ethoxycarbonyloxy]-9-ethyl-1-pentyl-1H,12H-pyrano[3",4":6',7']indolizino[1',2':6,5]pyrido[4,3,2-de]quinazoline-10,13(9H,15H)-dione;

(f) (aminoacetyl-methyl-amino)-acetic acid (S)-4-ethyl-3,13-dioxo-3,4,12,13-tetrahydro-1H-2-oxa-6,12a-diazadibenzo[b,h]fluoren-4-yl ester;

(g) (9S)-9-{2-[(R-2-amino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione;

(h) (9S)-9-{2-[(R-2-amino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione;

(i) (9S)-9-ethyl-9-(N-methylalanyl-N-methylalanyloxy)-1-pentyl-1H,12H-pyrano[3",4":6',7']indolizino[1',2':6,5]pyrido[4,3,2-de]quinazoline-10,13(9H,15H)-dione; and (j) (9S)-9-ethyl-9-(sarcosyl-N-methylalanyloxy)-1-pentyl-1H,12H-pyrano[3",4":6',7']indolizino[1',2':6,5]pyrido[4,3,2-de]quinazoline-10,13(9H,15H)-dione;

28. A pharmaceutical composition comprising the water-soluble prodrug of any one of embodiments 1 to 27, or a pharmaceutically acceptable salt, or a hydrate or solvate thereof, as an effective ingredient;

29. A therapeutic agent for a cell proliferation disorder comprising the water-soluble prodrug of any one of embodiments 14 to 24, or a pharmaceutically acceptable salt, or a hydrate or solvate thereof, as an effective ingredient;

30. The therapeutic agent according to embodiment 29, wherein the cell proliferation disorder is a cancer;

31. The therapeutic agent according to embodiment 30, wherein the cancer is a solid tumor;

32. The therapeutic agent according to embodiment 30 or 31, wherein the cancer is a colorectal cancer, lung cancer, breast cancer, gastric cancer, uterine cervical cancer, and/or bladder cancer;

33. An antifungal agent comprising the water-soluble prodrug of any one of embodiments 25 to 27, or a pharmaceutically acceptable salt, or a hydrate or solvate thereof, as an effective ingredient; and 34. A use of a compound represented by formula (9) in the production of a water-soluble prodrug represented by formula (2), a pharmaceutically acceptable salt thereof, or a hydrate or solvate thereof:

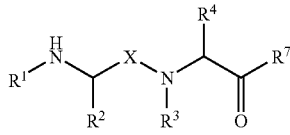

(9)

[wherein,
X represents a C=O or C1-C3 alkylene group;
$R^1$ represents a hydrogen atom, or C1-C6 alkyl group;
the nitrogen atom binding to $R^1$ may be protected by a protecting group;
$R^2$ and $R^4$ each independently represents a hydrogen atom, C1-6 alkyl group, or amino acid side chain;
$R^3$ represents a C1-C6 alkyl group; and
$R^7$ represents a halogen atom or group represented by $OR^8$ (wherein $R^8$ represents a hydrogen atom or C1-C6 alkyl group)]

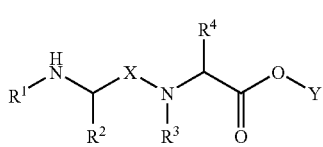

(2)

(wherein,
Y represents a residue of a compound represented by Y—OH which comprises an alcoholic hydroxyl group; and
X, $R^1$, $R^2$, $R^3$, and $R^4$ are defined as in formula (9));

35. A method of producing a compound represented by formula (2);

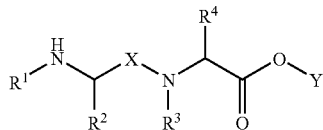

(2)

(wherein,
X represents a C=O or C1-C3 alkylene group;
$R^1$ represents a hydrogen atom, or C1-C6 alkyl group;
$R^2$ and $R^4$ each independently represents a hydrogen atom, C1-6 alkyl group, or amino acid side chain; and
$R^3$ represents a C1-C6 alkyl group;
Y represents a residue of a compound represented by Y—OH which comprises an alcoholic hydroxyl group), wherein the method comprises the step of: reacting a compound represented by formula (9)

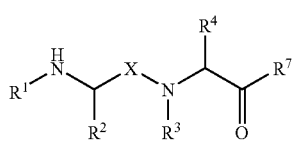

(9)

[wherein, X, $R^1$, $R^2$, $R^3$, and $R^4$ are defined as in formula (2);
$R^7$ represents a halogen atom or group represented by $OR^8$ (wherein $R^8$ represents a hydrogen atom or C1-C6 alkyl group); and
the nitrogen atom binding to $R^1$ may be protected by a protecting group]
with a compound represented by Y—OH which includes an alcoholic hydroxyl group to obtain the compound represented by formula (2);

36. A compound represented by formula (9), a pharmaceutically acceptable salt thereof, or a hydrate or solvate thereof:

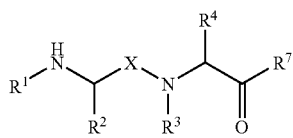

(9)

[wherein,
X represents a C=O or C1-C3 alkylene group;
$R^1$ represents a hydrogen atom, or C1-C6 alkyl group;
the nitrogen atom binding to $R^1$ may be protected by a protecting group;
$R^2$ and $R^4$ each independently represents a hydrogen atom, C1-6 alkyl group, or amino acid side chain;
$R^3$ represents a C1-C6 alkyl group; and
$R^7$ represents a halogen atom or group represented by $OR^8$ (wherein $R^8$ represents a hydrogen atom or C1-C6 alkyl group)].

As used herein, the term "alkyl group" refers to a monovalent group, which is derived by removing a single hydrogen atom from an aliphatic hydrocarbon, and has a partial assembly of hydrocarbyl or hydrocarbon structure comprising hydrogen and carbon atoms, and does not contain a heteroatom or an unsaturated carbon-carbon bond in its backbone. The alkyl group may have a straight-chain or branched-chain structure.

The term "C1-C3 alkyl group" refers to an alkyl group with 1 to 3 carbon atoms, the term "C1-C6 alkyl group" refers to an alkyl group with 1 to 6 carbon atoms, the term "C1-C8 alkyl group" refers to an alkyl group with 1 to 8 carbon atoms, and the term "C1-C10 alkyl group" refers to an alkyl group with 1 to 10 carbon atoms.

Specific examples of the alkyl group include a methyl group, ethyl group, n-propyl group, i-propyl group, n-butyl group, sec-butyl group, t-butyl group, isobutyl group, pentyl group, isopentyl group, 2,3-dimethylpropyl group, hexyl group, 2,3-dimethylhexyl group, 1,1-dimethylpentyl group, heptyl group, and octyl group.

As used herein, the term "alkylene group" refers to a divalent group derived by removing a second hydrogen atom from the alkyl group defined above, and examples of the alkylene group preferably include a C1-C3 alkylene group, and more preferably include a C1-C2 alkylene group. Specific examples of the alkylene group include a methylene group, 1,2-ethylene group, 1,1-ethylene group, 1,3-propylene group, tetramethylene group, pentamethylene group, and hexamethylene group.

As used herein, the term "alkoxy group" refers to an —O—R' group, wherein R' is the alkyl group defined above. Examples of the "C1-C6 alkoxy group" include a methoxy group, ethoxy group, propoxy group, isopropoxy group, butoxy group, isobutoxy group, tert-butoxy group, pentoxy group, 3-methylbutoxy group, and 2,2-dimethylpropoxy group.

As used herein, the term "alkylthio group" refers to an —S—R' group, in which R' is the alkyl group defined above. Examples of the "C1-C8 alkylthio group" include a methylthio group, ethylthio group, propylthio group, butylthio group, pentylthio group, hexylthio group, heptylthio group, and octylthio group.

As used herein, the term "hydroxy group" refers to an HO— group.

As used herein, the term "halogen atom" refers to a fluorine atom, chlorine atom, bromine atom, or iodine atom.

As used herein, the term "amino group" refers to an $NH_2$— group, and includes amino groups protected with formyl, acetyl, trityl, tert-butoxycarbonyl, benzyl, benzyloxycarbonyl, and such protecting groups that are well known in the art. Among the amino groups, $NH_2$— is preferred.

As used herein, the term "monoalkylamino group" refers to an —NH—R' group, wherein R' is the alkyl group defined above, and includes amino groups protected with formyl, acetyl, trityl, tert-butoxycarbonyl, benzyl, benzyloxycarbonyl, and such protecting groups that are well known in the art. Examples of the "mono-C1-C6 alkylamino group" preferably include an N-methylamino group, N-ethylamino group, N-propylamino group, N-isopropylamino group, N-butylamino group, N-(1-methylpropyl)amino group, N-(2-methylpropyl)amino group, and N-pentylamino group, and more preferably include N-ethylamino group, N-propylamino group, and N-butylamino group.

As used herein, the term "dialkylamino group" refers to an —NR'R" group, wherein R' and R" each independently represents an alkyl group defined above. Examples of the "di-C1-C6 alkylamino group" preferably include an N,N-dimethylamino group, N,N-diethylamino group, N,N-dipropylamino group, N,N-diisopropylamino group, N,N-dibutylamino group, N-methyl-N-ethylamino group, and N-methyl-N-propylamino group, and more preferably include an N,N-dimethylamino group and N,N-diethylamino group.

As used herein, the term "tertiary amino group" refers to a group in which all of the hydrogens of an amino group are substituted.

As used herein, the term "sulfonyl group" refers to a group represented by —$SO_2$—.

As used herein, the term "alcoholic residue" refers to the portion represented by Y in the alcohol represented by Y—OH.

As used herein, the term "C3-C7 cycloalkyl group" refers to a 3- to 7-membered ring that does not comprise any heteroatom in the ring. Examples of the "cycloalkyl group" preferably include a cyclopropyl group, cyclobutyl group, cyclopentyl group, cyclohexyl group, and cycloheptyl group, and more preferably include a cyclopentyl group and cyclohexyl group.

As used herein, the term "heterocycle" refers to a 3- to 10-membered ring comprising one or more heteroatoms selected from N, S, and O. Preferred examples of such include an oxazolyl group, thiazolyl group, 4,5-dihydrooxazolyl group, 4,5-dihydrothiazolyl group, furyl group, pyrolyl group, thienyl group, imidazolyl group, triazolyl group, tetrazolyl group, pyridyl group, pyrazinyl group, pyrimidinyl group, triazinyl group, oxadiazolyl group, thiadiazolyl group, pyrrolidinyl group, tetrahydrothienyl group, tetrahydrofuryl group, morpholinyl group, piperidyl group, piperazinyl group, and 1-methylpiperazinyl group, and more preferably include an imidazolyl group, pyridyl group, morpholinyl group, and pyrrolidinyl group.

As used herein, the term "aryl ring" refers to an aromatic carbocyclic group, or more specifically a 6- to 10-membered aromatic ring or a partially aromatic ring, and examples include phenyl, naphthyl, and tetrahydronaphthyl rings, preferably phenyl and naphthyl rings, and most preferably phenyl rings.

As used herein, the term "phenyl-C1-C8 alkyl group" refers to a group in which one of the hydrogen atoms of the C1-C8 alkyl group is substituted with a phenyl group.

As used herein, the term "heterocyclic-C1-C8 alkyl group" refers to a group in which one of the hydrogen atoms of the C1-C8 alkyl group is substituted with a heterocycle.

As used herein, the term "alkoxyphenyl C1-C8 alkyl group" refers to a group in which one of the hydrogen atoms of the C1-C8 alkyl group is substituted with an alkoxyphenyl group. The term "alkoxyphenyl group" refers to a group in which one of the hydrogen atoms of the phenyl group is substituted with an alkoxy group.

As used herein, the term "halogen phenyl C1-C8 alkyl group" refers to a group in which one of the hydrogen atoms of the C1-C8 alkyl group is substituted with a halogen atom.

The term "pharmaceutically acceptable salt" refers to a common salt of the water-soluble prodrug represented by formula (1), which is formed with an appropriate nontoxic organic or inorganic acid, or an organic or inorganic base, and which maintains the prodrug's biological efficacy and characteristic.

Examples of the salt with an acid include those derived from inorganic acids such as hydrochloric acid, hydrobromic acid, hydroiodic acid, sulfuric acid, sulfamic acid, phosphoric acid, and nitric acid; and those derived from organic acids such as p-toluenesulfonic acid, salicylic acid, methanesulfonic acid, oxalic acid, succinic acid, citric acid, malic acid, lactic acid, and fumaric acid.

Examples of the salt with a base include those derived from potassium hydroxide, sodium hydroxide, ammonium hydroxide, and quaternary ammonium hydroxide such as tetramethylammonium hydroxide.

The water-soluble prodrug of the present invention may absorb moisture, adsorb water, or form hydrates when it is left to stand in the atmosphere, and such hydrates are also included in this invention.

Furthermore, the water-soluble prodrug of the present invention may absorb certain other types of solvents to form solvates, and such solvates are also included in this invention.

Examples of the "amino acid side chain" as used herein include naturally occurring amino acid side chains and non-naturally occurring amino acid side chains.

Examples of the "naturally occurring amino acid side chain" are preferably side chains of naturally occurring amino acids such as a methyl group, isopropyl group, 2-methylpropyl group, 1-methylpropyl group, benzyl group, indol-3-ylmethyl group, 2-(methylthio)ethyl group, 4-aminobutyl group, and 3-aminopropyl group, and more preferably side chains of naturally occurring lipophilic amino acids such as a methyl group, 2-methylpropyl group, benzyl group, and indol-3-ylmethyl group.

Examples of the "non-naturally occurring amino acid side chain" are preferably C5-C12 alkyl groups, cycloalkylmethyl groups, substituted or unsubstituted arylmethyl groups, (cycloalkylthio)methyl groups, and alkylthio-$(CH_2)_r$— in which r is an integer of 1 or 2.

Examples of the "C5-C12 alkyl group" are straight-chain or branched-chain alkyl groups comprising 5 to 12 carbon atoms; and more preferably C8-C12 straight-chain alkyl groups such as an n-octyl group, nonyl group, decyl group, undecyl group, and dodecyl group.

Examples of "alkylthio-$(CH_2)_r$—" are alkylthiomethyl groups or alkylthioethyl groups comprising a straight or branched alkyl chain containing 2 to 10 carbon atoms, such as an ethylthiomethyl group, ethylthioethyl group, n-propylthiomethyl group, n-butylthiomethyl group, n-pentylthiomethyl group, n-octylthiomethyl group, n-nonylthiomethyl group, n-decylthiomethyl group, and tert-butylthiomethyl group; and more preferably an ethylthioethyl group, n-propylthiomethyl group, and n-butylthiomethyl group.

Examples of the "substituted or unsubstituted arylmethyl group" preferably include a 4-phenylbenzyl group, naphtho-2-ylmethyl group, [4-(4-hydroxyphenoxy)phenyl]methyl group, and (4-lower-alkoxyphenyl)methyl group (the term "lower-alkoxy" refers to a straight or branched alkyl chain containing 1 to 6 carbon atoms, and preferred examples include a methoxy group, ethoxy group, propoxy group, butoxy group, and isopropoxy group). The most preferred embodiments of the "substituted or unsubstituted arylmethyl group" include a 4-phenylbenzyl group, naphtho-2-ylmethyl group, (4-methoxyphenyl)methyl group, and [4-(4-hydroxyphenoxy)phenyl]methyl group.

As used herein, the term "insoluble compound" refers to all compounds insoluble in water, and examples are compounds whose solubility in distilled water is preferably 1 mg/mL or less, more preferably 0.1 mg/mL or less (the solubility meets the specifications of "Japanese Pharmacopoeia, 14th edition, Generic Rule 23"). Examples of such compounds include camptothecins, azole antifungal agents, taxanes, and anticancer nucleotides.

As used herein, the term "solubilizing side chain" refers to a group that binds to "Y", or for example in equation (1), it refers to "$R^1$—NH—W—CO—O—".

As used herein, the term "active form" refers to a compound (Y—O—) that is given by hydrolysis of the water-soluble prodrug, a pharmaceutically acceptable salt thereof, or a hydrate or solvate thereof.

The term "taxanes" in the present invention refers to taxol [Front. Biotechnol. Pharm. (2000), 1, 336-348], taxotere [J. Med. Aromat. Plant Sci. (2001), 22/4A-23/1A 4-5], IDN 5109 [Chirality, (2000), 12(5/6), 431-441], BMS 188797 [Clinical Cancer Research. 5 (suppl.), 3859, November 1999], and BMS184476[J. Clinical Oncology 19: 2493-2503, 1 May 2001].

As used herein, the term "camptothecins" [(a) Cancer Chemotherapy and Biotherapy: Principle and Practice, 2nd edition, Lippincott-Ravenmeans, p. 463-484, (b) Biochim. Biophys. Acta (1998), 1400(1-3), 107-119] refers to any compound comprising a camptothecin backbone, such as camptothecin, SN-38, 9-aminocamptothecin, 9-nitrocamptothecin, and BN-80915 [Anti-cancer Drugs (2001), 12(1), 9-19].

As used herein, the term "anticancer nucleosides" refers to cytidine derivatives [Cancer Chemotherapy and Biotherapy: Principle and Practice, 2nd edition, Lippincott-Ravenmeans, p. 213-233] such as DFDC (gemcitabine), DMDC [Clin. Cancer Res. (2000), 6(6), 2288-2294], FMDC [Curr. Opin. Invest. Drugs (PharmaPress Ltd.) (2000), 1(1), 135-140], Ara-C, decitabine, [IDrugs (2000), 3(12), 1525-1533], troxacitabine [Clin. Cancer Res. (2000), 6(4), 1574-1588], 2'-cyano-2'-deoxycytidine (CNDAC), 3'-ethynylcytidine (TAS106) [Jpn. J. Cancer Res. (2001), 92(3), 343-351], 5-fluoro-5'-deoxycytidine [Bioorg. Med. Chem. Lett., (2000), 8, 1697-1706], and 5-vinyl-5'-deoxycytidine, or adenosine derivatives [Cancer Chemotherapy and Biotherapy: Principle and Practice, 2nd edition, Lippincott-Ravenmeans, p. 235-252] such as fludarabine, and cladribine.

As used herein, the term "cell proliferation disorder" refers to a disorder caused by a defect in the intracellular signal transduction system, or in the signal transduction mechanism of a certain protein, and examples include those that cause cancer.

Among the prodrugs of the present invention represented by formula (1), examples of preferred compounds are the following.

Among the water-soluble prodrugs represented by formula (1), the compounds represented by formula (2) or (3) are preferred.

In the compounds represented by formula (2), $R^1$ is preferably a hydrogen atom, methyl group or ethyl group; and more preferably a hydrogen atom or methyl group; and particularly preferably a hydrogen atom.

X is preferably a carbonyl group or methylene group, and is more preferably a carbonyl group.

$R^2$ is preferably a hydrogen atom or methyl group.

$R^4$ is preferably a hydrogen atom or methyl group.

$R^3$ is preferably a C1-C3 alkyl group, and is more preferably a methyl group or ethyl group, and particularly preferably a methyl group.

Examples of preferred combinations of X, and $R^1$ to $R^4$ that constitute the solubilizing side chain portion of the compound represented by formula (2) are shown below, but the present invention is not to be construed as being limited thereto.

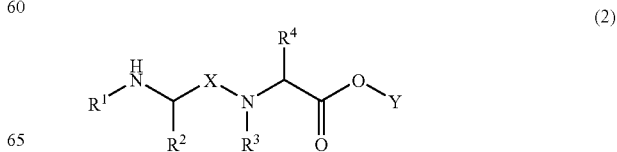

(2)

TABLE 1

|   | $R^1$ | $R^2$ | $R^3$ | $R^4$ | X |
|---|---|---|---|---|---|
| 1 | H | H or —CH$_3$ | —CH$_3$ | H or —CH$_3$ | C=O |
| 2 | H | H or —CH$_3$ | —C$_2$H$_5$ | H or —CH$_3$ | C=O |
| 3 | —CH$_3$ | H or —CH$_3$ | —CH$_3$ | H or —CH$_3$ | C=O |
| 4 | —CH$_3$ | H or —CH$_3$ | —C$_2$H$_5$ | H or —CH$_3$ | C=O |
| 5 | —C$_2$H$_5$ | H or —CH$_3$ | —CH$_3$ | H or —CH$_3$ | C=O |
| 6 | —C$_2$H$_5$ | H or —CH$_3$ | —C$_2$H$_5$ | H or —CH$_3$ | C=O |
| 7 | H | H or —CH$_3$ | —CH$_3$ | H or —CH$_3$ | —CH$_2$— |
| 8 | H | H or —CH$_3$ | —C$_2$H$_5$ | H or —CH$_3$ | —CH$_2$— |
| 9 | —CH$_3$ | H or —CH$_3$ | —CH$_3$ | H or —CH$_3$ | —CH$_2$— |
| 10 | —CH$_3$ | H or —CH$_3$ | —C$_2$H$_5$ | H or —CH$_3$ | —CH$_2$— |
| 11 | —C$_2$H$_5$ | H or —CH$_3$ | —CH$_3$ | H or —CH$_3$ | —CH$_2$— |
| 12 | —C$_2$H$_5$ | H or —CH$_3$ | —C$_2$H$_5$ | H or —CH$_3$ | —CH$_2$— |

Within Table 1, examples of compounds of formula (2) are preferably those that comprise solubilizing side chains included in reference numbers 1, 2, 3, and 4, and more preferably those that comprise solubilizing side chains included in reference numbers 1 and 2.

If such a solubilizing side chain is present, even if Y—OH is an insoluble compound, it can be converted into a compound having good water solubility. For example, such a water-soluble prodrug can exist stably for a long period of time in a solution at pH4 or lower; but when at pH5 or higher, and particularly when at physiological conditions of pH7 to 8, the active form derived from the secondary or tertiary alcoholic hydroxyl group can be dissociated quantitatively and rapidly within a short period of time.

In the compound represented by formula (3), $R^1$ is preferably a hydrogen atom, methyl group, or ethyl group; and more preferably a hydrogen atom or methyl group; and particularly preferably a hydrogen atom.

In equation (3), n is preferably in the range of 1 to 3, and is more preferably 1.

When n is 1, $R^5$ is preferably a hydrogen atom or —COOR$^6$ ($R^6$ is a C1-C3 alkyl group), and more preferably a hydrogen atom, —COOCH$_3$, or —COOC$_2$H$_5$.

When n is in the range of 2 to 6, $R^5$ is preferably a hydrogen atom.

Examples of preferred combinations of n, $R^1$, and $R^5$ that constitute the solubilizing side chain portion of such a compound represented by formula (3) are shown below, but the present invention is not to be construed as being limited thereto.

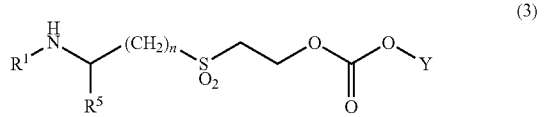

(3)

TABLE 2

|   | $R^1$ | n | $R^5$ |
|---|---|---|---|
| 1 | H | 1 | H |
| 2 | H | 1 | —CO$_2$CH$_3$ |
| 3 | H | 1 | —CO$_2$C$_2$H$_5$ |
| 4 | —CH$_3$ | 1 | H |
| 5 | —CH$_3$ | 1 | —CO$_2$CH$_3$ |
| 6 | —CH$_3$ | 1 | —CO$_2$C$_2$H$_5$ |
| 7 | —C$_2$H$_5$ | 1 | H |
| 8 | —C$_2$H$_5$ | 1 | —CO$_2$CH$_3$ |
| 9 | —C$_2$H$_5$ | 1 | —CO$_2$C$_2$H$_5$ |
| 10 | H | 2 | H |
| 11 | H | 2 | —CO$_2$CH$_3$ |

TABLE 2-continued

|   | $R^1$ | n | $R^5$ |
|---|---|---|---|
| 12 | H | 2 | —CO$_2$C$_2$H$_5$ |
| 13 | —CH$_3$ | 2 | H |
| 14 | —CH$_3$ | 2 | —CO$_2$CH$_3$ |
| 15 | —CH$_3$ | 2 | —CO$_2$C$_2$H$_5$ |
| 16 | —C$_2$H$_5$ | 2 | H |
| 17 | —C$_2$H$_5$ | 2 | —CO$_2$CH$_3$ |
| 18 | —C$_2$H$_5$ | 2 | —CO$_2$C$_2$H$_5$ |
| 19 | H | 3 | H |
| 20 | H | 3 | —CO$_2$CH$_3$ |
| 21 | H | 3 | —CO$_2$C$_2$H$_5$ |
| 22 | —CH$_3$ | 3 | H |
| 23 | —CH$_3$ | 3 | —CO$_2$CH$_3$ |
| 24 | —CH$_3$ | 3 | —CO$_2$C$_2$H$_5$ |
| 25 | —C$_2$H$_5$ | 3 | H |
| 26 | —C$_2$H$_5$ | 3 | —CO$_2$CH$_3$ |
| 27 | —C$_2$H$_5$ | 3 | —CO$_2$C$_2$H$_5$ |

Within Table 2, examples of compounds of formula (3) that comprise a solubilizing side chain are preferably those of reference numbers 1, 2, 3, 4, 5, and 6, and more preferably those of reference numbers 1, 3, and 4.

If such a solubilizing side chain is present, even if Y—OH is an insoluble compound, it can be converted into a compound having good water solubility. For example, the water-soluble prodrug can exist stably for a long period of time in a solution at pH4 or lower; but when at pH5 or higher, and particularly when at physiological conditions of pH7 to 8; the active form derived from the secondary or tertiary alcoholic hydroxyl group can be dissociated quantitatively and rapidly within a short period of time.

In the present invention, Y in formula (1) is a residue of a compound represented by Y—OH which has an alcoholic hydroxyl group.

The hydroxyl group of Y—OH is preferably a secondary or tertiary alcoholic hydroxyl group. Such Y—OH may be an insoluble compound, but even if it is insoluble, it will show good water solubility upon attachment of an aforementioned group. Furthermore, the water-soluble prodrug can exist stably for a long period of time in a solution at pH4 or lower; but when at pH5 or higher, and particularly when at physiological conditions of pH7 to 8, the active form (Y—O—) derived from the alcoholic hydroxyl group can be dissociated quantitatively and rapidly within a short period of time.

Y—OH included in the aforementioned formula of the present invention that may be attached with a solubilizing group is not particularly limited as long as it is a compound comprising an alcoholic hydroxyl group, preferably a secondary or tertiary alcoholic hydroxyl group, and more preferably a tertiary alcoholic hydroxyl group.

Examples of such compounds are preferably camptothecins, azole antifungal agents, taxanes, and anticancer nucleotides.

Camptothecins

Herein, examples of groups derived from camptothecins include the groups represented by Y shown below.

The aforementioned Y is a group represented by formula (4):

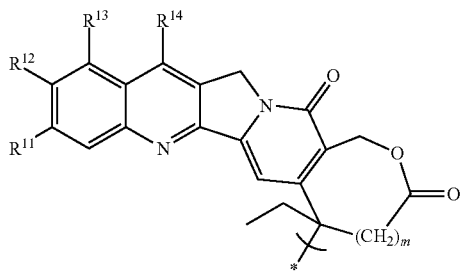

wherein,
* indicates a linkage site;
m is either 0 or 1;
$R^{11}$ represents a hydrogen atom, halogen atom, or C1-C6 alkyl group;
$R^{12}$ represents a hydrogen atom, halogen atom, C1-C6 alkyl group, or hydroxyl group;
$R^{13}$ represents a hydrogen atom, amino group, nitro group, or (dimethylamino)methyl group;
$R^{14}$ represents a hydrogen atom, C1-C6 alkyl group, (4-methylpiperazinyl)methyl group, or (tert-butoxyimino) methyl group; and
$R^{13}$ and $R^{14}$, and $R^{11}$ and $R^{12}$, respectively, may be linked to each other to form a 5- or 6-membered ring, wherein the 5- or 6-membered ring may comprise 1 to 2 heteroatoms, and may comprise 1 to 3 substituents selected from Group A described below, wherein the substituents of said Group A may further comprise 1 to 3 substituents selected from Group B described below:
  Group A: a C1-C10 alkyl group, amino group, mono-C1-C8 alkylamino group, di-C1-C8 alkylamino group, C1-C8 alkoxy group, C1-C8 alkylthio group, and group represented by X= (wherein X represents an oxygen atom or sulfur atom);
  Group B: a C1-C6 alkoxy group, hydroxy group, halogen atom, amino group, mono-C1-C6 alkylamino group, di-C1-C6 alkylamino group, C3-C7 cycloalkyl group, heterocycle, and aryl ring (which may comprise 1 to 3 substituents selected from the group consisting of a hydroxy group, C1-C6 alkoxy group, halogen atom, an amino group, mono-C1-C6 alkylamino group, and di-C1-C6 alkylamino group).

In the group represented by formula (4), the stereochemistry of the carbon, to which the oxygen atom derived from the alcoholic hydroxyl group binds, preferably has S configuration.

Herein, a preferred embodiment of the compounds represented by formula (4) includes compounds in which $R^{11}$ is preferably a hydrogen atom, $R^{12}$ is preferably a hydrogen atom or hydroxyl group, $R^{13}$ represents a hydrogen atom or (dimethylamino)methyl group, and $R^{14}$ represents a hydrogen atom or ethyl group.

Examples of compounds represented by formula (4) include the following compounds:
4(S)-ethyl-4-hydroxy-1H-pyrano[3',4':6,7]indolizino[1,2-b] quinoline-3,14(4H,12H)-dione(camptothecin);
9-aminocamptothecin;
9-nitrocamptothecin;
5(R)-ethyl-9,10-difluoro-1,4,5,13-tetrahydro-5-hydroxy-3H,15H-oxepino[3',4':6,7]indolizino[1,2-b]quinoline-3,15-dione (BN-80915); and
7-ethyl-10-hydroxycamptothecin (SN-38).

Another preferred embodiment of the compounds represented by formula (4) includes compounds in which the aforementioned Y is represented by generic formula (5):

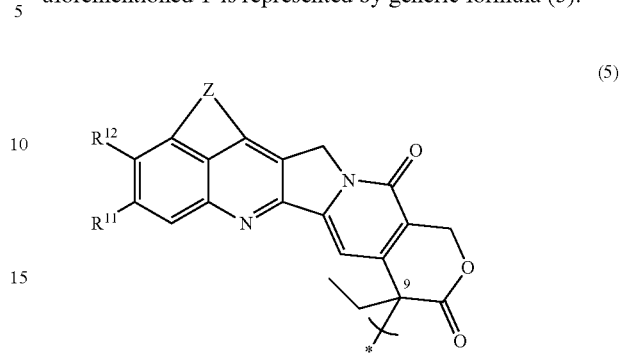

wherein,
* indicates a linkage site;
$R^{11}$ and $R^{12}$ have the same meaning as $R^{11}$ and $R^{12}$ defined in formula (4), respectively; and
Z represents —NH—C(=X)—N($R^{21}$)— or —N=C($R^{22}$)—N($R^{21}$)—.

Herein,
  $R^{21}$ represents a hydrogen atom or a C1-C10 alkyl group that may comprise 1-3 substituents selected from Group B described below:
    Group B: a C1-C6 alkoxy group, hydroxy group, halogen atom, amino group, mono-C1-C6 alkylamino group, di-C1-C6 alkylamino group, C3-C7 cycloalkyl group, heterocycle and an aryl ring (which may comprise 1 to 3 substituents selected from the group consisting of a hydroxy group, C1-C6 alkoxy group, halogen atom, an amino group, mono-C1-C6 alkylamino group, and di-C1-C6 alkylamino group);
  $R^{22}$ represents a hydrogen atom, amino group, or a C1-C6 alkyl group that may comprise 1 to 3 substituents selected from Group C described below, a C1-C6 alkoxy group that may comprise 1 to 3 substituents selected from Group C described below, a C1-C6 alkylthio group that may comprise 1 to 3 substituents selected from Group C described below, a mono-C1-C6 alkylamino group that may comprise 1 to 3 substituents selected from Group C described below, or a di-C1-C6 alkylamino group that may comprise 1 to 3 substituents selected from Group C described below:
    Group C: a C1-C6 alkoxy group, hydroxy group, halogen atom, amino group, C3-C7 cycloalkyl group, heterocycle, and aryl ring (which may comprise 1 to 3 substituents selected from the group consisting of a hydroxy group, C1-C6 alkoxy group, amino group, mono-C1-C6 alkylamino group, and di-C1-C6 alkylamino group); and,
  X represents an oxygen atom or sulfur atom.

Furthermore, preferred examples of compounds in which Y is represented by formula (5) are compounds that comprise Y represented by formula (6), (7), or (8).

The aforementioned Y is a water-soluble prodrug represented by formula (6) below.

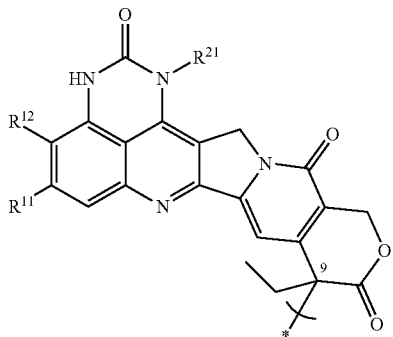

(6)

$R^{11}$, $R^{12}$, and $R^{21}$ are defined as in formulae (4) and (5).

In formula (6), $R^{11}$ and $R^{12}$ are preferably hydrogen atoms.

$R^{21}$ is preferably a hydrogen atom, or a C1-C8 alkyl group that may comprise a substituent selected from Group D shown below:

Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring (which may comprise 1 to 3 substituents selected from the group consisting of a hydroxy group, C1-C3 alkoxy group, and halogen atom).

$R^{21}$ is more preferably a C1-C8 alkyl group, phenyl-C1-C8 alkyl group, heterocyclic-C1-C8 alkyl group, alkoxyphenyl C1-C8 alkyl group, or halogenated phenyl C1-C8 alkyl group.

$R^{21}$ is even more preferably a methyl group, ethyl group, n-propyl group, 1-methylethyl group, n-butyl group, 1,1-dimethylethyl group, 2-methylpropyl group, 2,2-dimethylpropyl group, n-pentyl group, 3-methylbutyl group, 2-n-hexyl group, 3,3-dimethylbutyl group, n-heptyl group, n-octyl group, benzyl group, phenethyl group, 2-(dimethylamino)ethyl group, 2-(4-morpholino)ethyl group, 3-(dimethylamino)propyl group, 2-(pyridin-2-yl)ethyl group, 2-(pyridin-3-yl)ethyl group, 2-(4-methoxyphenyl)ethyl group, 2-(4-chlorophenyl)ethyl group, 2-(4-fluorophenyl)ethyl group, or 3-phenylpropyl group.

Examples of such compounds represented by formula (6) include those in which Y represents a residue of a compound (Y—OH) comprising at least one alcoholic hydroxyl group (for example at position 9), wherein the compound is selected from the group consisting of:

a) (9S)-1-butyl-9-ethyl-9-hydroxy-1H,12H-pyrano[3",4":6',7']indolizino[1',2':6,5]pyrido[4,3,2-de]quinazoline-2,10,13(3H,9H,15H)-trione;

b) (9S)-9-ethyl-9-hydroxy-1-[2-(4-morpholino)ethyl]-1H,12H-pyrano[3",4":6',7']indolizino[1',2':6,5]pyrido[4,3,2-de]quinazoline-2,10,13(3H,9H,15H)-trione;

c) (9S)-1-[3-(dimethylamino)propyl]-9-ethyl-9-hydroxy-1H,12H-pyrano[3",4":6',7']indolizino[1',2':6,5]pyrido[4,3,2-de]quinazoline-2,10,13(3H,9H,15H)-trione;

d) (9S)-9-ethyl-9-hydroxy-1-phenethyl-1H,12H-pyrano[3",4":6',7']indolizino[1',2':6,5]pyrido[4,3,2-de]quinazoline-2,10,13(3H,9H,15H)-trione;

e) (9S)-9-ethyl-9-hydroxy-1-[2-(pyridin-2-yl)ethyl]-1H,12H-pyrano[3",4":6',7']indolizino[1',2':6,5]pyrido[4,3,2-de]quinazoline-2,10,13(3H,9H,15H)-trione;

f) (9S)-9-ethyl-1-heptyl-9-hydroxy-1H,12H-pyrano[3",4":6',7']indolizino[1',2':6,5]pyrido[4,3,2-de]quinazoline-2,10,13(3H,9H,15H)-trione;

g) (9S)-9-ethyl-9-hydroxy-1-propyl-1H,12H-pyrano[3",4":6',7']indolizino[1',2':6,5]pyrido[4,3,2-de]quinazoline-2,10,13(3H,9H,15H)-trione;

h) (9S)-9-ethyl-9-hydroxy-1-[2-(pyridin-3-yl)ethyl]-1H,12H-pyrano[3",4":6',7']indolizino[1',2':6,5]pyrido[4,3,2-de]quinazoline-2,10,13(3H,9H,15H)-trione;

i) (9S)-9-ethyl-9-hydroxy-1-(3-phenylpropyl)-1H,12H-pyrano[3",4":6',7']indolizino[1',2':6,5]pyrido[4,3,2-de]quinazoline-2,10,13(3H,9H,15H)-trione;

j) (9S)-9-ethyl-9-hydroxy-1-(2-methylpropyl)-1H,12H-pyrano[3",4":6',7']indolizino[1',2':6,5]pyrido[4,3,2-de]quinazoline-2,10,13(3H,9H,15H)-trione;

k) (9S)-9-ethyl-1-hexyl-9-hydroxy-1H,12H-pyrano[3",4":6',7']indolizino[1',2':6,5]pyrido[4,3,2-de]quinazoline-2,10,13(3H,9H,15H)-trione;

l) (9S)-9-ethyl-9-hydroxy-1-pentyl-1H,12H-pyrano[3",4":6',7']indolizino[1',2':6,5]pyrido[4,3,2-de]quinazoline-2,10,13(3H,9H,15H)-trione;

m) (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-2,10,13(3H,9H,15H)-trione;

n) (9S)-1-benzyl-9-ethyl-9-hydroxy-1H,12H-pyrano[3",4":6',7']indolizino[1',2':6,5]pyrido[4,3,2-de]quinazoline-2,10,13(3H,9H,15H)-trione;

o) (9S)-9-ethyl-9-hydroxy-1-(3-methylbutyl)-1H,12H-pyrano[3",4":6',7']indolizino[1',2':6,5]pyrido[4,3,2-de]quinazoline-2,10,13(3H,9H,15H)-trione;

p) (9S)-1,9-diethyl-9-hydroxy-1H,12H-pyrano[3",4":6',7']indolizino[1',2':6,5]pyrido[4,3,2-de]quinazoline-2,10,13(3H,9H,15H)-trione;

q) (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-2,10,13(3H,9H,15H)-trione;

r) (9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-2,10,13(3H,9H,15H)-trione;

s) (9S)-9-ethyl-9-hydroxy-1-(1-methylethyl)-1H,12H-pyrano[3",4":6',7']indolizino[1',2':6,5]pyrido[4,3,2-de]quinazoline-2,10,13(3H,9H,15H)-trione; and t) (9S)-1-(3,3-dimethylbutyl)-9-ethyl-9-hydroxy-1H,12H-pyrano[3",4":6',7']indolizino[1',2':6,5]pyrido[4,3,2-de]quinazoline-2,10,13(3H,9H,15H)-trione.

Among them, the following compounds are more preferred:

a) (9S)-1-butyl-9-ethyl-9-hydroxy-1H,12H-pyrano[3",4":6',7']indolizino[1',2':6,5]pyrido[4,3,2-de]quinazoline-2,10,13(3H,9H,15H)-trione;

b) (9S)-9-ethyl-9-hydroxy-1-phenethyl-1H,12H-pyrano[3",4":6',7']indolizino[1',2':6,5]pyrido[4,3,2-de]quinazoline-2,10,13(3H,9H,15H)-trione;

c) (9S)-9-ethyl-9-hydroxy-1-(2-methylpropyl)-1H,12H-pyrano[3",4":6',7']indolizino[1',2':6,5]pyrido[4,3,2-de]quinazoline-2,10,13(3H,9H,15H)-trione;

d) (9S)-9-ethyl-1-hexyl-9-hydroxy-1H,12H-pyrano[3",4":6',7']indolizino[1',2':6,5]pyrido[4,3,2-de]quinazoline-2,10,13(3H,9H,15H)-trione;

e) (9S)-9-ethyl-9-hydroxy-1-pentyl-1H,12H-pyrano[3",4":6',7']indolizino[1',2':6,5]pyrido[4,3,2-de]quinazoline-2,10,13(3H,9H,15H)-trione;

f) (9S)-9-ethyl-9-hydroxy-1-(3-methylbutyl)-1H,12H-pyrano[3",4":6',7']indolizino[1',2':6,5]pyrido[4,3,2-de]quinazoline-2,10,13(3H,9H,15H)-trione;

g) (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-2,10,13(3H,9H,15H)-trione;

h) (9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-2,10,13(3H,9H,15H)-trione; and i) (9S)-1-(3,3-dimethylbutyl)-9-ethyl-9-hydroxy-1H,12H-pyrano[3",4":6',7']indolizino[1',2':6,5]pyrido[4,3,2-de]quinazoline-2,10,13(3H,9H,15H)-trione.

The aforementioned Y is a compound represented by formula (7) below.

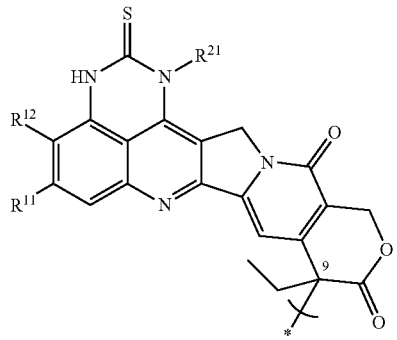

(7)

$R^{11}$, $R^{12}$, and $R^{21}$ are defined as in formulae (4) and (5).

In formula (7), $R^{11}$, and $R^{12}$ are preferably hydrogen atoms.

$R^{21}$ is preferably a hydrogen atom or a C1-C8 alkyl group that may comprise a substituent selected from Group D listed below:

Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring (which may comprise 1 to 3 substituents selected from the group consisting of a hydroxy group, C1-C3 alkoxy group, and halogen atom).

$R^{21}$ is more preferably a phenyl group or C1-C6 alkyl group, and even more preferably a phenyl group, 3-methylbutyl group, or n-pentyl group.

Examples of such compounds represented by formula (7) include those in which Y represents a residue of a compound (Y—OH) comprising at least one alcoholic hydroxyl group (for example at position 9), in which the compound is selected from the group consisting of:

a) (9S)-9-ethyl-9-hydroxy-1-(3-methylbutyl)-1H,12H-pyrano[3",4":6',7']indolizino[1',2':6,5]pyrido[4,3,2-de]quinazoline-2(3H)-thione-10,13(9H,15H)-dione;

b) (9S)-9-ethyl-9-hydroxy-1-phenethyl-1H,12H-pyrano[3",4":6',7']indolizino[1',2':6,5pyrido[4,3,2-de]quinazoline-2(3H)-thione-10,13(9H,15H)-dione; and c) (9S)-9-ethyl-9-hydroxy-1-pentyl-1H,12H-pyrano[3",4":6',7']indolizino[1',2':6,5]pyrido[4,3,2-de]quinazoline-2(3H)-thione-10,13(9H,15H)-dione.

The compounds in which Y is represented by formula (8) are as described below.

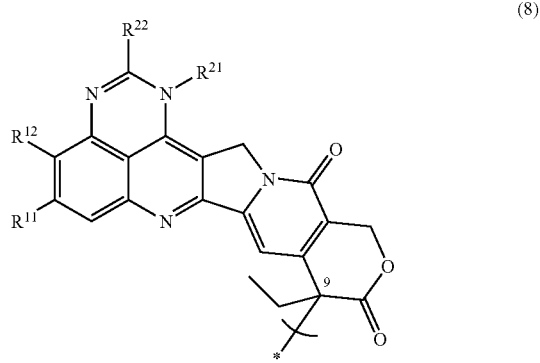

(8)

$R^{11}$, $R^{12}$, $R^{21}$, and $R^{22}$ have the same meanings as $R^{11}$, $R^{12}$, $R^{21}$, and $R^{22}$, respectively, of formulae (4) and (5).

In formula (8), (i) $R^{11}$ is preferably a hydrogen atom.

(ii) $R^{12}$ is preferably a hydrogen atom or a C1-C3 alkyl group, and is more preferably a hydrogen atom or methyl group.

(iii) $R^{21}$ is preferably a hydrogen atom, or a C1-C8 alkyl group that may comprise 1 to 3 substituents selected from Group D described below:

Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring (which may comprise 1 to 3 substituents selected from the group consisting of a hydroxy group, C1-C3 alkoxy group, and halogen atom).

(iv) $R^{21}$ is more preferably a methyl group, ethyl group, n-propyl group, 1-methylethyl group, n-butyl group, 1,1-dimethylethyl group, 2-methylpropyl group, 2,2-dimethylpropyl group, n-pentyl group, 3-methylbutyl group, 2-n-hexyl group, 3,3-dimethylbutyl group, n-heptyl group, n-octyl group, benzyl group, phenethyl group, 2-(dimethylamino)ethyl group, 2-(4-morpholino)ethyl group, 3-(dimethylamino)propyl group, 2-(pyridin-2-yl)ethyl group, 2-(pyridin-3-yl)ethyl group, 2-(4-methoxyphenyl)ethyl group, 2-(4-chlorophenyl)ethyl group, 2-(4-fluorophenyl)ethyl group, or 3-phenylpropyl group.

(v) $R^{22}$ is preferably a hydrogen atom, amino group, C1-C6 alkyl group, C1-C6 alkoxy group, a C1-C6 alkylthio group that may comprise 1 to 3 substituents selected from Group D described below, a mono-C1-C6 alkylamino group that may comprise 1 to 3 substituents selected from Group D described below, or a di-C1-C6 alkyl amino group that may comprise 1 to 3 substituents selected from Group D described below:

Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring (which may comprise 1 to 3 substituents selected from the group consisting of a hydroxy group, C1-C3 alkoxy group, and halogen atom).

(vi) $R^{22}$ is more preferably a hydrogen atom, methyl group, ethyl group, propyl group, hydroxymethyl group, aminomethyl group, (methylamino)methyl group, (dimethylamino)methyl group, chloromethyl group, trifluoromethyl group, phenyl group, 2-pyridyl group, methoxy group, ethoxy group, methylthio group, ethylthio group, methylamino group, butylamino group, or dimethylamino group.

Regarding the above-mentioned (i) to (vi), preferred embodiments can be combined with discretion. Examples of the permitted combinations are (i), (ii), (iii), and (v); (i), (ii), (iii), and (vi); (i), (ii), (iv), and (v); and (i), (ii), (iv), and (vi).

Examples of such compounds represented by formula (8) include those in which Y represents a residue of a compound (Y—OH) comprising at least one alcoholic hydroxyl group (for example at position 9), in which the compound is selected from the group consisting of:

a) (9S)-1-butyl-9-ethyl-9-hydroxy-1H,12H-pyrano[3",4":6',7']indolizino[1',2':6,5]pyrido[4,3,2-de]quinazoline-10,13(9H,15H)-dione;

b) (9S)-9-ethyl-9-hydroxy-1-[2-(4-morpholino)ethyl]-1H,12H-pyrano[3",4":6',7']indolizino[1',2':6,5]pyrido[4,3,2-de]quinazoline-10,13(9H,15H)-dione hydrochloride;

c) (9S)-9-ethyl-9-hydroxy-1-propyl-1H,12H-pyrano[3",4":6',7']indolizino[1',2':6,5pyrido[4,3,2-de]quinazoline-10,13(9H,15H)-dione;

d) (9S)-1-benzyl-9-ethyl-9-hydroxy-1H,12H-pyrano[3",4":6',7']indolizino[1',2':6,5]pyrido[4,3,2-de]quinazoline-10,13(9H,15H)-dione;

e) (9S)-9-ethyl-9-hydroxy-1-phenethyl-1H,12H-pyrano[3",4":6',7']indolizino[1',2':6,5]pyrido[4,3,2-de]quinazoline-10,13(9H,15H)-dione;

f) (9S)-2,9-diethyl-9-hydroxy-1-phenethyl-1H,12H-pyrano[3",4":6',7']indolizino[1',2':6,5]pyrido[4,3,2-de]quinazoline-10,13(9H,15H)-dione;

g) (9S)-9-ethyl-9-hydroxy-1-(3-phenylpropyl)-1H,12H-pyrano[3",4":6',7']indolizino[1',2':6,5]pyrido[4,3,2-de]quinazoline-10,13(9H,15H)-dione;

h) (9S)-9-ethyl-9-hydroxy-1-(3-methylbutyl)-1H,12H-pyrano[3",4":6',7']indolizino[1',2':6,5pyrido[4,3,2-de]quinazoline-10,13(9H,15H)-dione;

i) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

j) (9S)-2,9-diethyl-9-hydroxy-1-(2-methylpropyl)-1H,12H-pyrano[3",4":6',7']indolizino[1',2':6,5]pyrido[4,3,2-de]quinazoline-10,13(9H,15H)-dione;

k) (9S)-9-ethyl-1-heptyl-9-hydroxy-1H,12H-pyrano [3",4":6',7']indolizino[1',2':6,5]pyrido[4,3,2-de]quinazoline-10,13(9H,15H)-dione;

l) (9S)-9-ethyl-9-hydroxy-1-methyl-1H,12H-pyrano[3",4":6',7']indolizino[1',2':6,5]pyrido[4,3,2-de]quinazoline-10,13(9H,15H)-dione;

m) (9S)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione;

n) (9S)-9-ethyl-1-hexyl-9-hydroxy-1H,12H-pyrano[3",4":6',7']indolizino[1',2':6,5]pyrido[4,3,2-de]quinazoline-10,13(9H,15H)-dione;

o) (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione;

p) (9S)-1,9-diethyl-9-hydroxy-1H,12H-pyrano[3",4":6',7']indolizino[1',2':6,5]pyrido[4,3,2-de]quinazoline-10,13(9H,15H)-dione;

q) (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-10,13(9H,15H)-dione;

r) (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-10,13(9H,15H)-dione;

s) (9S)-9-ethyl-1-[2-(4-fluorophenyl)ethyl]-9-hydroxy-1H,12H-pyrano[3",4":6',7']indolizino[1',2':6,3,2-de]quinazoline-10,13(9H,15H)-dione;

t) (9S)-9-ethyl-1-[2-(4-fluorophenyl)ethyl]-9-hydroxy-2-methyl-1H,12H-pyrano[3",4":6',7']indolizino[1',2':6,5]pyrido[4,3,2-de]quinazoline-10,13(9H,15H)-dione;

u) (9S)-9-ethyl-9-hydroxy-1-(1-methylethyl)-1H,12H-pyrano[3",4":6',7']indolizino[1',2':6,5]pyrido[4,3,2-de]quinazoline-10,13(9H,15H)-dione.

v) (9S)-1-(3,3-dimethylbutyl)-9-ethyl-9-hydroxy-1H,12H-pyrano[3",4":6',7']indolizino[1',2':6,5]pyrido[4,3,2-de]quinazoline-10,13(9H,15H)-dione;

w) (9S)-9-ethyl-9-hydroxy-2-methoxy-1-(3-methylbutyl)-1H,12H-pyrano[3",4":6',7']indolizino[1',2':6,5]pyrido[4,3,2-de]quinazoline-10,13(9H,15H)-dione;

x) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

y) (9RS)-9-ethyl-9-hydroxy-4-methyl-1-pentyl-1H,12H-pyrano[3",4":6',7']indolizino[1',2':6,5]pyrido[4,3,2-de]quinazoline-10,13(9H,15H)-dione;

z) (9S)-9-ethyl-9-hydroxy-1-(2-hydroxyethyl)-1H,12H-pyrano[3",4":6',7']indolizino[1',2':6,5]pyrido[4,3,2-de]quinazoline-10,13(9H,15H)-dione;

aa) (9S)-9-ethyl-9-hydroxy-1-(2-hydroxyethyl)-2-methyl-1H,12H-pyrano[3",4":6',7']indolizino[1',2':6,5]pyrido[4,3,2-de]quinazoline-10,13(9H,15H)-dione;

bb) (9S)-9-ethyl-9-hydroxy-2-methyl-1-pentyl-1H,12H-pyrano[3",4":6',7']indolizino[1',2':6,5pyrido[4,3,2-de]quinazoline-10,13(9H,15H)-dione;

cc) (9S)-2,9-diethyl-9-hydroxy-1-pentyl-1H,12H-pyrano[3",4":6',7']indolizino[1',2':6,5]pyrido[4,3,2-de]quinazoline-10,13(9H,15H)-dione;

dd) (9S)-9-ethyl-9-hydroxy-1-pentyl-2-propyl-1H,12H-pyrano[3",4":6',7']indolizino[1',2':6,5]pyrido[4,3,2-de]quinazoline-10,13(9H,15H)-dione;

ee) (9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione;

ff) (9S)-9-ethyl-9-hydroxy-2-hydroxymethyl-1-(2-methylpropyl)-1H,12H-pyrano[3",4":6',7']indolizino[1',2':6,5]pyrido[4,3,2-de]quinazoline-10,13(9H,15H)-dione;

gg) (9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione;

hh) (9S)-2-chloromethyl-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

ii) (9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H,15H)-dione;

jj) (9S)-9-ethyl-9-hydroxy-1-pentyl-2-trifluoromethyl-1H,12H-pyrano[3",4":6',7']indolizino[1',2':6,5]pyrido[4,3,2-de]quinazoline-10,13(9H,15H)-dione;

kk) (9S)-9-ethyl-9-hydroxy-1-(3-methylbutyl)-2-methylthio-1H,12H-pyrano[3",4":6',7']indolizino[1',2':6,5]pyrido[4,3,2-de]quinazoline-10,13(9H,15H)-dione;

ll) (9S)-9-ethyl-2-ethylthio-9-hydroxy-1-(3-methylbutyl)-1H,12H-pyrano[3",4":6',7']indolizino[1',2':6,5]pyrido[4,3,2-de]quinazoline-10,13(9H,15H)-dione;

mm) (9S)-2-(dimethylamino)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione hydrochloride; and nn) (9S)-2-(butylamino)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione hydrochloride.

Among the camptothecins indicated above, particularly preferred examples are the following compounds:

4(S)-ethyl-4-hydroxy-1H-pyrano[3',4':6,7]indolizino[1,2-b]quinoline-3,14(4H,12H)-dione(camptothecin);

5(R)-ethyl-9,10-difluoro-1,4,5,13-tetrahydro-5-hydroxy-3H,15H-oxepino[3',4':6,7]indolizino[1,2-b]quinoline-3,15-dione (BN-80915);

o) (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione;

bb) (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)-dione; and ee) (9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione.

Azole Antifungal Agents

When Y is a residue derived from azole antifungal agents, examples of the azole antifungal agents include triazoles.

Examples of such azole antifungal agents include at least one compound selected from the group consisting of:

(2R,3R)-3-{4-(4-cyanophenyl)thiazol-2-yl}-2-(2,5-difluorophenyl)-1-(1H-1,2,4-triazol-1-yl)-butan-2-ol;

2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone;

(+)-2-(2,4-difluorophenyl)-3-methyl-1-(1H-1,2,4-triazol-1-yl)-3-(6-(1H-1,2,4-triazol-1-yl)pyridazin-3-ylthio)butan-2-ol;

(2R)-2-(2,4-difluorophenyl)-1-[3-[(E)-4-(2,2,3,3-tetrafluoropropoxy)-styryl]-(1,2,4-triazol-1-yl)-3-(1,2,4-triazol-1-yl)]propan-2-ol;

dl-threo-2-(2,4-difluorophenyl)-3-methyl-sulfonyl-1-(1H-1,2,4-triazol-1-yl)-butan-2-ol;

(−)-4-[4-[4-[4-[[5-(2,4-difluorophenyl)-5-(1H-1,2,4-triazol-1-ylmethyl)tetrahydrofuran-3-yl]methoxy]phenyl]piperazinyl]phenyl]-2[(1S,2S)-1-ethyl-2-hydroxypropyl]-3H-1,2,4-triazol-3-one;

(2R,3R)-3-[4-(4-cyanophenyl)thiazol-2-yl]-2-(2,4-difluorophenyl)-1-(1H-1,2,4-triazol-1-yl)-butan-2-ol;

3-methyl-3-methylthio-1-(1,2,4-triazol-1-yl)-2-(trifluoromethylphenyl)-butan-2-ol, (2R,3R)-3-[4-(4-cyanophenyl)thiazol-2-yl]-1-(1H-1,2,4-triazol-1-yl)-2-(2,4,5-trifluorophenyl)-butan-2-ol; and (2R,3R)-3-[4-(4-cyanophenyl)thiazol-2-yl]-2-(3-fluorophenyl)-1-(1H-1,2,4-triazol-1-yl)-butan-2-ol.

Among the water-soluble prodrugs of the present invention, examples of compounds that are derived from camptothecins include the following:

(a) (9S)-9-ethyl-9-{[methyl-(2-methylamino-ethyl)-amino]-acetoxy}-1-pentyl-1H,12H-pyrano[3",4":6',7']indolizino[1',2':6,5]pyrido[4,3,2-de]quinazoline-10,13(9H,15H)-dione;

(b) (9S)-9-ethyl-9-(glycyl-sarcosyloxy)-1-pentyl-1H,12H-pyrano[3",4":6',7']indolizino[1',2':6,5]pyrido[4,3,2-de]quinazoline-10,13(9H,15H)-dione;

(c) (9S)-9-{[(2-amino-ethyl)-methyl-amino]-acetoxy}-9-ethyl-1-pentyl-1H,12H-pyrano[3",4":6',7']indolizino[1',2':6,5]pyrido[4,3,2-de]quinazoline-10,13(9H,15H)-dione;

(d) (9S)-9-ethyl-9-(sarcosyl-sarcosyloxy)-1-pentyl-1H,12H-pyrano[3",4":6',7']indolizino[1',2':6,5]pyrido[4,3,2-de]quinazoline-10,13(9H,15H)-dione;

(e) (9S)-9-[2-(2-aminoethanesulfonyl)ethoxycarbonyloxy]-9-ethyl-1-pentyl-1H,12H-pyrano[3",4":6',7']indolizino[1',2':6,5]pyrido[4,3,2-de]quinazoline-10,13(9H,15H)-dione;

(f) (aminoacetyl-methyl-amino)-acetic acid (S)-4-ethyl-3,13-dioxo-3,4,12,13-tetrahydro-1H-2-oxa-6,12a-diazadibenzo[b,h]fluoren-4-yl ester;

(g) (9S)-9-{2-[(R-2-amino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione;

(h) (9S)-9-{2-[(R-2-amino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione;

(i) (9S)-9-ethyl-9-(N-methylalanyl-N-methylalanyloxy)-1-pentyl-1H,12H-pyrano[3",4":6',7']indolizino[1',2':6,5]pyrido[4,3,2-de]quinazoline-10,13(9H,15H)-dione; and (j) (9S)-9-ethyl-9-(sarcosyl-N-methylalanyloxy)-1-pentyl-1H,12H-pyrano[3",4":6',7']indolizino[1',2':6,5]pyrido[4,3,2-de]quinazoline-10,13(9H,15H)-dione.

The water-soluble prodrugs of the present invention are preferably the compounds of (b), (d), (e), and (h), and more preferably compounds of (b) and (e).

BEST MODE FOR CARRYING OUT THE INVENTION

Figure 1:
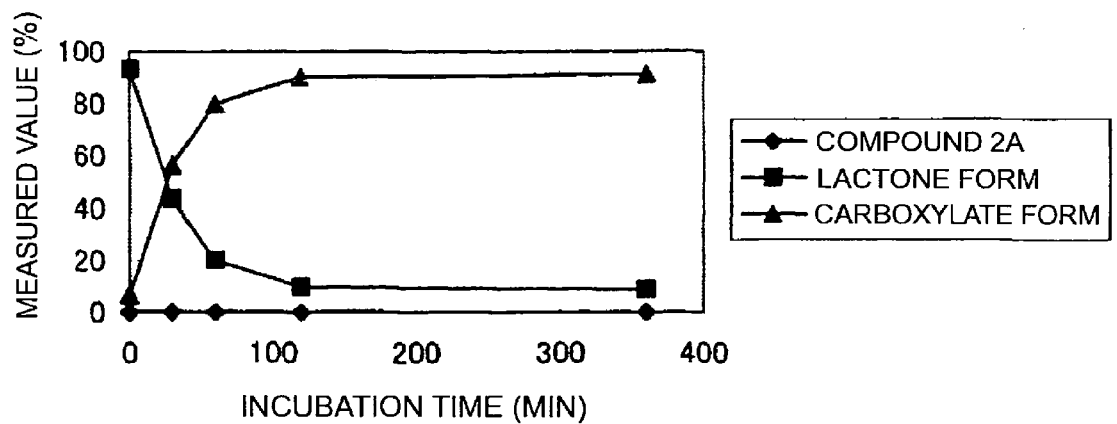
FIG. 1 is a graph showing percent changes in the conversion of compound 2A into the lactone form and the carboxylate form in human serum over time.
Figure 2:
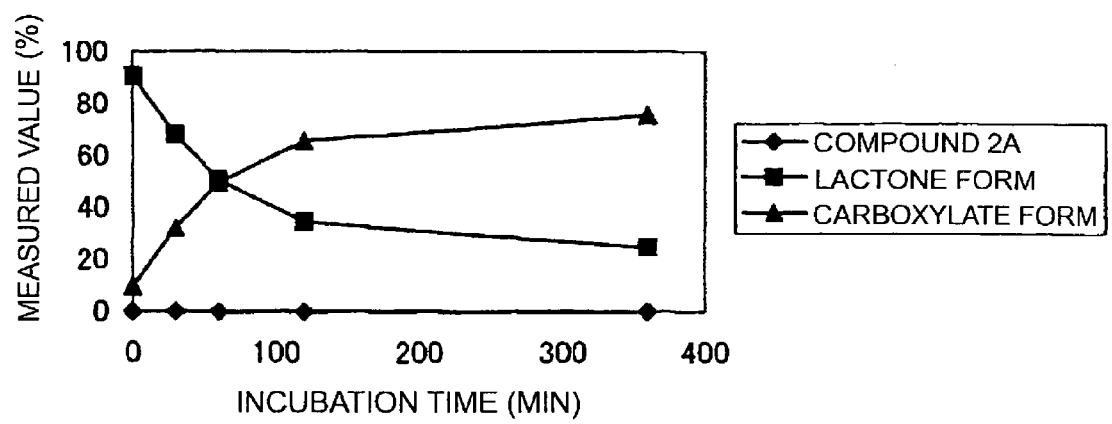
FIG. 2 is a graph showing percent changes in the conversion of compound 2A into the lactone form and the carboxylate form in mouse serum over time.
Figure 3:
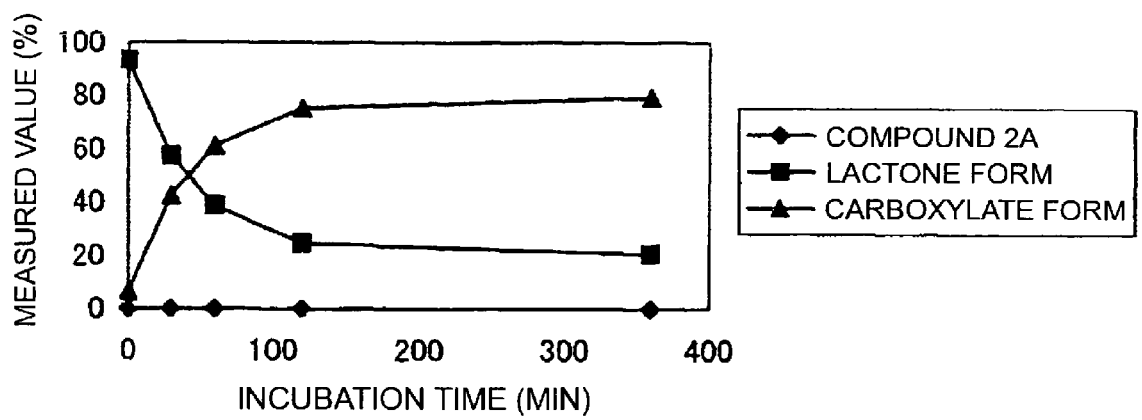
FIG. 3 is a graph showing percent change in the conversion of compound 2A into the lactone form and the carboxylate form in monkey serum over time.
Figure 4:
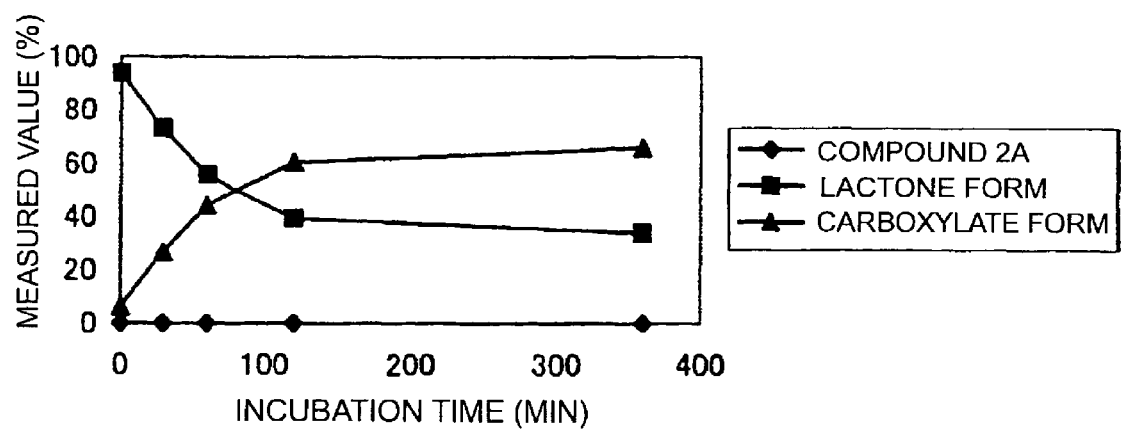
FIG. 4 is a graph showing percent changes in the conversion of compound 2A into the lactone form and the carboxylate form in dog serum over time.

In the present invention, the compounds represented by formula (1) may be produced using the following methods, but the methods for producing the compounds of this invention are not to be construed as being limited thereto. Although the water-soluble prodrugs of this invention are all novel compounds, they can be produced by well-known chemical methods using commercially available raw materials, or those synthesized by standard methods, as necessary.

In the following production methods, $R^1$, $R^2$, $R^3$, $R^4$, X, Y, $R^5$, n, $R^7$, and $R^8$ have the same meaning as $R^1$, $R^2$, $R^3$, $R^4$, X, Y, $R^5$, n, $R^7$, and $R^8$, respectively, as defined in formulas (2), (3), and (9). $P^1$ represents an amino protecting group, $P^2$ represents a residue from a carbonylating reagent, and Hal represents a halogen atom (i.e., a chlorine atom, bromine atom, or iodine atom).

Reaction Process 1-1

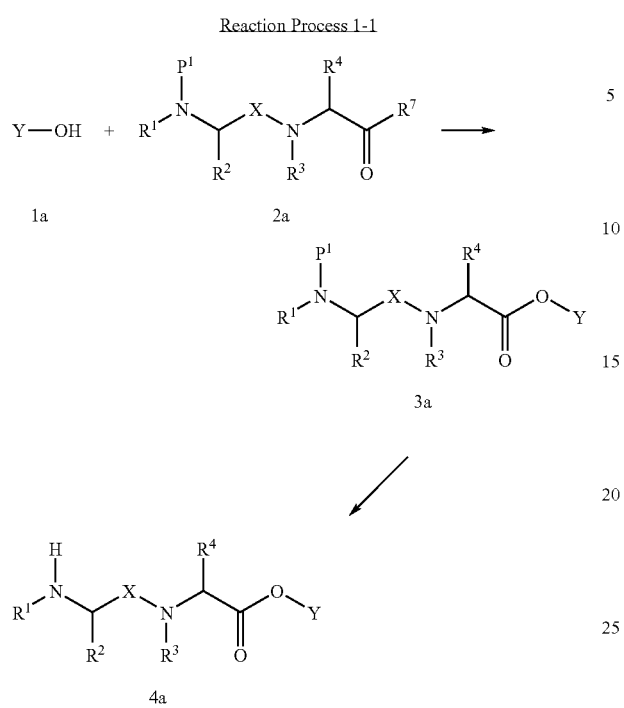

Reaction Process 1-2

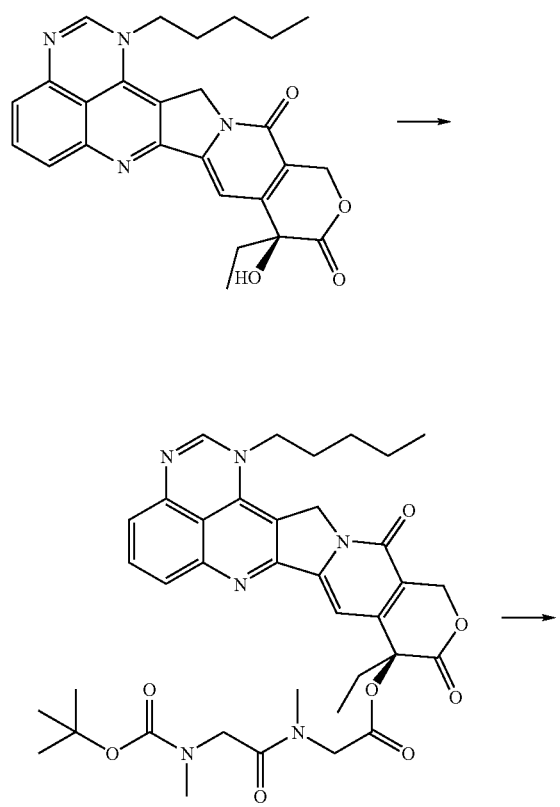

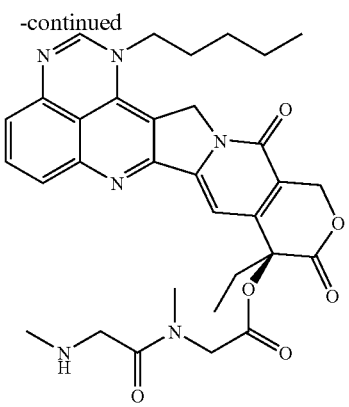

<Reaction Process 1>

Reaction Process 1 shows an example of the production of a water-soluble prodrug comprising a tertiary amino group in its solubilizing side chain.

The water-soluble prodrug represented by formula (2) can be obtained easily by, for example, acylation of a secondary or tertiary hydroxyl group present in Y—OH.

Preparation of Compound 3a

As indicated in Reaction Process 1-1, ester (3a) can be obtained by reacting a secondary or tertiary alcohol (1a) with a suitable compound (2a) in an appropriate solvent, in the presence of a coupling agent. Examples of compound 2a include a carboxylic acid ($R^7$=OH), a carboxylate ($R^7$=$OR^8$), and a acyl halide compound ($R^7$=halogen atom: chlorine atom or such), with carboxylic acid being the preferred one.

Y—OH can be obtained commercially or by known methods (WO03/045952, WO03/043631, etc.).

When compound (2a) is a dipeptide (X=CO) carboxylic acid, or a peptide derivative (X=$CH_2$), the amino acid derivative used to prepare such a compound (2a) is commercially available, or it can be prepared by known methods described in the literature (for example, J. Am. Chem. Soc. 2000, 122, 762-766; J. Org. Chem, 1998, 5240; Tetrahedron Asymmetry, 1995, 1741; Tetrahedron Asymmetry, 1998, 4249). The carboxylic acid can be converted into a carboxylate ester ($R^7$=$OR^8$) or a acyl halide compound ($R^7$=halogen atom) by known methods.

Furthermore, the dipeptide derivative can be prepared by standard peptide chemistry well known to those skilled in the art [see, "The Practice of Peptide Synthesis" by M. Bodansky and A. Bodansky, 2nd edition, 1994 (Springer-Verlag)].

Examples of solvents used in the above coupling reaction include methylene chloride, ethyl acetate, tetrahydrofuran, acetonitrile, chloroform, dioxane, and dimethylformamide.

Examples of the coupling agents include 1-ethyl-3-(3-dimethylaminopropyl)-carbodiimide hydrochloride, dicyclohexylcarbodiimide, BOP, HBTU, TNTU, PyBroP™, PyBOP™, TBTU, TSTU, and HOBt [see, The Combinatorial Chemistry Catalog, February, 1997; Novabiochem., for commercially available coupling reagents].

Preparation of Compound 4a

While preparation of compound 4a depends on the type of the corresponding carboxylic acid, a corresponding carboxylic acid (2a) with a protected amino group is usually preferred. The coupling reaction is followed by removal of the protecting group from compound (3a), to give the water-soluble prodrug represented by compound (4a).

The obtained water-soluble prodrug comprising an amino protecting group is deprotected, for example, as shown in Process 1-2.

The coupling reaction and selection of the amino protecting group $P^1$ in Processes 1-1 and 1-2 can be performed suitably using known methods (see, "The Practice of Peptide Synthesis" by M. Bodansky and A. Bodansky, 2nd edition, 1994 (Springer-Verlag); "Protective Groups in Organic Synthesis" by Theodora Greene, 1999 (Wiley-Interscience)).

Examples of amino protecting groups include the following:

Carbamates (in the Form of $R^1R^2NX$)

a methyloxycarbonyl group, 9-fluorenylmethyloxycarbonyl group, 9-(2-sulfo)fluorenylmethyloxycarbonyl group, 9-(2,7-dibromo)fluorenylmethyloxycarbonyl group, 4-methoxyphenacyloxycarbonyl group, ethyloxycarbonyl group, 2,2,2-trichloroethyloxycarbonyl group, 2-trimethylsilylethyloxycarbonyl group, phenethyloxycarbonyl group, 1-(1-adamantyl)-1-methylethyloxycarbonyl group, 2-chloroethyloxycarbonyl group, 2-bromoethyloxycarbonyl group, 2-iodoethyloxycarbonyl group, 2,2-dichloroethyloxycarbonyl group, 2,2-dibromoethyloxycarbonyl group, 2,2,2-trichloroethyloxycarbonyl group, 2,2,2-tribromoethyloxycarbonyl group, 1,1-dimethyl-2-chloroethyloxycarbonyl group, 1,1-dimethyl-2-bromoethyloxycarbonyl group, 1,1-dimethyl-2,2-dibromoethyloxycarbonyl group, 1,1-dimethyl-2,2,2-trichloroethyloxycarbonyl group, 1-methyl-1-(4-biphenylyl)ethyloxycarbonyl group, 1-(3,5-di t-butylphenyl)-1-methylethyloxycarbonyl group, 2-(2'-pyridyl)ethyloxycarbonyl group, 2-(4'-pyridyl)ethyloxycarbonyl group, 2-(N,N-dicyclohexylcarboxamide)ethyloxycarbonyl group, t-butyloxycarbonyl group, 1-adamantyloxycarbonyl group, vinyloxycarbonyl group, allyloxycarbonyl group, 1-isopropylallyloxycarbonyl group, cinnamyloxycarbonyl group, 4-nitrocinnamyloxycarbonyl group, 8-quinolyloxycarbonyl group, piperidinyloxycarbonyl group, benzyloxycarbonyl group, p-methoxybenzyloxycarbonyl group, p-nitrobenzyloxycarbonyl group, p-chlorobenzyloxycarbonyl group, p-bromobenzyloxycarbonyl group, p-cyanobenzyloxycarbonyl group, o-nitrobenzyloxycarbonyl group, 2,4-dichlorobenzyloxycarbonyl group, 4-methylsulfinylbenzyloxycarbonyl group, 9-anthrylmethyloxycarbonyl group, diphenylmethyloxycarbonyl group, 2-methylthioethyloxycarbonyl group, 2-methylsulfonylethyloxycarbonyl group, 2-(p-toluenesulfonyl)ethyloxycarbonyl group, [2-(1,3-dithianyl)]methyloxycarbonyl group, 4-methylthiophenyloxycarbonyl group, 2,4-dimethylthiophenyloxycarbonyl group, 2-phosphinoethyloxycarbonyl group, 2-triphenylphosphonioisopropyloxycarbonyl group, 1,1-dimethyl-2-cyanoethyloxycarbonyl group, m-chloro-p-acetylbenzyloxycarbonyl group, p-(dihydroxyboryl)benzyloxycarbonyl group, 5-benzisoxazolylmethyloxycarbonyl group, 2-(trifluoromethyl)-6-chromonylmethyloxycarbonyl group, m-nitrophenyloxycarbonyl group, 3,5-dimethoxybenzyloxycarbonyl group, 3,4-dimethoxy-6-nitrobenzyloxycarbonyl group, and phenyl(o-nitrophenyl)methyloxycarbonyl group;

Urea Types a piperidinylcarbonyl group, p-toluenesulfonylaminocarbonyl group, and phenylaminothiocarbonyl group;

Others a t-amyloxycarbonyl group, benzylthiocarbonyl group, cyclobutyloxycarbonyl group, cyclopentyloxycarbonyl group, cyclohexyloxycarbonyl group, cyclopropylmethyloxycarbonyl group, p-decyloxybenzyloxycarbonyl group, diisopropylmethyloxycarbonyl group, 2,2-dimethoxycarbonylvinyloxycarbonyl group, o-(N,N-dimethylcarboxamide)benzyloxycarbonyl group, 1,1-dimethyl-3-(N,N-dimethylcarboxamide)propyloxycarbonyl group, 1,1-dimethylpropynyloxycarbonyl group, di(2-pyridyl)methyloxycarbonyl group, 2-furanylmethyloxycarbonyl group, isobornyloxycarbonyl group, isobutyloxycarbonyl group, isonicotinyloxycarbonyl group, p-(p'-methoxyphenylazo)benzyloxycarbonyl group, 1-methylcyclobutyloxycarbonyl group, 1-methylcyclohexyloxycarbonyl group, 1-methyl-1-cyclopropylmethyloxycarbonyl group, 1-methyl-1-(3,5-dimethoxyphenyl)ethyloxycarbonyl group, 1-methyl-1-(p-phenylazophenyl)ethyloxycarbonyl group, 1-methyl-1-phenylethyloxycarbonyl group, 1-methyl-1-(4-pyridyl)ethyloxycarbonyl group, p-(phenylazo)benzyloxycarbonyl group, 2,4,6-tri-t-butylphenyloxycarbonyl group, 4-(trimethylammonium)benzyloxycarbonyl group, and 2,4,6-trimethylbenzyloxycarbonyl group; and Amides (in the Form of $R^1R^2NX$)

a formyl group, acetyl group, chloroacetyl group, trichloroacetyl group, trifluoroacetyl group, phenylacetyl group, 3-phenylpropionyl group, picolinoyl group, benzoyl group, p-phenylbenzoyl group, o-nitrophenylacetyl group, o-nitrophenoxyacetyl group, acetoacetyl group, (N-dithiobenzyloxycarbonylamino)acetyl group, 3-(p-hydroxyphenyl)propionyl group, 3-(o-nitrophenyl)propionyl group, 2-methyl-2-(o-nitrophenoxy)propionyl group, 2-methyl-2-(o-phenylazophenoxy)propionyl group, 4-chlorobutyryl group, 3-methyl-3-nitrobutyryl group, o-nitrocinnamoyl group, o-nitrobenzoyl group, and o-(benzoyloxymethyl)benzoyl group.

Removal of the amino protecting group after a coupling reaction can be performed by methods well known to those skilled in the art, such as methods that use trifluoroacetic acid for the removal of a Boc group, piperidine for the removal of an Fmoc group, and tetrabutylammonium fluoride for the removal of 2-(trimethylsilyl)ethoxycarbonyl (Teoc), trimethylsilylethyl and tert-butyldimethylsilyl groups, and catalytic hydrogenation for the removal of a Cbz group.

Reaction Process 2-1

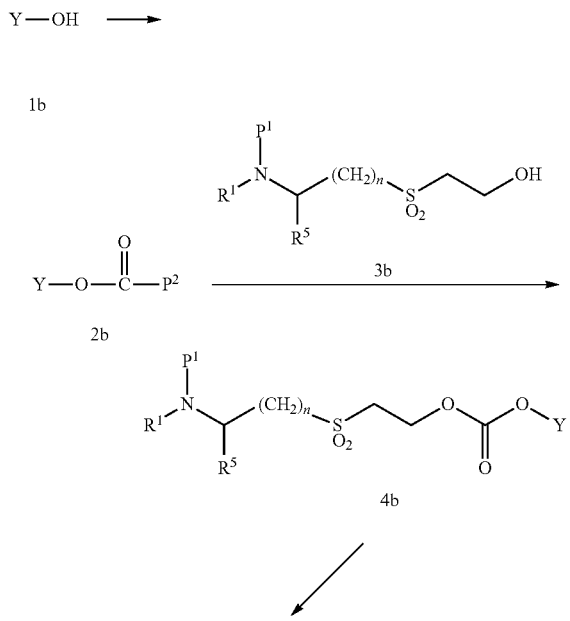

-continued

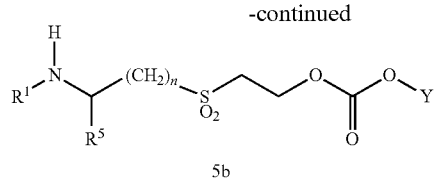

5b

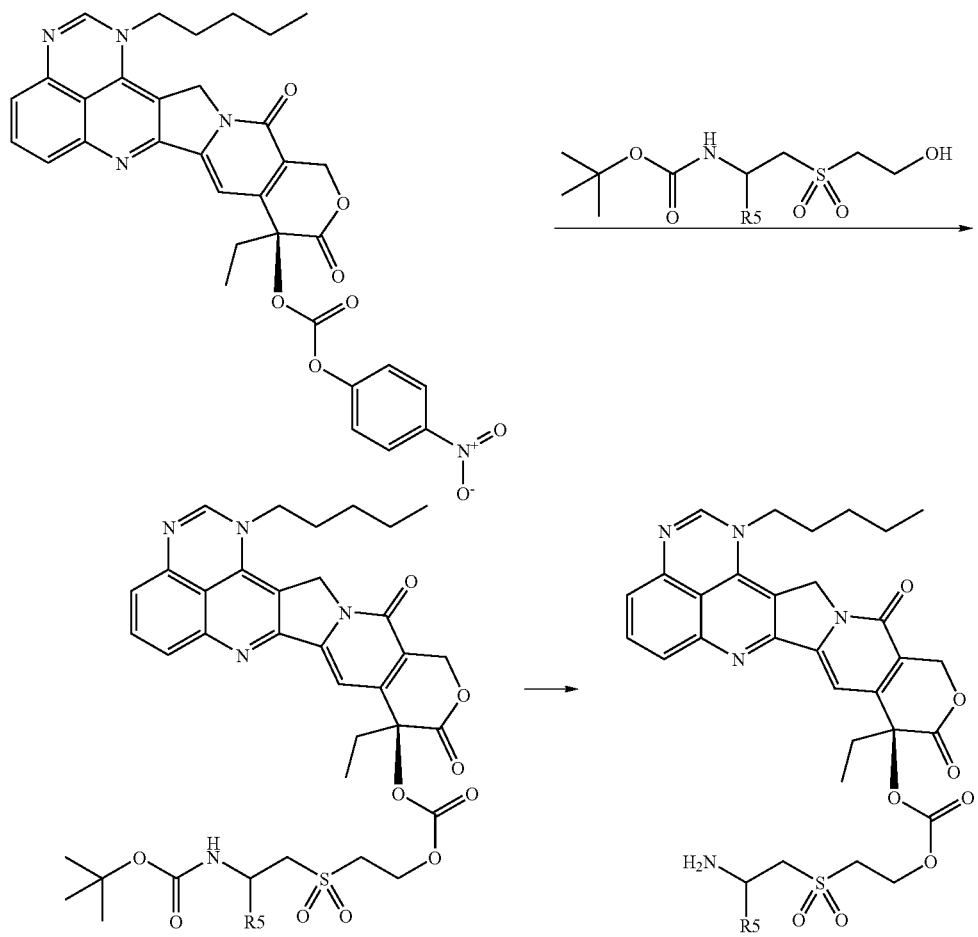

<Reaction Process 2>

Reaction Process 2 shows an example of the method for producing water-soluble prodrugs whose solubilizing side chain comprises a sulfonyl group.

Preparation of Compound 2b

First, alcohol (1b) is carbonylated to produce compound (2b). Carbonylation of the hydroxyl group is accomplished by reacting alcohol (1b) with an appropriate carbonylating agent in an appropriate solvent.

Examples of a solvent that may be used include methylene chloride, ethyl acetate, tetrahydrofuran, acetonitrile, chloroform, dioxane, and dimethylformamide.

Examples of a carbonylating agent that may be used include p-nitrophenyl chloroformate, carbonyldiimidazole, and phosgenes.

Usually, the reaction can be performed at approximately −10° C. to 25° C., for approximately 1 to 24 hours.

Preparation of Compound 3b

Compound 3b comprising a solubilizing side chain can be prepared by a known method (Tetrahedron (1999), 55: 6623-6634).

Protection of the amino group in alcohol (3b) can be performed suitably using known methods (see, The Practice of Peptide Synthesis, M. Bodansky, and A. Bodansky/2nd edition, 1994 (Springer-Verlag)).

Preparation of Compound 4b

Next, alcohol (3b) comprising a corresponding protected amino group can be reacted with carbonylated compound (2b) in the presence of an appropriate solvent to give an amino-group-protected carbonate (4b).

Examples of a solvent that may be used include methylene chloride, ethyl acetate, tetrahydrofuran, acetonitrile, chloroform, dioxane, and dimethylformamide.

Usually, the reaction can be performed at approximately 15° C. to 25° C., for approximately 2 to 48 hours.

Preparation of Compound 5b

By removing the amino protecting group of carbonate (4b) by known methods, compound (5b) can be obtained. Removal of the amino group can be performed using known methods, as shown in Reaction 1. Examples include the use of trifluoroacetic acid for the removal of a Boc group, piperidine for the removal of an Fmoc group, and tetrabutylammonium fluoride for the removal of 2-(trimethylsilyl)ethoxycarbonyl (Teoc), trimethylsilylethyl and tert-butyldimethylsilyl groups, and catalytic hydrogenation for the removal of a Cbz group.

Reaction 2-2 shows a specific example of such.

Reaction 3-1
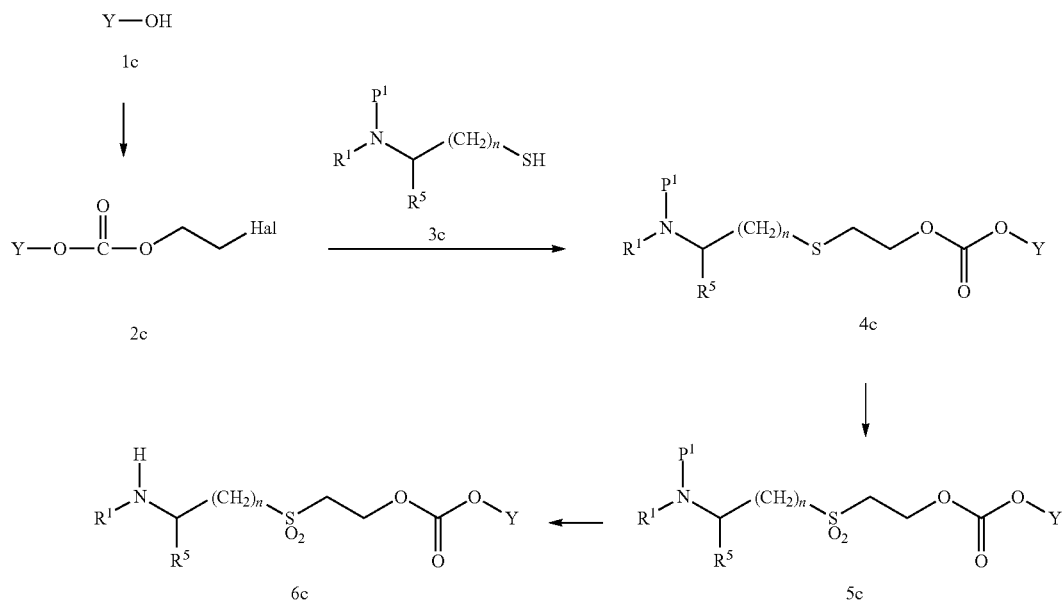
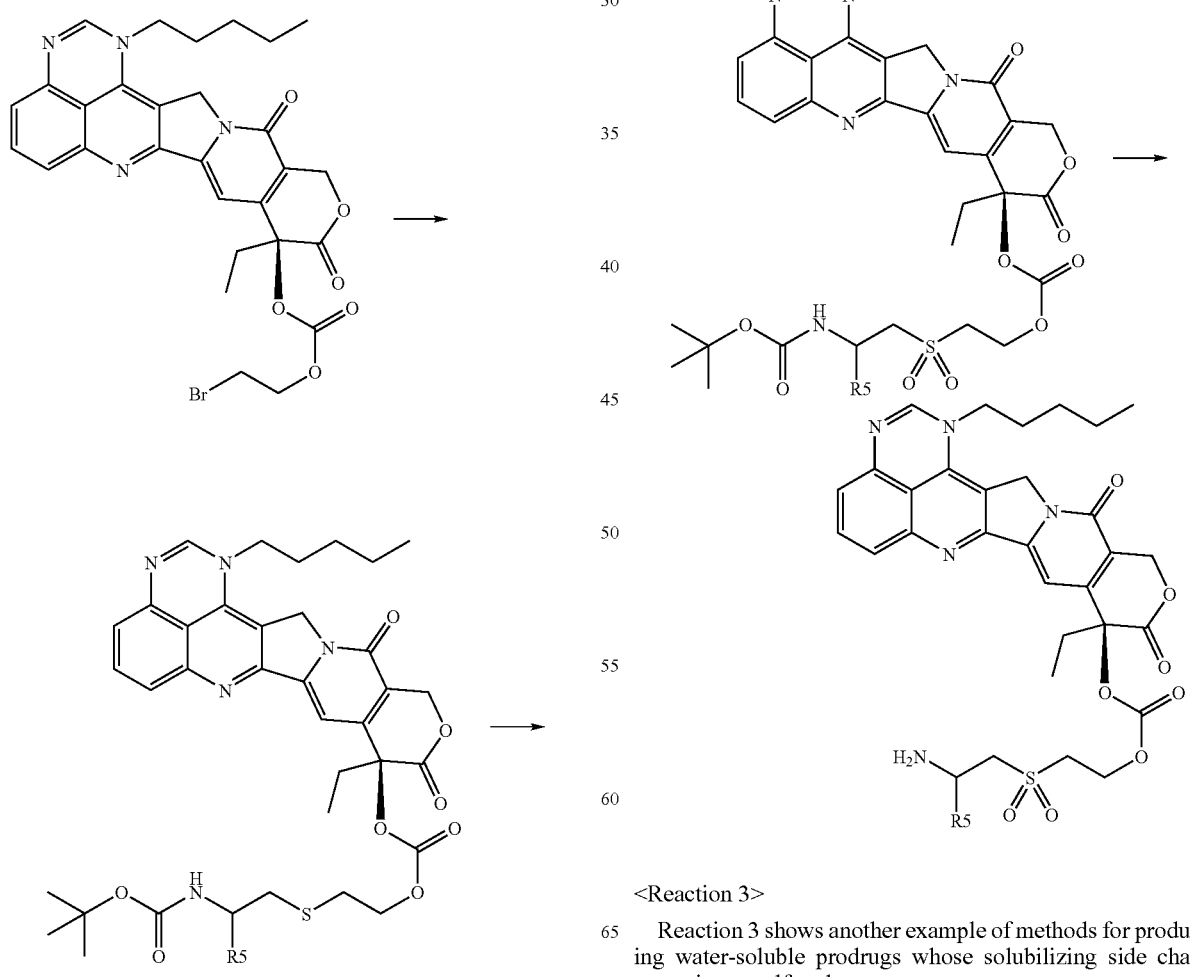
<Reaction 3>
Reaction 3 shows another example of methods for producing water-soluble prodrugs whose solubilizing side chain comprises a sulfonyl group.

Preparation of Compound 2c

First, a 2-halogenated ethyl carbonate (2c) is prepared from an alcohol (1c).

Conversion of the hydroxyl group of alcohol (1c) into a 2-halogenated ethyl carbonate (2) can be performed by reaction with a commercially available chloroformate in an appropriate solvent.

Examples of a solvent that may be used include methylene chloride, ethyl acetate, tetrahydrofuran, acetonitrile, chloroform, dioxane, and dimethylformamide.

Usually, the reaction can be performed at approximately −10° C. to 25° C., for approximately 1 to 24 hours.

Preparation of Compound 3c

Thiol compound 3c comprising a solubilizing side chain can be prepared from a commercially available product, or it may be prepared by known methods (Tetrahedron, 1999, 55, 6623-6634; and J. Org. Chem. 1995, 60, 8105-8109).

Protection of the amino group in thiol compound (3c) can be performed suitably using known methods (see, The Practice of Peptide Synthesis, M. Bodansky, and A. Bodansky/2nd edition, 1994 (Springer-Verlag)).

Preparation of Compound 4c

Next, amino-group-protected carbonate (4c) can be obtained by reacting the corresponding amino-group-protected thiol compound (3c) with 2-halogenated ethyl carbonate (2c) in an appropriate solvent, under the presence of a base.

Examples of a solvent that may be used include methylene chloride, ethyl acetate, tetrahydrofuran, acetonitrile, chloroform, dioxane, dimethylformamide, methanol, and ethanol.

Examples of a base that may be used include triethylamine, diisopropylethylamine, potassium carbonate, and sodium carbonate.

Usually, the reaction can be performed at approximately 15° C. to 100° C., for approximately 1 to 24 hours.

Preparation of Compound 5c

Furthermore, compound 5c can be obtained using known methods by reacting compound 4c with a peroxidizing reagent.

Examples of a peroxidizing reagent that may be used include oxone, hydrogen peroxide, and m-chloroperbenzoic acid.

Usually, the reaction can be performed at approximately −10° C. to 100° C., for approximately 1 to 24 hours.

Preparation of Compound 6c

Compound (6c) can be obtained by removing the amino protecting group of compound 5c using known methods. Removal of the amino protecting group can be performed using known methods, as in Reaction 1. Examples include the use of trifluoroacetic acid for the removal of a Boc group, piperidine for the removal of an Fmoc group, and tetrabutylammonium fluoride for the removal of 2-(trimethylsilyl)ethoxycarbonyl (Teoc), trimethylsilylethyl and tert-butyldimethylsilyl groups, and removal of a Cbz group by catalytic hydrogenation.

Reaction 3-2 Shows a Specific Example of Such.

The above illustrates an example of the methods for producing the water-soluble prodrugs of the present invention. The isolation and purification of the compounds of interest indicated in Reactions 1 to 3 can be performed by applying standard chemical operations, such as extraction, concentration, solvent removal, crystallization, filtration, recrystallization, and various chromatographies.

The water-soluble prodrugs of the present invention represented by formulas (1) to (8), and pharmaceutically acceptable salts, hydrates, and solvates thereof, include all stereoisomers of the water-soluble prodrugs mentioned above (for example, enantiomers, and diastereomers including cis and trans geometric isomers), racemates of the isomers, and other mixtures. The water-soluble prodrugs of the present invention represented by formulas (1) to (8) include stereoisomers, in particular.

Water-soluble prodrugs of the present invention represented by formulas (1) to (8), and pharmaceutically acceptable salts, hydrates, or solvates thereof, may exist in different tautomeric forms, such as the keto and enol forms, and the imine and enamine forms, or as mixtures of both. Tautomers exist as mixtures of a tautomeric set in solution. In solid form, usually one of the tautomers predominates. The present invention includes all tautomers of the compounds of this invention, including cases where only one of the tautomers is described.

Furthermore, the present invention includes atropisomers of this invention. Atropisomers refer to water-soluble prodrugs represented by formulas (1) to (8) that can be resolved into isomers with restricted rotation.

These isomers can be isolated by standard methods based on their differences in physicochemical properties. For example, racemic compounds can be resolved into sterically pure isomers by standard optical resolution methods, such as optical resolution by derivatization to diastereomeric salts using an optically active acid such as tartaric acid. Diastereomeric mixtures can be resolved by using fractional crystallization, and various chromatographic techniques (for example, thin layer chromatography, column chromatography, and gas chromatography).

When the water-soluble prodrugs of the present invention can be obtained in the free form, they can be formed into salts, or converted to hydrates or solvates thereof, by standard methods.

Alternatively, when the compounds of the present invention are obtained as salts, hydrates, or solvates, these compounds can be converted to their free form by standard methods.

The water-soluble prodrugs of the present invention represented by formulas (1) to (8), and their pharmaceutically acceptable salts, hydrates, and solvates show good water solubility, and since they are rapidly converted into the active form by chemical conversion, interspecies or individual differences are small.

In particular, the present invention is very useful when applied to insoluble pharmaceutical agents that comprise an alcoholic hydroxyl group, or preferably a secondary or tertiary alcoholic hydroxyl group.

For example, the water-soluble prodrugs of the present invention can easily solubilize preventive or therapeutic agents for cell proliferation disorders, such as camptothecins, taxanes, and anticancer nucleotides; or insoluble compounds that are used as antifungal agents such as azole antifungal agents. Therefore, pharmaceutical compositions comprising water-soluble prodrugs represented by formulas (1) to (8) of the present invention, or pharmaceutically acceptable salts, hydrates, or solvates derived from these insoluble compounds, as active ingredients are suitable antifungal agents, or preventive or therapeutic agents for cell proliferation disorders.

An example of the aforementioned cell proliferation disorder is cancer. Examples of cancer include colorectal cancer, lung cancer, breast cancer, gastric cancer, uterine cervical cancer, bladder cancer, and such.

Furthermore, the present invention relates to preventive or therapeutic methods for cell proliferation disorders or fungal diseases. The present invention also relates to methods comprising the step of administering a therapeutically effective amount of a water-soluble prodrugs represented by any of formulas (1) to (8), or a pharmaceutically acceptable salt, hydrate, or solvate thereof, to patients in need of such prevention or treatment. These methods are particularly useful for treating cell proliferation disorders including cancers and solid tumors, such as colorectal cancer, lung cancer, breast cancer, gastric cancer, uterine cervical cancer, and bladder cancer.

When using a pharmaceutical composition of the present invention as a therapeutic agent or preventive agent for a cell proliferation disorder, or as an antifungal agent, the method of administration preferably includes parenteral (intravenous, intramuscular, or subcutaneous) administration, local (drip infusion) administration, and inhalation (oral or nasal spray). The mode of administration preferably includes, for example, aqueous oral solutions and suspensions, and parenteral solutions loaded into an appropriate container that is suitable for administration in doses of small amounts. Furthermore, the mode of administration can be adjusted to various methods of administration, including those involve controlled release of formulations, such as subcutaneous transplantation.

The pharmaceutical compositions of the present invention are preferably used as aqueous liquid formulations. More specifically, the aqueous liquid formulations of this invention comprise the water-soluble prodrugs represented by formulas (1) to (8), and pharmaceutically acceptable salts, hydrates, and solvates thereof.

Aqueous solutions that may be used include phosphate buffer, physiological saline, and various other infusion solutions.

The pH of the aqueous solution is preferably 4 or less, more preferably 3 or less, and even more preferably in the range of 2 to 3, and at such pH, the water-soluble prodrugs represented by formulas (1) to (8), and their pharmaceutically acceptable salts, hydrates, and solvates can exist stably in solution for long periods of time. On the other hand, preferably at pH5 or higher, or more preferably at physiological conditions of pH7-8, active forms derived from alcoholic hydroxyl groups can be dissociated rapidly and quantitatively in a short period of time.

Therefore, for example, when an aqueous liquid formulation that is particularly effective when used in its injectable form is administered at a pH value of preferably 4 or less, more preferably 3 or less, and even more preferably in the range of 2 to 3, its active form can be dissociated rapidly in the blood.

The aqueous solution formulation is produced by a well known method using additives such as stabilizers, flavoring agents, and diluents.

Examples of stabilizers include paraoxybenzoic acid esters such as methyl paraben, and propyl paraben; alcohols such as chlorobutanol, benzyl alcohol, and phenylethyl alcohol; benzalkonium chloride; phenols such as phenol and cresol; thimerosal; dehydroacetic acid; and sorbic acid.

Examples of flavoring agents include the commonly used sweetening agents, sour agents, and flavors.

Furthermore, examples of solvents that can be used to produce liquid agents include ethanol, phenol, chlorocresol, purified water, and distilled water.

Examples of surfactants or emulsifiers include polysorbate 80, polyoxyl 40 stearate, and lauromacrogol.

When using a pharmaceutical composition of the present invention as a therapeutic agent or preventive agent for a cell proliferation disorder, or as an antifungal agent, the amounts of the water-soluble prodrugs represented by formulas (1) to (8), or their pharmaceutically acceptable salts, hydrates, or solvates that are used, will differ depending on the patient's symptoms, age, body weight, relative state of health, presence of other administered agents, method of administration, and such.

For example, the active ingredient (water-soluble prodrug) may be delivered to a patient (warm-blooded animal, especially human), at an effective dose; for example, a daily dose of preferably 0.1 to 1000 mg per kg body weight, and even more preferably 10 to 800 mg per kg body weight, in the case of a parenteral agent. This is suitably administered once daily or in several portions throughout the day depending on the symptoms.

There are no limitations on the concentration of the water-soluble prodrugs represented by formulas (1) to (8), or their pharmaceutically acceptable salts, hydrates, or solvates in the aqueous solution, which differs depending on the extent and type of the disease, but is usually in a preferred range of (1) μM to (500) μM.

All prior art references cited herein are incorporated herein by reference.

EXAMPLES

Hereinafter, the present invention is specifically illustrated with reference to Examples, but it is not to be construed as being limited thereto.

NMR analysis was performed using JEOL JNM-EX270 (270 MHz), JNMGSX400 (400 MHz), or JNM-A500 (500 MHz). NMR data were reported in ppm (parts per million) and referenced to the deuterium lock signal of the sample solvent.

The mass spectral data were obtained using JEOL JMS-DX303, or JMS-SX/SX102A.

Data from mass spectrometers equipped with a high performance liquid chromatography instrument were obtained using micromass (Micromass, ZMD) equipped with a Waters 996-600E gradient high performance liquid chromatography instrument, or micromass (Finnigan, Navigator) equipped with an Agilent 1100 gradient high performance liquid chromatography instrument (Agilent Technologies).

For synthetic organic reactions, commercially available reagents were used without further purification.

In the Examples, room temperature refers to a temperature in the range of approximately 20 to 25° C.

All water-free reactions were performed under nitrogen atmosphere. Concentration or solvent removal under reduced pressure was performed using a rotary evaporator, unless stated otherwise.

Compounds were prepared while having their functional groups protected with protecting groups, as necessary, and the protecting groups were removed after the protected form of a target molecule was completed. Selection of the protecting group, and attachment and detachment manipulations were performed, for example, according to the methods described in "Greene and Wuts, Protective Group in Organic Synthesis/2nd edition, John Wiley & Sons, 1991".

High performance liquid chromatography employed one of the following two conditions.

High Performance Liquid Chromatography Condition 1

Column: Combi ODS (ODS, 5 μm, 4.6 mm I.D.×50 mm, Wako Pure Chemicals), COSMOSIL (ODS, 5 μm, 4.6 mm I.D.×50 mm, Nakalai Tesque), or Inertsil C18 (ODS, 5 μm, 4.6 mm I.D.×50 mm, GL Science)

Mobile phase: (Solvent A) water containing 0.01% trifluoroacetic acid, and (Solvent B) acetonitrile containing 0.01% trifluoroacetic acid.

Elution method: stepwise gradient elution in Solvent B: 10% to 95% (3.5 minutes), 95% to 10% (1 minute), and 10% (0.5 minutes)

Flow rate: 4.0 mL/minute

High Performance Liquid Chromatography Condition 2

Column: Combi ODS (ODS, 5 μm, 4.6 mm I.D.×50 mm, Wako Pure Chemicals), COSMOSIL (ODS, 5 μm, 4.6 mm I.D.×50 mm, Nakalai Tesque), or Inertsil C18 (ODS, 5 μm, 4.6 mm I.D.×50 mm, GL Science)

Mobile phase: (Solvent A) water containing 0.01% trifluoroacetic acid, and (Solvent B) acetonitrile containing 0.01% trifluoroacetic acid.

Elution method: stepwise gradient elution in Solvent B: 30% to 35% (0.2 minutes), 35% to 98% (3.3 minute), 98% to 30% (1 minute), and 30% B (0.5 minutes)

Flow rate: 4.0 mL/minute

Example 1

(9S)-9-Ethyl-9-{[methyl-(2-methylamino-ethyl)-amino]-acetoxy}-1-pentyl-1H,12H-pyrano[3'',4'':6',7']indolizino[1',2':6,5pyrido[4,3,2-de]quinazoline-10,13(9H,15H)-dione hydrochloride (compound 1A)

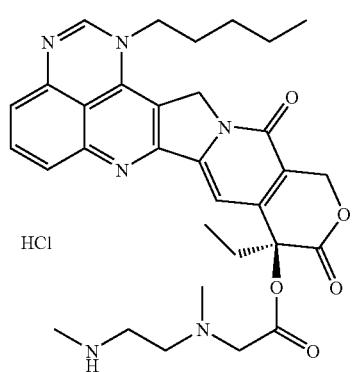

Process 1-A

{[2-(tert-Butoxycarbonyl-methyl-amino)-ethyl]-methyl-amino}-acetic acid benzyl ester

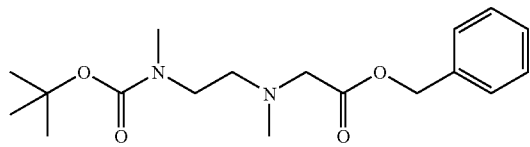

854 mg (4.54 mmol) of methyl-(2-methyl-amino-ethyl)-carbamic acid tert-butyl ester, which is a known substance (J. Med. Chem., 2000, 43, 3093), was dissolved in methylene chloride (50 mL), and then benzyl 2-bromoacetate (1.0 mL, 6.35 mmol) was added to this solution, and the mixture was stirred at room temperature for approximately 24 hours.

After completion of the reaction, the reaction solution was concentrated, and the residue obtained was purified by silica gel column chromatography (hexane:ethyl acetate=5:1 to 3:1) to give 534.3 mg (35%) of {[2-(tert-butoxycarbonyl-methyl-amino)-ethyl]-methyl-amino}-acetic acid benzyl ester as a colorless viscous oil.

$^1$H-NMR (270 MHz, CDCl$_3$) δ(ppm): 1.42 (9H, s), 2.40 (3H, s), 2.65 (2H, t, J=7.1 Hz), 2.82 (3H, s), 3.20-3.38 (2H, m), 3.34 (2H, s), 5.13 (2H, s), 7.24-7.38 (5H, m)

ESI (LC-MS positive mode) m/z 337 (M+H).

Process 1-B

{[2-(tert-Butoxycarbonyl-methyl-amino)-ethyl]-methyl-amino}-acetic acid

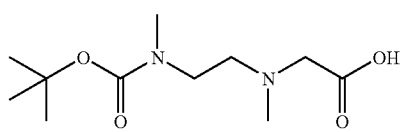

534.3 mg (1.59 mmol) of {[2-(tert-butoxycarbonyl-methyl-amino)-ethyl]-methyl-amino}-acetic acid benzyl ester prepared in Process 1-A was dissolved in methanol (20 mL), and then 51 mg of 5% palladium-carbon was added, and this was stirred for 1 hour under hydrogen atmosphere at room temperature. Insoluble substances were removed by filtration, and the filtrate was concentrated to give 391.1 mg (100%) of {[2-(tert-butoxycarbonyl-methyl-amino)-ethyl]-methyl-amino}-acetic acid as a colorless viscous oil.

$^1$H-NMR (270 MHz, CDCl$_3$) δ(ppm): 1.43 (9H, s), 2.72 (3H, s), 2.87 (3H, s), 2.95-3.10 (2H, m), 3.45 (2H, s), 3.31-3.63 (2H, m)

ESI (LC-MS positive mode) m/z 247 (M+H)

Process 1-C (9S)-9-({[2-(tert-Butoxycarbonyl-methyl-amino)-ethyl]-methyl-amino}-acetoxy)-9-ethyl-1-pentyl-1H,12H-pyrano[3'',4'':6',7']indolizino[1',2':6,5]pyrido[4,3,2-de]quinazoline-10,13(9H,15H)-dione

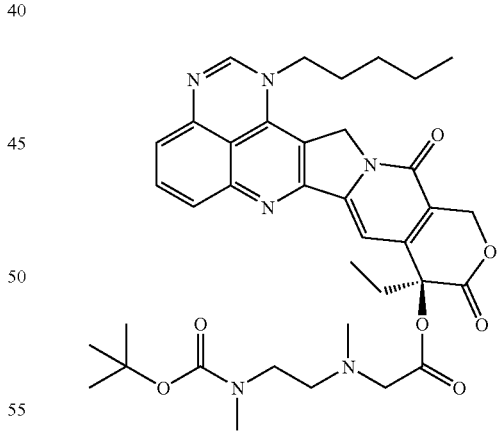

391 mg (1.59 mmol) of {[2-(tert-butoxycarbonyl-methyl-amino)-ethyl]-methyl-amino}-acetic acid prepared in Process 1-B, 279 mg (0.61 mmol) of (9S)-9-ethyl-9-hydroxy-1-pentyl-1H,12H-pyrano[3'',4'':6',7']indolizino[1',2':6,5]pyrido[4,3,2-de]quinazoline-10,13(9H,15H)-dione (prepared according to Example 2.15 of WO03/045952), 525 mg (2.74 mmol) of 1-ethyl-3-(3-dimethylaminopropyl)-carbodiimide hydrochloride, and 224 mg (1.83 mmol) of 4-dimethylaminopyridine were dissolved in methylene chloride (15 mL), and then stirred at room temperature for four hours.

The reaction solution was washed with 0.15 N aqueous hydrochloric acid, dried over anhydrous sodium sulfate, and then the solvent was distilled off under reduced pressure. By purifying the resulting residue using silica gel column chromatography (methylene chloride:methanol=30:0 to 10:1), 136.4 mg (33%) of (9S)-9-({[2-(tert-butoxycarbonyl-methyl-amino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione was obtained as a yellow amorphous substance.

$^1$H-NMR (270 MHz, CDCl$_3$) δ(ppm): 0.85-0.95 (6H, m), 1.27-1.50 (4H, m), 1.40 (9H, s), 1.70-1.84 (2H, m), 2.03-2.30 (2H, m), 2.39 (3H, s), 2.58-2.70 (2H, m), 2.80 (3H, s), 3.18-3.36 (2H, m), 3.48 (2H, s), 3.81 (2H, t, J=7.3 Hz), 5.21 (2H, s), 5.37 (1H, d, J=17.3 Hz), 5.64 (1H, d, J=17.3 Hz), 7.07 (1H, s), 7.14 (1H, dd, J=1.3, 7.3 Hz), 7.38 (1H, s), 7.53-7.70 (2H, m)

ESI (LC-MS positive mode) m/z 687 (M+H).

Process 1-D (9S)-9-Ethyl-9-{[methyl-(2-methylamino-ethyl)-amino]-acetoxy}-1-pentyl-1H,12H-pyrano[3",4":6',7']indolizino[1',2':6,5]pyrido[4,3,2-de]quinazoline-10,13(9H,15H)-dione hydrochloride

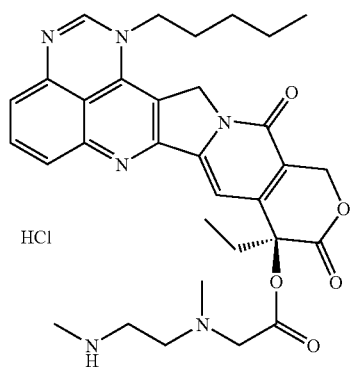

136.4 mg (0.20 mmol) of (9S)-9-({[2-(tert-butoxycarbonyl-methyl-amino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione prepared in Process 1-C was dissolved in 1 N hydrochloric acid-acetic acid solution (3 mL), and then stirred at room temperature for 2.5 hours.

Ethyl acetate was added to the reaction solution, this was then stirred at room temperature for 30 minutes, and the resulting solid was collected by filtration, and 102.7 mg (74%) of (9S)-9-ethyl-9-{[methyl-(2-methylamino-ethyl)-amino]-acetoxy}-1-pentyl-1H,12H-pyrano[3",4":6',7']indolizino[1',2':6,5]pyrido[4,3,2-de]quinazoline-10,13(9H,15H)-dione hydrochloric acid (compound 1A) was obtained as a yellowish red solid.

$^1$H-NMR (270 MHz, CD$_3$OD) δ(ppm): 0.99 (3H, t, J=6.9 Hz), 1.09 (3H, t, J=7.4 Hz), 1.40-1.62 (4H, m), 1.88-2.02 (2H, m), 2.15-2.31 (2H, m), 2.75 (3H, s), 2.96-3.06 (3H, m), 3.39-3.62 (4H, m), 4.25 (2H, t, J=7.9 Hz), 4.44-4.60 (1H, m), 4.87-5.03 (1H, m), 5.53 (2H, s), 5.54 (1H, d, J=17.2 Hz), 5.67 (1H, d, J=17.2 Hz), 7.55 (1H, d, J=7.3 Hz), 7.96-8.17 (3H, m), 8.33 (1H, s)

ESI (LC-MS positive mode) m/z 587 (M+H).

Example 2

(9S)-9-Ethyl-9-(glycyl-sarcosyloxy)-1-pentyl-1H, 12H-pyrano[3",4":6',7']indolizino[1',2':6,5]pyrido[4, 3,2-de]quinazoline-10,13(9H,15H)-dione hydrochloride (Compound 2A)

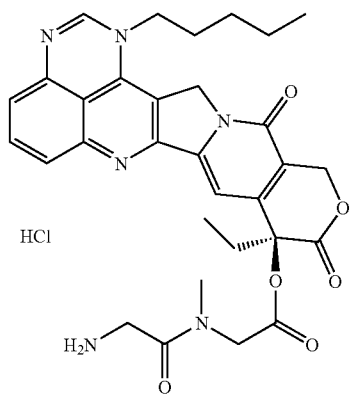

Process 2-A (9S)-9-{[N-(tert-Butoxycarbonyl)-glycyl]-sarcosyloxy}-9-ethyl-1-pentyl-1H,12H-pyrano[3",4": 6',7']indolizino[1',2':6,5]pyrido[4,3,2-de]quinazoline-10, 13(9H,15H)-dione

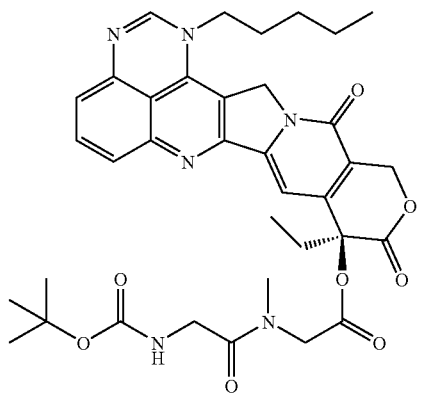

1.4 g (5.67 mmol) of [N-(tert-butoxycarbonyl)-glycyl]-sarcosine, which is a known substance (Helvetica Chimica Acta, 1991, 74, 197), 1.3 g (2.84 mmol) of (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione, 2.2 g (11.34 mmol) of 1-ethyl-3-(3-dimethylaminopropyl)-carbodiimide hydrochloride, and 1.4 g (11.34 mmol) of 4-dimethylaminopyridine were dissolved in methylene chloride (50 mL), and then stirred at room temperature for 1.5 hours.

The reaction solution was washed with 0.2 N aqueous hydrochloric acid and saturated aqueous sodium hydrogen carbonate solution, then dried over anhydrous sodium sulfate, and then the solvent was distilled off under reduced pressure. Purification of the resulting residue was performed using silica gel column chromatography (methylene chloride: methanol=100:1 to 30:1), and as a result, 1.34 g (69%) of (9S)-9-{N-(tert-butoxycarbonyl)-glycyl]-sarcosyloxy}-9-ethyl-1-pentyl-1H,12H-pyrano[3",4":6',7']indolizino[1',2':6,5]pyrido[4,3,2-de]quinazoline-10,13(9H,15H)-dione was obtained as a yellowish red amorphous substance.

¹H-NMR (270 MHz, CDCl₃) δ(ppm):
Rotamer A* 0.86-1.04 (6H, m), 1.24-1.53 (4H, m), 1.38 (9H, s), 1.70-1.90 (2H, m), 2.03-2.36 (2H, m), 3.04 (3H, s), 3.83 (2H, t, J=7.1 Hz), 3.96-4.05 (2H, m), 4.12 (1H, d, J=17.7 Hz), 4.57 (1H, d, J=17.7 Hz), 5.21 (2H, s), 5.38 (1H, d, J=17.3 Hz), 5.46-5.56 (1H, m), 5.66 (1H, d, J=17.3 Hz), 7.10-7.21 (2H, m), 7.40 (1H, s), 7.60-7.75 (2H, m);

Rotamer B* 0.86-1.04 (6H, m), 1.24-1.53 (4H, m), 1.38 (9H, s), 1.70-1.90 (2H, m), 2.03-2.36 (2H, m), 3.02 (3H, s), 3.83 (2H, t, J=7.1 Hz), 3.90-3.96 (2H, m), 4.12 (1H, d, J=17.7 Hz), 4.57 (1H, d, J=17.7 Hz), 5.24 (2H, s), 5.38 (1H, d, J=17.3 Hz), 5.46-5.56 (1H, m), 5.68 (1H, d, J=17.3 Hz), 7.10-7.21 (2H, m), 7.40 (1H, s), 7.60-7.75 (2H, m).

*The ratio of the two rotamers, A and B, was approximately 5:1.

ESI (LC-MS positive mode) m/z 687 (M+H).

Process 2-B (9S)-9-Ethyl-9-(glycyl-sarcosyloxy)-1-pentyl-1H,12H-pyrano[3",4":6',7']indolizino[1',2':6,5]pyrido[4,3,2-de]quinazoline-10,13(9H,15H)-dione hydrochloride

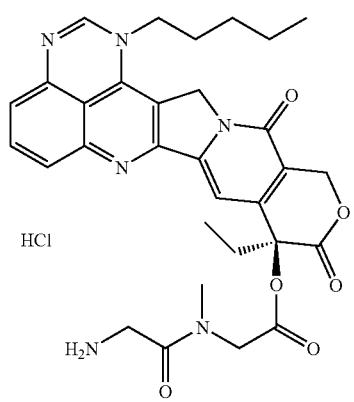

1.33 g (1.94 mmol) of (9S)-9-[{N-(tert-butoxycarbonyl)-glycyl]-sarcosyloxy}-9-ethyl-1-pentyl-1H,12H-pyrano[3",4":6',7']indolizino[1',2':6,5]pyrido[4,3,2-de]quinazoline-10,13(9H,15H)-dione, which was prepared in Process 2-A, was dissolved in 1 N hydrochloric acid-acetic acid solution (15 mL), and then stirred at room temperature for 2 hours and 45 minutes.

Ethyl acetate was added to the reaction solution, which was then stirred at room temperature for 30 minutes, the resulting solid was collected by filtration, and 1.28 g (100%) of (9S)-9-ethyl-9-(glycyl-sarcosyloxy)-1-pentyl-1H,12H-pyrano[3",4":6',7']indolizino[1',2':6,5]pyrido[4,3,2-de]quinazoline-10,13(9H,15H)-dione hydrochloric acid (compound 2A) was obtained as a yellow solid.

¹H-NMR (270 MHz, CD₃OD) δ(ppm):
Rotamer A* 0.99 (3H, t, J=7.1 Hz), 1.03 (3H, t, J=7.6 Hz), 1.34-1.58 (4H, m), 1.90-2.00 (2H, m), 2.14-2.30 (2H, m), 3.11 (3H, s), 3.99 (2H, s), 4.25 (2H, t, J=7.3 Hz), 4.56 (1H, d, J=17.9 Hz), 4.57 (1H, d, J=17.9 Hz), 5.51 (1H, d, J=17.4 Hz), 5.52 (2H, s), 5.61 (1H, d, J=17.4 Hz), 7.52-7.57 (1H, m), 7.89 (1H, s), 7.80 (1H, d, J=8.2 Hz), 8.10 (1H, t, J=8.2 Hz), 8.38 (1H, s);

Rotamer B* 0.99 (3H, t, J=7.1 Hz), 1.08 (3H, t, J=7.3 Hz), 1.34-1.58 (4H, m), 1.90-2.00 (2H, m), 2.14-2.30 (2H, m), 3.08 (3H, s), 3.90 (1H, d, J=16.5 Hz), 4.02 (1H, d, J=16.5 Hz), 4.25 (2H, t, J=7.3 Hz), 4.62 (1H, d, J=18.8 Hz), 4.76 (1H, d, J=18.8 Hz), 5.52 (2H, s), 5.53 (1H, d, J=16.9 Hz), 5.65 (1H, d, J=16.9 Hz), 7.52-7.57 (1H, m), 8.03 (1H, d, J=8.2 Hz), 8.10 (1H, t, J=8.2 Hz), 8.19 (1H, s), 8.34 (1H, s).

*The ratio of the two rotamers, A and B, was approximately 3:2.

ESI (LC-MS positive mode) m/z 587 (M+H).

Example 3

(9S)-9-1[(2-Amino-ethyl)-methyl-amino]-acetoxy}-9-ethyl-1-pentyl-1H,12H-pyrano[3",4":6',7']indolizino[1',2':6,5]pyrido[4,3,2-de]quinazoline-10,13(9H,15H)-dione hydrochloride (compound 3A)

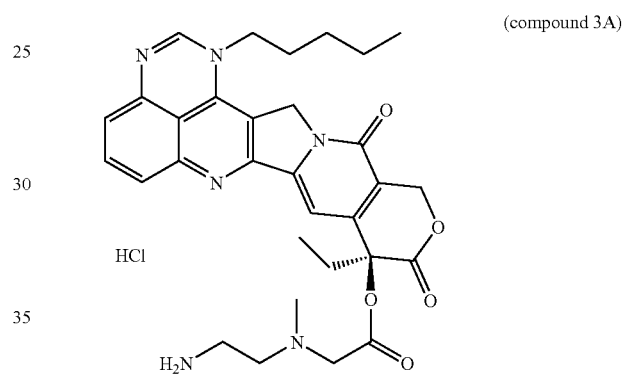

Process 3-A

{[2-(tert-Butoxycarbonylamino)-ethyl]-methyl-amino}-acetic acid benzyl ester

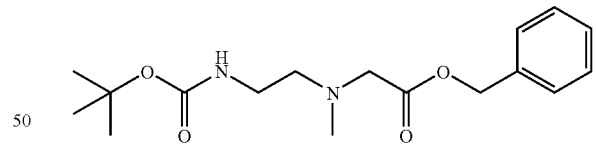

500 mg (1.42 mmol) of sarcosine benzyl ester p-toluenesulfonate, 478 mg (2.13 mmol) of 2-(tert-butoxycarbonylamino)-ethyl bromide, and 0.25 mL (2.13 mmol) of diisopropyl-ethylamine were dissolved in methylene chloride (10 mL), and then stirred at room temperature for approximately three days. After completion of the reaction, the reaction solution was concentrated and the residue obtained was purified by silica gel column chromatography (ethyl acetate) to yield 175 mg (38%) of {[2-(tert-butoxycarbonylamino)-ethyl]-methyl-amino}-acetic acid benzyl ester as a colorless viscous oil.

¹H-NMR (270 MHz, CDCl₃) δ(ppm): 1.44 (9H, s), 2.37 (3H, s), 2.63 (2H, t, J=6.0 Hz), 3.20 (2H, br.q), 3.33 (2H, s), 5.15 (1H, br.s), 5.16 (2H, s), 7.32-7.39 (5H, m)

ESI (LC-MS positive mode) m/z 323 (M+H).

Process 3-B

{[2-(tert-Butoxycarbonylamino)-ethyl]-methyl-amino}-acetic acid

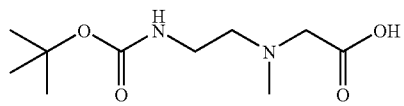

162 mg (0.5 mmol) of {[2-(tert-butoxycarbonylamino)-ethyl]-methyl-amino}-acetic acid benzyl ester prepared in Process 3-A was dissolved in methanol (5 mL), and then 5% palladium-carbon was added to it, and this was stirred under a hydrogen atmosphere at room temperature for one hour. After filtering off the insoluble material, the filtrate was concentrated to yield 116 mg (100%) of {[2-(tert-butoxycarbonylamino)-ethyl]-methyl-amino}-acetic acid as a colorless viscous oil.

$^1$H-NMR (270 MHz, CD$_3$OD) δ(ppm): 1.45 (9H, s), 2.91 (3H, s), 3.22 (2H, t, J=6.3 Hz), 3.41 (2H, t, J=6.3 Hz), 3.63 (2H, s)

ESI (LC-MS positive mode) m/z 233 (M+H).

Process 3-C (9S)-9-({[2-(tert-Butoxycarbonylamino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione

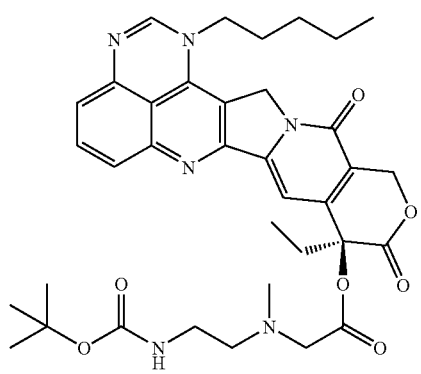

112 mg (0.48 mmol) of {[2-(tert-butoxycarbonylamino)-ethyl]-methyl-amino}-acetic acid prepared in Process 3-B, 157 mg (0.34 mmol) of (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione, 197 mg (1.03 mmol) of 1-ethyl-3-(3-dimethylaminopropyl)-carbodiimide hydrochloride, and 83 mg (0.68 mmol) of 4-dimethylaminopyridine were dissolved in methylene chloride (10 mL), and then stirred at room temperature for three hours.

The reaction solution was washed with 0.3 N aqueous hydrochloric acid solution, dried over anhydrous sodium sulfate, and then the solvent was distilled off under reduced pressure. By purifying the obtained residue by silica gel column chromatography (methylene chloride:methanol=50:1), 61 mg (27%) of (9S)-9-({[2-(tert-butoxycarbonylamino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione was obtained as a yellow viscous oil.

$^1$H-NMR (270 MHz, CDCl$_3$) δ(ppm): 0.88-1.00 (6H, m), 1.32-1.53 (4H, m), 1.42 (9H, s), 1.73-1.86 (2H, m), 2.08-2.36 (2H, m), 2.39 (3H, s), 2.63 (2H, t, J=5.9 Hz), 3.20 (2H, br.q), 3.46 (2H, s), 3.82 (2H, t, J=7.1 Hz), 5.21 (1H, br.s), 5.22 (2H, s), 5.40 (1H, d, J=17.2 Hz), 5.67 (1H, d, J=17.2 Hz), 7.10 (1H, s), 7.14 (1H, br.d), 7.40 (1H, br.s), 7.58-7.70 (2H, m)

ESI (LC-MS positive mode) m/z 673 (M+H).

Process 3-D (9S)-9-{[(2-Amino-ethyl)-methyl-amino]-acetoxy}-9-ethyl-1-pentyl-1H,12H-pyrano[3",4":6',7']indolizino[1',2':6,5]pyrido[4,3,2-de]quinazoline-10,13(9H,15H)-dione hydrochloride

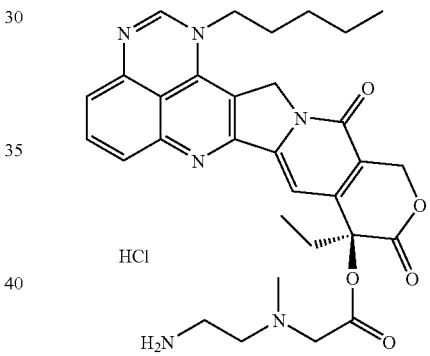

58 mg (0.086 mmol) of (9S)-9-({[2-(tert-butoxycarbonylamino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione prepared in Process 3-C was dissolved in 1N hydrochloric acid-acetic acid solution (2 mL), and then stirred at room temperature for four hours.

Ethyl acetate was added to the reaction solution, which was then stirred at room temperature for 30 minutes, and the resulting solid was collected by filtration, and thus, 54 mg (93%) of (9S)-9-{[(2-amino-ethyl)-methyl-amino]-acetoxy}-9-ethyl-1-pentyl1H,12H-pyrano[3",4":6',7']indolizino[1',2':6,5]pyrido[4,3,2-de]quinazoline-10,13(9H,15H)-dione hydrochloride (compound 3A) was obtained as a yellow solid.

$^1$H-NMR (270 MHz, CD$_3$OD) δ(ppm): 0.99 (3H, t, J=6.9 Hz), 1.09 (3H, t, J=7.3 Hz), 1.39-1.62 (4H, m), 1.88-2.02 (2H, m), 2.16-2.30 (2H, m), 3.07 (3H, s), 3.37-3.61 (4H, m), 4.25 (2H, br.t), 4.62 (1H, d, J=17.5 Hz), 5.05 (1H, d, J=17.5 Hz), 5.52 (2H, s), 5.53 (1H, d, J=17.5 Hz), 5.67 (1H, d, J=17.5 Hz), 7.55 (1H, br.d), 7.98-8.16 (3H, m), 8.32 (1H, s)

ESI (LC-MS positive mode) m/z 573 (M+H).

Example 4

(9S)-9-Ethyl-9-(sarcosyl-sarcosyloxy)-1-pentyl-1H,12H-pyrano[3",4":6',7']indolizino[1',2':6,5]pyrido[4,3,2-de]quinazoline-10,13(9H,15H)-dione hydrochloride (compound 4A)

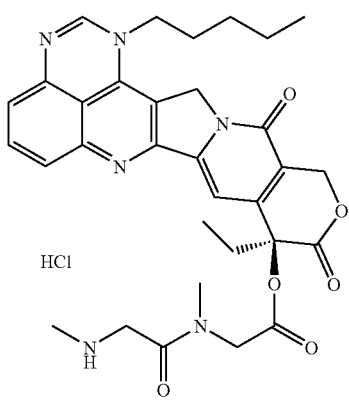

Process 4-A (9S)-9-{[N-tert-Butoxycarbonyl)-sarcosyl]-sarcosyloxy}-9-ethyl-1-pentyl-1H,12H-pyrano[3",4":6',7']indolizino[1',2':6,5]pyrido[4,3,2-de]quinazoline-10,13(9H,15H)-dione 113 mg (0.44 mmol) of [N-(tert-butoxycarbonyl)-sarcosyl]-sarcosine, which is a known substance, 100 mg (0.22 mmol) of (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione, 125 mg (0.65 mmol) of 1-ethyl-3-(3-dimethylaminopropyl)-carbodiimide hydrochloride, and 53 mg (0.44 mmol) of 4-dimethylaminopyridine were dissolved in methylene chloride (6 mL), and then stirred at room temperature for 3.5 hours.

The reaction solution was washed with 0.25 N aqueous hydrochloric acid and aqueous sodium hydrogen carbonate solution, dried over anhydrous sodium sulfate, and then the solvent was distilled off under reduced pressure. The obtained residue was purified by silica gel column chromatography (methylene chloride:methanol=50:1), 103 mg (68%) of (9S)-9-{[N-tert-butoxycarbonyl)-sarcosyl]-sarcosyloxy}-9-ethyl-1-pentyl-1H,12H-pyrano[3",4":6',7']indolizino[1',2':6,5]pyrido[4,3,2-de]quinazoline-10,13(9H,15H)-dione was obtained as a yellow amorphous substance.

$^1$H-NMR (400 MHz, CDCl$_3$) δ(ppm): 0.88-1.02 (6H, m), 1.25-1.51 (13H, m), 1.73-1.82 (2H, m), 2.11-2.32 (2H, m), 2.84 (3H, m), 3.02 (3H, m), 3.80 (2H, br.t), 3.92-4.29 (3H, m), 4.58-4.71 (1H, m), 5.12-5.70 (4H, m), 7.04-7.19 (2H, m), 7.39 (1H, m), 7.55-7.68 (2H, m)

ESI (LC-MS positive mode) m/z 701 (M+H).

Process 4-B (9S)-9-Ethyl-9-(sarcosyl-sarcosyloxy)-1-pentyl-1H,12H-pyrano[3",4":6',7']indolizino[1',2':6,5]pyrido[4,3,2-de]quinazoline-10,13 (9H,15H)-dione hydrochloride

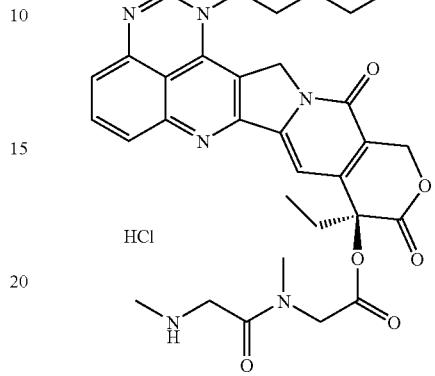

98 mg (0.14 mmol) of (9S)-9-{[N-tert-butoxycarbonyl)-sarcosyl]-sarcosyloxy}-9-ethyl-1-pentyl-1H,12H-pyrano[3",4":6',7']indolizino[1',2':6,5]pyrido[4,3,2-de]quinazoline-10,13(9H,15H)-dione prepared in Process 4-A was dissolved in 1 N hydrochloric acid-acetic acid solution (3 mL), and then stirred at room temperature for two hours. Ethyl acetate was added to the reaction solution, which was then stirred at room temperature for 30 minutes, and the resulting solid was collected by filtration, and thus, 67 mg (71%) of (9S)-9-ethyl-9-(sarcosyl-sarcosyloxy)-1-pentyl-1H,12H-pyrano[3",4":6',7']indolizino[1',2':6,5]pyrido[4,3,2-de]quinazoline-10,13(9H,15H)-dione hydrochloride (compound 4A) was obtained as a yellow solid.

$^1$H-NMR (270 MHz, CD$_3$OD) δ(ppm): 0.96-1.11 (6H, m), 1.40-1.62 (4H, m), 1.87-2.01 (2H, m), 2.15-2.31 (2H, m), 2.71 (3H, s), 3.10 (3H, m), 4.05-4.15 (2H, m), 4.24 (2H, br.t), 4.55-4.70 (2H, m), 5.46-5.70 (4H, m), 7.52 (1H, m), 7.81-8.15 (3H, m), 8.34 (1H, m)

ESI (LC-MS positive mode) m/z 601 (M+H).

Example 5

(Aminoacetyl-methyl-amino-acetic acid (S)-4-ethyl-3,13-dioxo-3,4,12,13-tetrahydro-1H-2-oxa-6,12a-diaza-dibenzo[b,h]fluoren-4-yl ester hydrochloride (compound 5A)

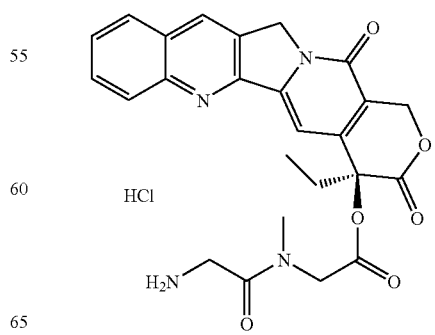

Process 5-A (tert-Butoxycarbonylaminoacetyl-methyl-amino)-acetic acid (S)-4-ethyl-3,13-dioxo-3,4,12,13-tetrahydro-1H-2-oxa-6,12a-diaza-dibenzo[b,h]fluoren-4-yl ester

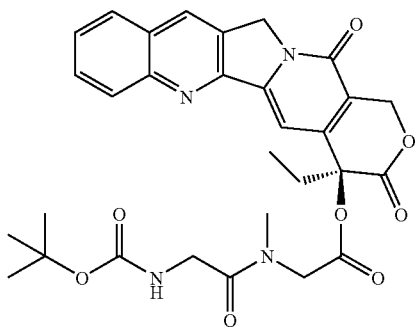

441 mg (1.93 mmol) of N-(tert-butoxycarbonyl)-glycyl]-sarcosine, 250 mg (0.77 mmol) of camptothecin, 343 mg (1.93 mmol) of 1-ethyl-3-(3-dimethylaminopropyl)-carbodiimide hydrochloride, and 87 mg (0.77 mmol) of 4-dimethylaminopyridine were dissolved in methylene chloride (130 mL), and then stirred at room temperature for 15 hours.

The reaction solution was washed with 0.3 N aqueous hydrochloric acid and sodium hydrogen carbonate, and dried over anhydrous sodium sulfate, and then the solvent was distilled off under reduced pressure. By purifying the obtained residue by silica gel column chromatography (methylene chloride:methanol=30:1), 410 mg (99%) of (tert-butoxycarbonylaminoacetyl-methyl-amino)-acetic acid (S)-4-ethyl-3,13-dioxo-3,4,12,13-tetrahydro-1H-2-oxa-6,12a-diaza-dibenzo[b,h]fluoren-4-yl ester was obtained as a yellow solid.

$^1$H-NMR (270 MHz, CDCl$_3$) δ(ppm): 1.00 (3H, t, J=7.6 Hz), 1.35 (9H, s), 2.08-2.34 (2H, m), 3.05 (3H, s), 3.90-4.24 (3H, m), 4.61 (1H, m), 5.28 (2H, br.s), 5.40 (1H, d, J=17.2 Hz), 5.47 (1H, br.s), 5.69 (1H, d, J=17.2 Hz), 7.30 (1H, s), 7.68 (1H, br.t), 7.84 (1H, br.t), 7.93 (1H, br.d), 8.29 (1H, br.d), 8.40 (1H, s)

FAB-MS (positive mode) m/z 577 (M+H).

Process 5-B (Aminoacetyl-methyl-amino)-acetic acid (S)-4-ethyl-3,13-dioxo-3,4,12,13-tetrahydro-1H-2-oxa-6,12a-diaza-dibenzo[b,h]fluoren-4-yl ester hydrochloric acid

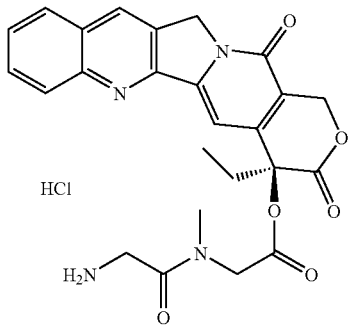

39 mg (0.068 mmol) of (tert-butoxycarbonylaminoacetyl-methyl-amino)-acetic acid (S)-4-ethyl-3,13-dioxo-3,4,12,13-tetrahydro-1H-2-oxa-6,12a-diaza-dibenzo[b,h]fluoren-4-yl ester prepared in Process 5-A was dissolved in 1 N hydrochloric acid-ethyl acetate solution (2 mL), and then stirred at room temperature for four hours.

Ethyl acetate was added to the reaction solution, this was then stirred at room temperature for 30 minutes, and the resulting solid was collected by filtration to yield 28 mg (82%) of (aminoacetyl-methyl-amino)-acetic acid (S)-4-ethyl-3,13-dioxo-3,4,12,13-tetrahydro-1H-2-oxa-6,12a-diaza-dibenzo[b,h]fluoren-4-yl ester hydrochloride (compound 5A) as a yellow solid.

$^1$H-NMR (270 MHz, DMSO-d$_6$) δ(ppm): 0.92 (3H, t, J=7.3 Hz), 2.11-2.24 (2H, m), 2.92-2.98 (3H, m), 3.90 (2H, m), 4.40-4.78 (2H, m), 5.30 (2H, br.s), 5.40-5.60 (2H, m), 7.18-7.27 (1H, m), 7.75 (1H, br.t), 7.89 (1H, br.t), 8.12-8.28 (2H, m), 8.25(br.s), 8.72 (1H, s)

ESI (LC-MS positive mode) m/z 477 (M+H).

Example 6

(9S)-9-{2-[(R-2-Amino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione trifluoroacetic acid salt (compound 6A)

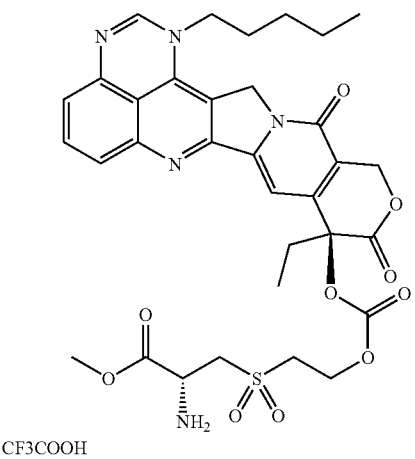

Process 6-A (9S)-9-(2-Bromo-ethoxycarbonyloxy)-9-ethyl-1-pentyl-1H,12H-pyrano[3",4":6',7']indolizino[1',2':6,5]pyrido[4,3,2-de]quinazoline-10,13(9H,15H)-dione

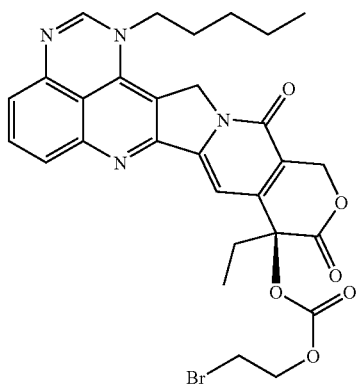

620 mg (1.35 mmol) of (9S)-9-ethyl-9-hydroxy-1-pentyl-1H,12H-pyrano[3",4":6',7']indolizino[1',2':6,5]pyrido[4,3, 2-de]quinazoline-10,13(9H,15H)-dione, 0.29 mL (2.70 mmol) of 2-bromoethyl chloroformate, 0.47 mL (2.70 mmol) of diisopropyl-ethylamine, and 165 mg (1.35 mmol) of 4-dimethylaminopyridine were dissolved in methylene chloride (20 mL), and then stirred at room temperature for approximately 24 hours.

The reaction solution was washed with 0.3 N aqueous hydrochloric acid, dried over anhydrous sodium sulfate, and then the solvent was distilled off under reduced pressure. By purifying the obtained residue by silica gel column chromatography (ethyl acetate), 681 mg (83%) of (9S)-9-(2-bromoethoxycarbonyloxy)-9-ethyl-1-pentyl-1H,12H-pyrano[3",4":6',7']indolizino[1',2':6,5]pyrido[4,3,2-de]quinazoline-10,13(9H,15H)-dione was obtained as a yellow solid.

$^1$H-NMR (270 MHz, CDCl$_3$) δ(ppm): 0.93 (3H, t, J=7.3 Hz), 1.00 (3H, t, J=7.6 Hz), 1.31-1.54 (4H, m), 1.72-1.86 (2H, m), 2.08-2.35 (2H, m), 3.50 (2H, t, J=6.2 Hz), 3.83 (2H, t, J=7.3 Hz), 4.41 (2H, t, J=6.2 Hz), 5.23 (2H, s), 5.37 (1H, d, J=17.0 Hz), 5.68 (1H, d, J=17.0 Hz), 7.16 (1H, br.d), 7.22 (1H, s), 7.40 (1H, s), 7.59-7.71 (2H, m)

ESI (LC-MS positive mode) m/z 609, 611 (M+H).

Process 6-B (9S)-9-{2-[(R-2-tert-Butoxycarbonylamino-2-methoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione

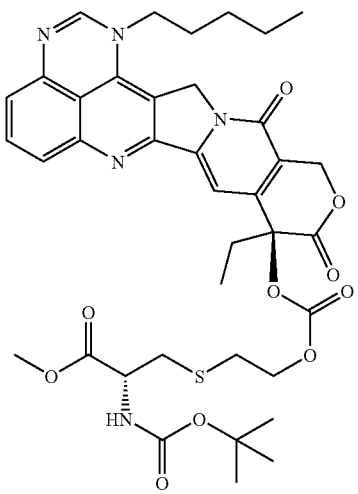

50 mg (0.082 mmol) of (9S)-9-(2-bromo-ethoxycarbonyloxy)-9-ethyl-1-pentyl-1H,12H-pyrano[3",4":6',7']indolizino[1',2':6,5]pyrido[4,3,2-de]quinazoline-10,13(9H,15H)-dione prepared in Process 6-A, 58 mg (0.25 mmol) of tert-butoxycarbonyl-cysteine methyl ester, and 34 mg (0.25 mmol) of potassium carbonate were stirred in acetonitrile (2 mL), at room temperature for six hours.

Following the addition of methylene chloride to the reaction mixture, the solution was washed with 0.3 N aqueous hydrochloric acid, dried over anhydrous sodium sulfate, and then the solvent was distilled off under reduced pressure. By purifying the obtained residue by silica gel column chromatography (methylene chloride:methanol=50:1), 51 mg (82%) of (9S)-9-{2-[(R-2-tert-butoxycarbonylamino-2-methoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione was obtained as a yellow solid.

$^1$H-NMR (270 MHz, CDCl$_3$) δ(ppm): 0.93 (3H, t, J=7.0 Hz), 0.98 (3H, t, J=7.6 Hz), 1.30-1.54 (4H, m), 1.41 (9H, s), 1.68-1.86 (2H, m), 2.05-2.34 (2H, m), 2.78 (2H, t, J=6.8 Hz), 2.89-3.05 (2H, m), 3.71 (3H, s), 3.82 (2H, t, J=7.3 Hz), 4.23 (2H, t, J=6.8 Hz), 4.46 (1H, m), 5.23 (2H, s), 5.37 (1H, d, J=17.0 Hz), 5.42 (1H, m), 5.67 (1H, d, J=17.0 Hz), 7.17 (1H, br.d), 7.22 (1H, s), 7.40 (1H, s), 7.60-7.70 (2H, m)

ESI (LC-MS positive mode) m/z 764 (M+H).

Process 6-C (9S)-9-{2-[(R-2-tert-Butoxycarbonylamino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione

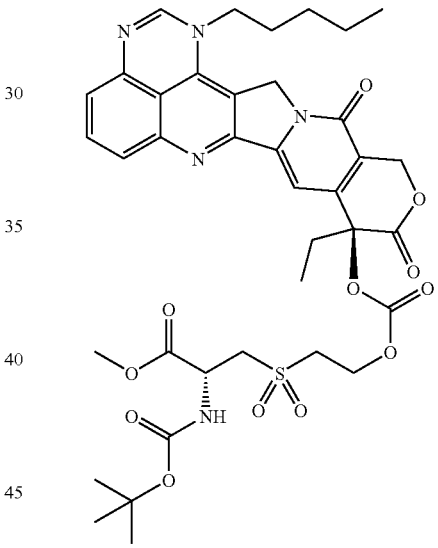

98 mg (0.13 mmol) of (9S)-9-{2-[(R-2-tert-butoxycarbonylamino-2-methoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione produced in Process 6-B, and 158 mg (0.26 mmol) of Oxone™ were stirred in methanol (5 mL) at room temperature for 2.5 hours.

Methylene chloride was added to the reaction mixture, the mixture was washed with water and dried over anhydrous sodium sulfate, and the solvent was distilled off under reduced pressure. By purifying the obtained residue by silica gel column chromatography (methylene chloride:methanol=40:1), 93 mg (92%) of (9S)-9-{2-[(R-2-tert-butoxycarbonylamino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione was obtained as a yellow solid.

ESI (LC-MS positive mode) m/z 796 (M+H).

Process 6-D (9S)-9-{2-[(R-2-Amino-2-methoxycarbonyl)ethane-
sulfonyl]ethoxycarbonyloxy}-9-ethyl-1-pentyl-1H,
12H-pyrano[3",4":6',7']indolizino[1',2':6,5]pyrido[4,
3,2-de]quinazoline-10,13(9H,15H)-dione
trifluoroacetate

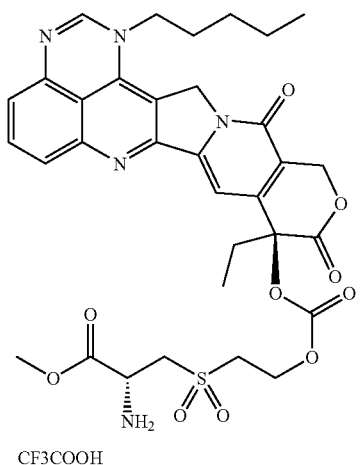

CF3COOH 93 mg (0.12 mmol) of (9S)-9-{2-[(R-2-tert-butoxycarbo-nylamino-2-methoxycarbonyl)ethanesulfonyl]ethoxycarbo-nyloxy}-9-ethyl-1-pentyl-1H,12H-pyrano[3",4":6',7']in-dolizino[1',2':6,5]pyrido[4,3,2-de]quinazoline-10,13(9H,15H)-dione was dissolved in trifluoroacetic acid (3 mL), and then stirred at room temperature for one hour.

Diethyl ether was added to the reaction solution, and stirred at room temperature for 10 minutes. The resulting solid was collected by filtration to yield 88 mg (94%) of (9S)-9-{2-[(R-2-amino-2-methoxycarbonyl)ethanesulfonyl]ethoxycarbo-nyloxy}-9-ethyl-1-pentyl-1H,12H-pyrano[3",4":6',7']in-dolizino[1',2':6,5]pyrido[4,3,2-de]quinazoline-10,13(9H,15H)-dione trifluoroacetate (compound 6A) as a yellow solid.

$^1$H-NMR (270 MHz, CD$_3$OD) δ(ppm): 0.95 (3H, t, J=7.3 Hz), 1.03 (3H, t, J=7.3 Hz), 1.37-1.56 (4H, m), 1.76-1.92 (2H, m), 2.10-2.28 (2H, m), 3.69-4.05 (6H, m), 3.90 (3H, s), 4.48-4.82 (3H, m), 5.35 (2H, s), 5.48 (1H, d, J=16.8 Hz), 5.64 (1H, d, J=16.8 Hz), 7.13 (1H, br.d), 7.28 (1H, s), 7.56 (1H, d, J=8.3 Hz), 7.71 (1H, m), 7.80 (1H, s)

ESI (LC-MS positive mode) m/z 696 (M+H).

Example 7

(9S)-9-{2-[(R-2-Amino-2-ethoxycarbonyl)ethane-
sulfonyl]ethoxycarbonyloxy}-9-ethyl-1-pentyl-1H,
12H-pyrano[3",4":6',7']indolizino[1',2':6,5]pyrido[4,
3,2-de]quinazoline-10,13(9H,15H)-dione
hydrochloride (compound 7A)

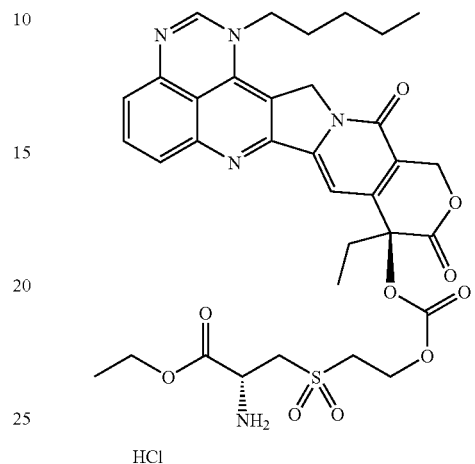

HCl

Process 7-A (9S)-9-{2-[(R-2-tert-Butoxycarbonylamino-2-
ethoxycarbonyl)ethanesulfanyl]ethoxycarbonyloxy}-
9-ethyl-1-pentyl-1H,12H-pyrano[3",4":6',7']in-
dolizino[1',2':6,5]pyrido[4,3,2-de]quinazoline-10,13
(9H,15H)-dione

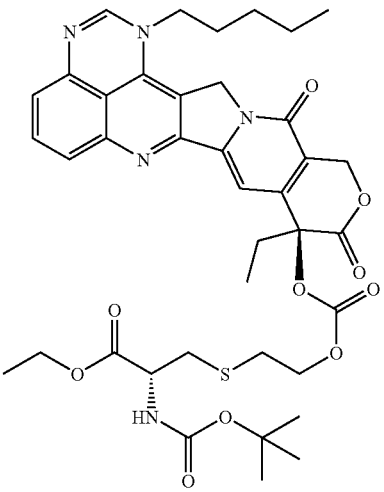

270 mg (0.44 mmol) of (9S)-9-(2-bromo-ethoxycarbony-loxy)-9-ethyl-1-pentyl-1H,12H-pyrano[3",4":6',7']in-dolizino[1',2':6,5]pyrido[4,3,2-de]quinazoline-10,13(9H, 15H)-dione, 333 mg (1.33 mmol) of tert-butoxycarbonyl-cysteine ethyl ester, and 184 mg (1.33 mmol) of potassium carbonate were stirred in acetonitrile (10 mL) at room temperature for 20 hours.

Following the addition of methylene chloride to the reaction mixture, the mixture was washed with 0.3 N aqueous hydrochloric acid, dried over anhydrous sodium sulfate, and the solvent was distilled off under reduced pressure. By purifying the obtained residue by silica gel column chromatography (methylene chloride:methanol=50:1), 159 mg (46%) of (9S)-9-{2-[(R-2-tert-butoxycarbonylamino-2-ethoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione was obtained as a yellow oil.

¹H-NMR (270 MHz, CDCl₃) δ(ppm): 0.93 (3H, t, J=7.3 Hz), 0.97 (3H, t, J=7.3 Hz), 1.25 (3H, t, J=7.3 Hz), 1.32-1.53 (4H, m), 1.41 (9H, s), 1.73-1.85 (2H, m), 2.05-2.35 (2H, m), 2.79 (2H, t, J=6.9 Hz), 2.88-3.05 (2H, m), 3.83 (2H, t, J=7.3 Hz), 4.09-4.28 (4H, m), 4.43 (1H, m), 5.23 (2H, s), 5.37 (1H, d, J=17.2 Hz), 5.43 (1H, m), 5.67 (1H, d, J=17.2 Hz), 7.17 (1H, br.d), 7.21 (1H, s), 7.40 (1H, s), 7.60-7.70 (2H, m)

ESI (LC-MS positive mode) m/z 778 (M+H).

Process 7-B (9S)-9-{2-[(R-2-tert-Butoxycarbonylamino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione

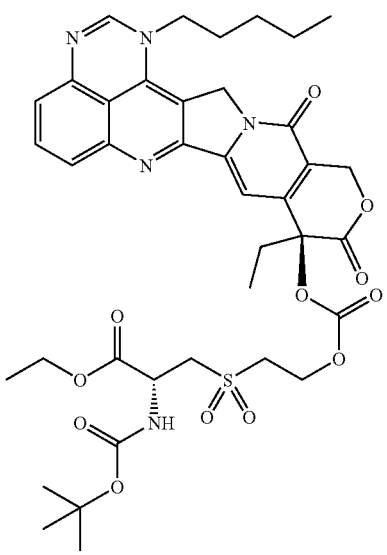

159 mg (0.20 mmol) of (9S)-9-{2-[(R-2-tert-butoxycarbonylamino-2-ethoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione, and 252 mg (0.41 mmol) of Oxone™ were stirred in methanol (8 mL) at room temperature for two hours.

Following the addition of methylene chloride to the reaction mixture, the mixture was washed with water and dried over anhydrous sodium sulfate, and the solvent was distilled off under reduced pressure. By purifying the obtained residue by silica gel column chromatography (methylene chloride:methanol=40:1), 141 mg (88%) of (9S)-9-{2-[(R-2-tert-butoxycarbonylamino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,5H)-dione was obtained as a yellow solid.

¹H-NMR (270 MHz, CDCl₃) δ(ppm): 0.93 (3H, t, J=6.9 Hz), 0.99 (3H, t, J=7.6 Hz), 1.29 (3H, t, J=7.3 Hz), 1.32-1.55 (4H, m), 1.45 (9H, s), 1.72-1.87 (2H, m), 2.07-2.32 (2H, m), 3.25-3.52 (2H, m), 3.73 (2H, m), 3.84 (2H, t, J=7.3 Hz), 4.23 (2H, q, J=7.3 Hz), 4.55 (2H, br.t), 4.71 (1H, m), 5.25 (2H, s), 5.37 (1H, d, J=17.2 Hz), 5.69 (1H, d, J=17.2 Hz), 5.76 (1H, d, J=7.9 Hz), 7.18 (1H, br.d), 7.19 (1H, s), 7.40 (1H, s), 7.61-7.72 (2H, m)

ESI (LC-MS positive mode) m/z 810 (M+H).

Process 7-C (9S)-9-{2-[R-2-Amino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione hydrochloride

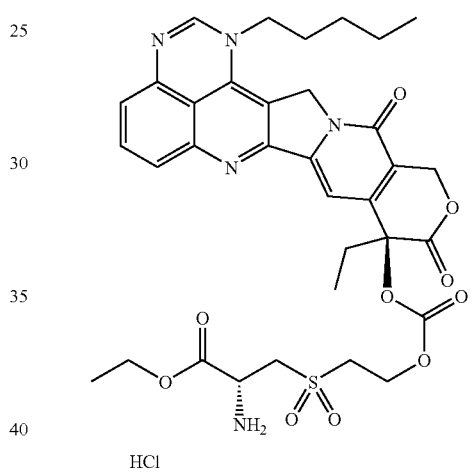

140 mg (0.17 mmol) of (9S)-9-{2-[(R-2-tert-butoxycarbonylamino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione was dissolved in 1N hydrochloric acid-acetic acid solution (5 mL), and then stirred at room temperature for one hour.

Ethyl acetate was added to the reaction solution, and stirred at room temperature for 30 minutes. The resulting solid was collected by filtration to yield 127 mg (94%) of (9S)-9-{2-[R-2-amino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione hydrochloride (compound 7A) as a yellow solid.

¹H-NMR (400 MHz, CD₃OD) δ(ppm): 0.99 (3H, t, J=7.6 Hz), 1.04 (3H, t, J=7.2 Hz), 1.36 (3H, t, J=7.2 Hz), 1.40-1.60 (4H, m), 1.92-2.00 (2H, m), 2.10-2.25 (2H, m), 3.70-3.86 (3H, m), 4.10 (1H, dd, J=15.2, 4.0 Hz), 4.25 (2H, t, J=8.0 Hz), 4.36 (2H, q, J=7.6 Hz), 4.60 (2H, t, J=5.2 Hz), 4.77 (1H, m), 5.52 (1H, d, J=16.8 Hz), 5.54 (2H, s), 5.65 (1H, d, J=16.8 Hz), 7.54 (1H, d, J=7.6 Hz), 7.83 (1H, s), 7.91 (1H, d, J=8.0 Hz), 8.09 (1H, br.t), 8.38 (1H, s)

ESI (LC-MS positive mode) m/z 710 (M+H).

Example 8

(9S)-9-[2-(2-Aminoethanesulfonyl)ethoxycarbonyloxy]-9-ethyl-1-pentyl-1H,12H-pyrano[3'',4'': 6',7']indolizino[1',2':6,5]pyrido[4,3,2-de]quinazoline-10,13(9H,15H)-dione hydrochloride (compound 8A)

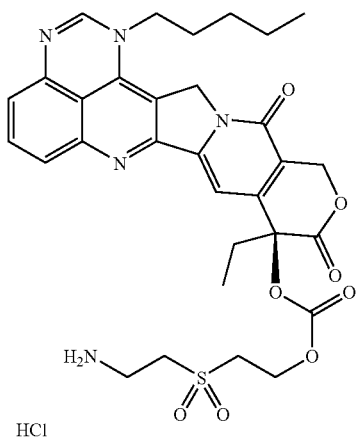

Process 8-A (9S)-9-[2-(2-tert-Butoxycarbonylaminoethanesulfonyl)ethoxycarbonyloxy]-9-ethyl-1-pentyl-1H,12H-pyrano[3'',4'':6',7']indolizino[1',2':6,5]pyrido[4,3,2-de]quinazoline-10,13(9H,15H)-dione

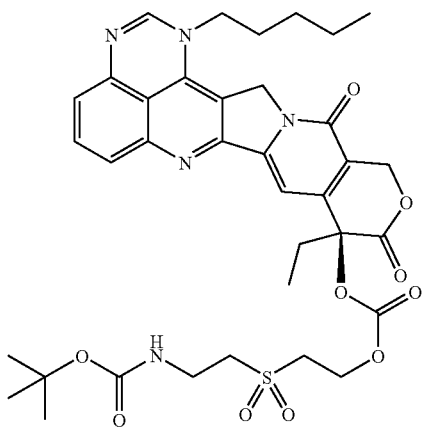

825 mg (1.8 mmol) of (9S)-9-ethyl-9-hydroxy-1-pentyl-1H,12H-pyrano[3'',4'':6',7']indolizino[1',2':6,5]pyrido[4,3,2-de]quinazoline-10,13(9H,15H)-dione, 543 mg (2.7 mmol) of p-nitrophenyl chloroformate, 0.47 mL (2.7 mmol) of diisopropyl-ethylamine, and 220 mg (1.8 mmol) of 4-dimethylaminopyridine were dissolved in methylene chloride (16 mL) on ice, and then stirred at room temperature for three hours. Next, 1.6 g (6.3 mmol) of 2-(2-tert-butoxycarbonylaminoethanesulfonyl)ethanol (Tetrahedron, 55 (1999), 6623-6634) was added to this solution, and this was stirred at room temperature for approximately 24 hours.

The reaction solution was washed with 0.3 N aqueous hydrochloric acid, dried over anhydrous sodium sulfate, and then the solvent was distilled off under reduced pressure. By purifying the obtained residue by silica gel column chromatography (methylene chloride methanol=30:1), 550 mg (42%) of (9S)-9-[2-(2-tert-butoxycarbonylaminoethanesulfonyl)ethoxycarbonyloxy]-9-ethyl-1-pentyl-1H,12H-pyrano[3'',4'':6',7']indolizino[1',2':6,5]pyrido[4,3,2-de]quinazoline-10,13(9H,15H)-dione was obtained as a yellow solid.

$^1$H-NMR (270 MHz, CDCl$_3$) δ(ppm): 0.94 (3H, t, J=7.3 Hz), 1.00 (3H, t, J=7.3 Hz), 1.33-1.55 (4H, m), 1.43 (9H, s), 1.73-1.86 (2H, m), 2.07-2.31 (2H, m), 3.20-3.49 (4H, m), 3.70 (2H, m), 3.84 (2H, t, J=7.3 Hz), 4.57 (2H, br.t), 5.25 (2H, s), 5.37 (1H, d, J=17.2 Hz), 5.45 (1H, m), 5.69 (1H, d, J=17.2 Hz), 7.15-7.20 (2H, m), 7.41 (1H, s), 7.61-7.73 (2H, m)

ESI (LC-MS positive mode) m/z 738 (M+H).

Process 8-B (9S)-9-[2-(2-Aminoethanesulfonyl)ethoxycarbonyloxy]-9-ethyl-1-pentyl-1H,12H-pyrano[3'',4'':6',7']indolizino[1',2':6,5]pyrido[4,3,2-de]quinazoline-10,13(9H,15H)-dione hydrochloride

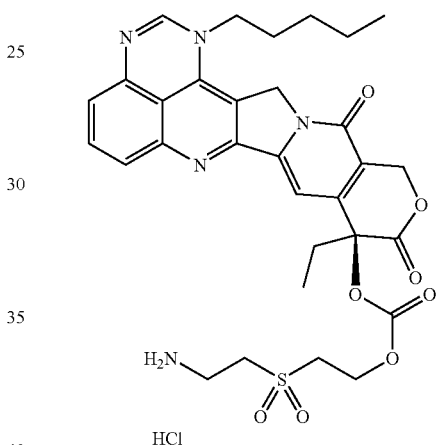

530 mg (0.72 mmol) of (9S)-9-[2-(2-tert-butoxycarbonylaminoethanesulfonyl)ethoxycarbonyloxy]-9-ethyl-1-pentyl-1H,12H-pyrano[3'',4'':6',7']indolizino[1',2':6,5]pyrido[4,3,2-de]quinazoline-10,13(9H,15H)-dione prepared in Process 8-A was dissolved in 1 N hydrochloric acid-acetic acid solution (10 mL), and then stirred at room temperature for one hour.

Ethyl acetate was added to the reaction solution, which was then stirred at room temperature for 30 minutes, and the resulting solid was collected by filtration to yield 480 mg (94%) of (9S)-9[2-(2-aminoethanesulfonyl)ethoxycarbonyloxy]-9-ethyl-1-pentyl-1H,12H-pyrano[3'',4'':6,7']indolizino[1',2':6,5]pyrido[4,3,2-de]quinazoline-10,13(9H,15H)-dione hydrochloride (compound 8A) as a yellow solid.

$^1$H-NMR (270 MHz, CD$_3$OD) δ(ppm): 0.94-1.05 (6H, m), 1.40-161 (4H, m), 1.90-2.04 (2H, m), 2.07-2.28 (2H, m), 3.48-3.81 (6H, m), 4.25 (2H, br.t), 4.55 (2H, m), 5.51 (1H, d, J=17.2 Hz), 5.53 (2H, s), 5.65 (1H, d, J=17.2 Hz), 7.52 (1H, d, J=7.6 Hz), 7.90 (1H, s), 7.93 (1H, d, J=8.6 Hz), 8.08 (1H, br.t), 8.35 (1H, s)

ESI (LC-MS positive mode) m/z 638 (M+H).

Test Example 1

The percentages of compound 2A produced in Example 2 being converted into an activated form in sera of humans, mice, monkeys, and dogs were determined. The activated form is in a rapid equilibrium between the lactone form and the carboxylate form, which were quantified separately.

Compound 2A was incubated at 37° C. at a concentration of 50 μM in sera of humans, mice, monkeys, and dogs. Incubation was terminated at a given time (0, 30, 60, 120, and 360 minutes), and the samples were analyzed by HPLC after deproteinization treatments.

Conditions for the HPLC analysis are as follows:
HPLC conditions
Column: Develosil C30-UG-3, 3 μm, 50×4.6 mm I.D
Column Temperature: constant temperature at approximately 25° C.
Mobile phase: A: 10 mM phosphate buffer (pH4.7)
  B: acetonitrile
  /B (min): 90/10(0)→90/10(0.4)→40/60(6)→2/98(8)→90/10(9)→90/10(15)
Flow rate: 1.0 mL/min
Detection: photodiode array detector, detection wavelength 350 nm
Amount injected: 30 μL The results are shown in Table 3, and FIGS. 1 to 4. The results show that the water-soluble prodrug of this invention (compound 2A) is quickly converted to the lactone form in human, mouse, monkey, and dog sera, confirming the absence of species differences. At 360 minutes of incubation, the lactone-carboxylate equilibrium had shifted toward the carboxylate form. The percentage of the carboxylate form was found to be the highest in human sera, approximately the same in mouse and monkey sera, and slightly lower in dog sera compared to mouse and monkey sera.

Generally, camptothecins in solution are in a rapid equilibrium in which the carbonyl at position 3 forms a 6-membered cyclic ester with the oxygen at position 2, and its open-ring structure. The lactone form refers to the former condition and the carboxylate form refers to the latter condition.

TABLE 3

(measured values, %)

| | | Incubation time (minutes) | | | | |
|---|---|---|---|---|---|---|
| | | 0 | 30 | 60 | 120 | 360 |
| human | compound 2A | 0 | 0 | 0 | 0 | 0 |
| | lactone form | 93.4 | 43.5 | 20.2 | 9.8 | 8.8 |
| | carboxylate form | 6.6 | 56.5 | 79.8 | 90.2 | 91.2 |
| mouse | compound 2A | 0 | 0 | 0 | 0 | 0 |
| | lactone form | 90.6 | 67.9 | 50.6 | 34.4 | 24.5 |
| | carboxylate form | 9.4 | 32.1 | 49.4 | 65.6 | 75.5 |
| monkey | compound 2A | 0 | 0 | 0 | 0 | 0 |
| | lactone form | 93.3 | 57.5 | 38.8 | 24.7 | 20.7 |
| | carboxylate form | 6.7 | 42.5 | 61.2 | 75.3 | 79.3 |
| dog | compound 2A | 0 | 0 | 0 | 0 | 0 |
| | lactone form | 93.9 | 73.2 | 55.7 | 39.5 | 33.9 |
| | carboxylate form | 6.1 | 26.8 | 44.3 | 60.5 | 66.1 |

Test Example 2

The stability of compound 2A at various pH values was determined. The present compound was placed in buffers of various pHs at a concentration of 25 μM. After incubation at 25° C. for 0, 3, and 6 hours, the compound was analyzed by HPLC.

Figure 5:
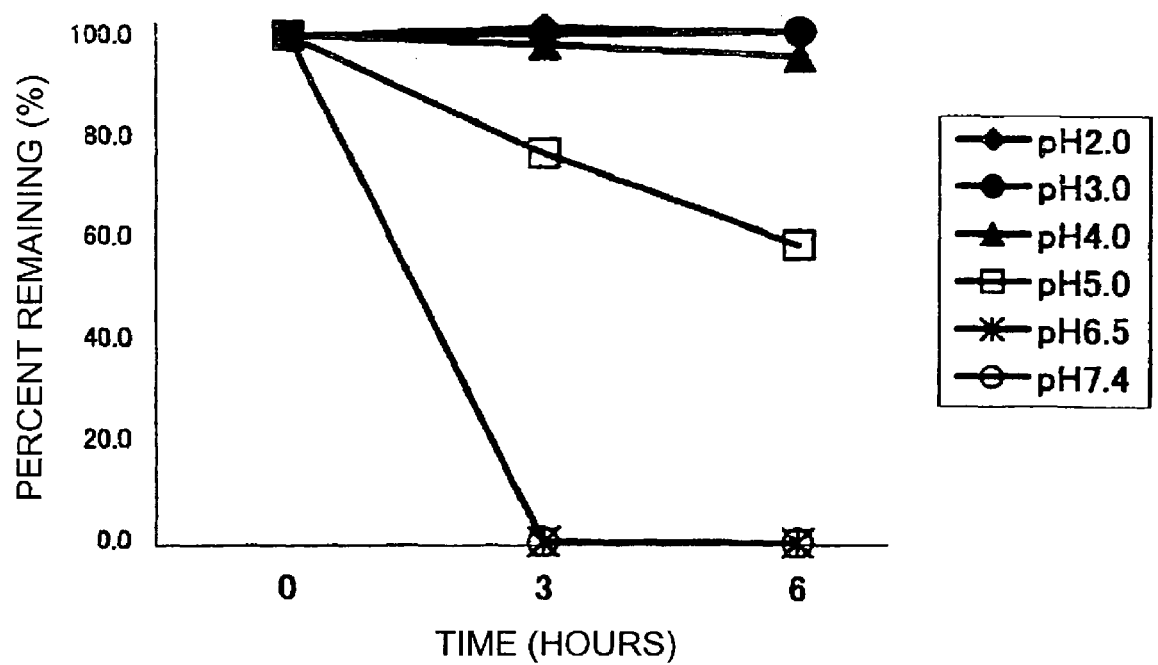
FIG. 5 is a graph showing the remaining percentage (%) of compound 2A at each pH (pH stability) after periods of time.

The buffers used at each pH are shown below.
pH2.0: 50 mM HCl-KCl buffer
pH3.0: 50 mM citrate buffer
pH4.0: 50 mM citrate buffer
pH5.0: 50 mM succinate buffer
pH6.5: 50 mM phosphate buffer
pH7.4: 50 mM phosphate buffer
Conditions for HPLC analysis are as follows:
HPLC conditions
Column: Develosil C30-UG-3, 3 μm, 50×4.6 mm I.D
Column Temperature: constant temperature at approximately 25° C.
Mobile phase: A: 10 mM phosphate buffer (pH4.7)
  B: acetonitrile
  (min): 90/10(0)→90/10(0.4)→40/60(6)→2/98(8)→90/10(9)→90/10(15)
Flow rate: 1.0 mL/min
Detection: photodiode array detector, detection wavelength 350 nm
Amount injected: 30 μL The results are shown in Table 4 and FIG. 5. The results show that the compound of the present invention represented by compound 2A was stable up to pH3, and its stability slightly decreased at pH4 (96.1% after 6 hours).

The values at pH6.5 and pH7.4 had already reached 0% at 3 and 6 hours of incubation. Furthermore, this compound was confirmed to be chemically converted to the lactone form and carboxylate form in a pH-dependent manner.

TABLE 4

(Percent remaining, %)

| | time (hr) | | |
|---|---|---|---|
| | 0 | 3 | 6 |
| pH 2.0 | 100 | 101.6 | 101.1 |
| pH 3.0 | 100 | 100.3 | 101.1 |
| pH 4.0 | 100 | 98.2 | 96.1 |
| pH 5.0 | 100 | 76.6 | 58.7 |
| pH 6.5 | 100 | 0 | 0 |
| pH 7.4 | 100 | 0 | 0 |

Test Example 3

The solubility of the water-soluble prodrugs obtained in the Examples (compounds 1A to 8A) in distilled water was compared to the solubility of (9S)-9-ethyl-9-hydroxy-1-pentyl-1H,12H-pyrano[3",4":6',7']indolizino[1',2':6,5]pyrido[4,3,2-de]quinazoline-10,13 (9H,15H)-dione (representative compound in Patent document 2: reference compound 1).

The results are shown in Table 5. The solubility of the water-soluble prodrugs of this invention was found to be greatly improved compared to reference compound 1.

TABLE 5

| Compound No. | Solubility in distilled water |
|---|---|
| 1A | >10 mg/mL |
| 2A | >10 mg/mL |
| 3A | >10 mg/mL |
| 4A | >10 mg/mL |
| 5A | >10 mg/mL |
| 6A | >10 mg/mL |
| 7A | >10 mg/mL |
| 8A | >10 mg/mL |
| Reference compound 1 | <0.01 mg/mL |

Test Example 4

Parenteral administration of the water-soluble camptothecin prodrugs represented by the aforementioned formulas (2) and (3) into mouse models of colon cancer showed strong activity of cancer growth inhibition over a wide range of doses. Thus, these prodrugs are useful as antitumor agents. An example of the antitumor activity is shown below.

[Determination of Antitumor Effects]

Antitumor effects were determined for representative examples of the group of compounds of the present invention. Tumor-bearing mice were generated by subcutaneous transplantation of human colon cancer cell line HCT116 obtained from American Type Culture Collection (Virginia, USA) into the right flank of BALB/c nude mice purchased from Charles River Japan, and used for determination of antitumor effects.

After a one-week quarantine period, the purchased nude mice were subjected to subcutaneous transplantation of $5 \times 10^6$ HCT116 cells at their right flank. Mice with a tumor size reaching 200 mm$^3$ or so were subjected to the experiment.

The compounds were dissolved in 1 mM citric buffers saline, pH 4, and administered intravenously. The administration was carried out once per week for three weeks, for a total of three administrations. The antitumor effect was determined as tumor growth inhibition (TGI) using the following equation.

Tumor growth inhibition (TGI) (%)={(1−mean tumor volume change in the drug-treated group/mean tumor volume change in the control group)×100}

The results are shown in Table 6.

TABLE 6

| Compound | Dose (mg/kg) | TGI (%) on Day 21 |
|---|---|---|
| Compound 2A | 0.9 | 45 |
| | 1.9 | 52 |
| | 3.75 | 72 |
| | 7.5 | 74 |
| | 15 | 85 |
| | 30 | 97 |
| | 60 | 110 |
| Compound 8A | 0.9 | 41 |
| | 1.9 | 53 |
| | 3.75 | 55 |
| | 7.5 | 61 |
| | 15 | 78 |
| | 30 | 96 |
| | 60 | 106 |

Test Example 5

The percentages of compound 2A produced in Example 2 being converted into an activated form in sera of humans, rats, mice, monkeys, and dogs were determined. The activated form is in a rapid equilibrium between the lactone form and the carboxylate form, which were quantified separately.

Compound 2A was incubated at 37° C. at a concentration of 50 µM in sera of humans, mice, rats, monkeys, and dogs. Incubation was terminated at a given time (0, 30, 60, 120, and 360 minutes), and the samples were analyzed by HPLC after deproteinization treatments.

Conditions for the HPLC analysis are as follows:
HPLC conditions
Column: Develosil C30-UG-3, 3 µm, 35×4.6 mm I.D
Column Temperature: constant temperature at approximately 25° C.
Mobile phase: A: 10 mM phosphate buffer (pH4.7)
B: acetonitrile
/B (min): 90/10(0)→90/10(0.4)→40/60(6)→2/98(8)→90/10(9)→90/10(15)
Flow rate: 1.0 mL/min
Detection: photodiode array detector, detection wavelength 350 nm
Amount injected: 30 µL The results are shown in Table 7. The results show that the water-soluble prodrug of this invention (compound 2A) is quickly converted to the lactone form in human, mouse, rat, monkey, and dog sera, confirming the absence of species differences. At 360 minutes of incubation, the lactone-carboxylate equilibrium had shifted toward the carboxylate form. The percentage of the carboxylate form was found to be the highest in human sera, approximately the same in mouse and monkey sera, and slightly lower in dog sera compared to mouse and monkey sera.

Generally, camptothecins in solution are in a rapid equilibrium between a structure in which the carbonyl at position 3 forms a 6-membered cyclic ester with the oxygen at position 2, and its open-ring structure. The lactone form refers to the former condition and the carboxylate form refers to the latter condition.

TABLE 7

(measured values, %)

| | | Incubation time (minutes) | | | | |
|---|---|---|---|---|---|---|
| | | 0 | 30 | 60 | 120 | 360 |
| human | compound 2A | 0 | 0 | 0 | 0 | 0 |
| | lactone form | 100 | 69.9 | 41.8 | 19.1 | 10.5 |
| | carboxylate form | 0 | 30.1 | 58.2 | 80.9 | 89.5 |
| mouse | compound 2A | 0 | 0 | 0 | 0 | 0 |
| | lactone form | 94.8 | 82.0 | 64.9 | 49.5 | 39.8 |
| | carboxylate form | 5.2 | 18.0 | 35.1 | 50.5 | 60.2 |
| rat | compound 2A | 0 | 0 | 0 | 0 | 0 |
| | lactone form | 88.9 | 61.0 | 43.7 | 32.0 | 30.4 |
| | carboxylate form | 11.1 | 39.0 | 56.3 | 68.0 | 69.6 |
| monkey | compound 2A | 0 | 0 | 0 | 0 | 0 |
| | lactone form | 98.5 | 78.4 | 55.1 | 35.5 | 25.9 |
| | carboxylate form | 1.5 | 21.6 | 44.9 | 64.5 | 74.1 |
| dog | compound 2A | 0 | 0 | 0 | 0 | 0 |
| | lactone form | 98.3 | 90.1 | 80.4 | 66.5 | 55.4 |
| | carboxylate form | 1.7 | 9.9 | 19.6 | 33.5 | 44.6 |

Comparative Test Example 1

Similar to Examination 1, the percent changes of (9S)-9-ethyl-9-(tryptophyl-γ-glutamyloxy)-1-pentyl-1H,12H-pyrano[3″,4″:6′,7′]indolizino[1′,2′:6,5]pyrido[4,3,2-de]quinazoline-10,13(9H,15H)-dione [representative compound (Q) in Patent document 1: reference compound 2] being converted in the lactone form and the carboxylate form over time in human and mouse sera were determined.

Figure 6:
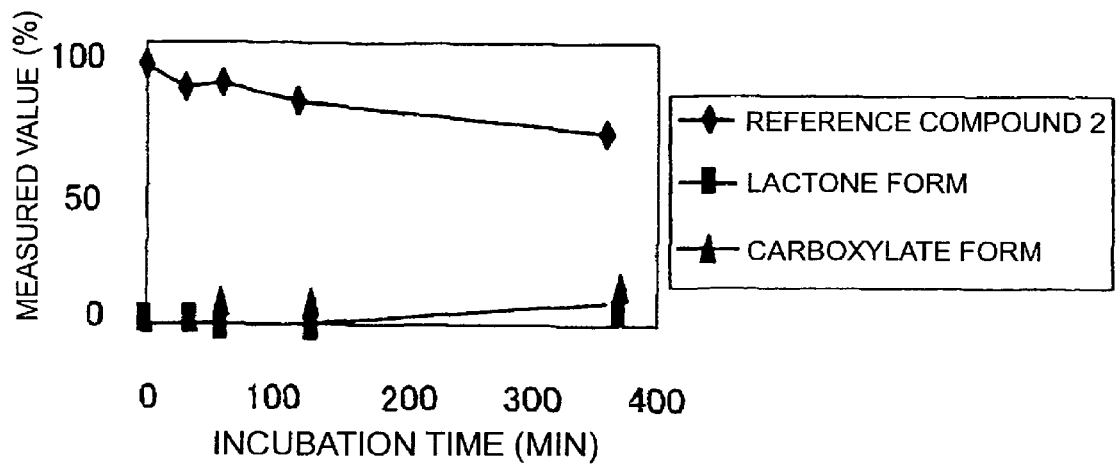
FIG. 6 is a graph showing percent changes in the conversion of reference compound 2 into the lactone form and the carboxylate form in human serum over time.
Figure 7:
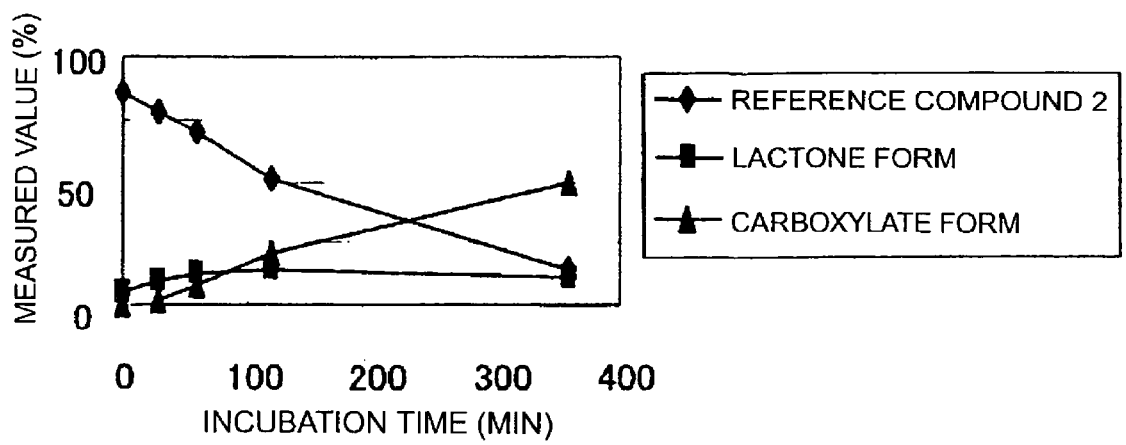
FIG. 7 is a graph showing percent changes in the conversion of reference compound 2 into the lactone form and the carboxylate form in mouse serum over time.

The results from human sera are shown in FIG. 6, and the results from mouse sera are shown in FIG. 7. In both cases, the conversion rate and efficiency were low, and interspecies differences were observed.

INDUSTRIAL APPLICABILITY

The water-soluble prodrugs of the present invention, and pharmaceutically acceptable salts, hydrates, or solvates thereof, have an ester chain of a particular structure which is responsible for their excellent water solubility. In addition, the water-soluble prodrugs of the present invention are rapidly converted to the active form by chemical conversion, and this reduces interspecies or individual differences. In particular, the present invention is very useful when applied to insoluble pharmaceutical agents, such as camptothecin, that comprise an alcoholic hydroxyl group.

The invention claimed is:
1. A compound represented by formula (2) or formula (3), or a pharmaceutically acceptable salt, or a hydrate thereof,

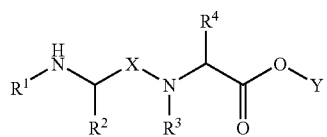

(2)

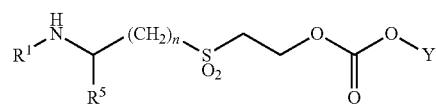

(3)

wherein,
$R^1$ represents a hydrogen atom or C1-C6 alkyl group;
X represents a C=O or C1-C3 alkylene group;
$R^2$ and $R^4$ each independently represents a hydrogen atom, C1-C6 alkyl group, or amino acid side chain; and
$R^3$ represents a C1-C6 alkyl group
Y is a group represented by formula (4):

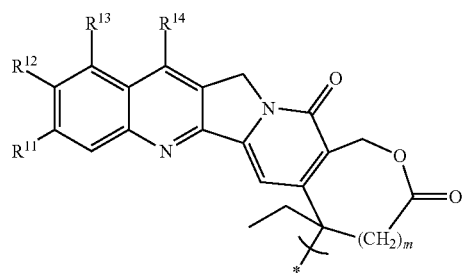

(4)

wherein,
* indicates a linkage site;
m is either 0 or 1;
$R^{11}$ represents a hydrogen atom, halogen atom, or C1-C6 alkyl group;
$R^{12}$ represents a hydrogen atom, halogen atom, C1-C6 alkyl group, or hydroxyl group;
$R^{13}$ represents a hydrogen atom, amino group, nitro group, or (dimethylamino)methyl group;
$R^{14}$ represents a hydrogen atom, C1-C6 alkyl group, (4-methylpiperazinyl)methyl group, or (tert-butoxyimino)methyl group;
$R^{13}$ and $R^{14}$, and $R^{11}$ and $R^{12}$, may, respectively, be linked to each other to form a 5- or 6-membered ring, wherein the skeleton of the 5- or 6-membered ring consists of carbon atoms or carbon atoms and 1 to 2 heteroatoms selected from N, S and O, and the 5- or 6-membered ring may be substituted by 1 to 3 substituents selected from Group A described below, wherein the substituents of Group A may be further substituted by 1 to 3 substituents selected from Group B described below:
Group A: a C1-C10 alkyl group, amino group, mono-C1-C8 alkylamino group, di-C1-C8 alkylamino group, C1-C8 alkoxy group, C1-C8 alkylthio group, and group represented by X= wherein X represents an oxygen atom or sulfur atom;
Group B: a C1-C6 alkoxy group, hydroxy group, halogen atom, amino group, mono-C1-C6 alkylamino group, di-C1-C6 alkylamino group, C3-C7 cycloalkyl group, heterocycle, and aryl ring which may comprise 1 to 3 substituents selected from the group consisting of a hydroxy group, C1-C6 alkoxy group, halogen atom, amino group, mono-C1-C6 alkylamino group, and di-C1-C6 alkylamino group;
n represents an integer from 1 to 6; and
$R^5$ represents a hydrogen atom or —COOR$^6$ wherein $R^6$ represents a hydrogen atom or C1-C6 alkyl group.
2. The compound of claim 1, or a pharmaceutically acceptable salt, or a hydrate thereof, wherein $R^1$ is a hydrogen atom, methyl group, or ethyl group.
3. The compound of claim 1, or a pharmaceutically acceptable salt, or a hydrate thereof, wherein $R^2$ is a hydrogen atom or methyl group.
4. The compound of claim 1, or a pharmaceutically acceptable salt, or a hydrate thereof, wherein $R^3$ is a C1-C3 alkyl group.
5. The compound of claim 1, or a pharmaceutically acceptable salt, or a hydrate thereof, wherein $R^4$ is a hydrogen or methyl group.
6. The compound of claim 1, or a pharmaceutically acceptable salt, or a hydrate thereof, wherein n is 1, and $R^5$ is a hydrogen atom or —COOR$^6$ wherein $R^6$ represents a hydrogen atom or C1-C6 alkyl group.
7. The compound of claim 1, or a pharmaceutically acceptable salt, or a hydrate thereof, wherein n is an integer from 2 to 6, and $R^5$ is a hydrogen atom.
8. The compound of claim 1 or a pharmaceutically acceptable salt, or a hydrate thereof, wherein Y is a group represented by formula (5):

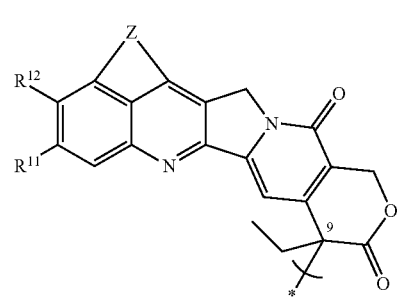

(5)

wherein,
* indicates a linkage site;
$R^{11}$ and $R^{12}$ are defined as in claim 1; and
Z represents —NH—C(=X)—N(R$^{21}$)— or —N=C(R$^{22}$)—N(R$^{21}$)—
wherein $R^{21}$ represents a hydrogen atom or a C1-C10 alkyl group that may be substituted by 1-3 substituents selected from Group B described below:
Group B: a C1-C6 alkoxy group, hydroxy group, halogen atom, amino group, mono-C1-C6 alkylamino group, di-C1-C6 alkylamino group, C3-C7 cycloalkyl group, heterocycle, and aryl ring which may be substituted by 1 to 3 substituents selected from the group consisting of a hydroxy group, C1-C6 alkoxy group, halogen atom, amino group, mono-C1-C6 alkylamino group, and di-C1-C6 alkylamino group;

R²² represents a hydrogen atom, amino group, or a C1-C6 alkyl group that may be substituted by 1 to 3 substituents selected from Group C described below, a C1-C6 alkoxy group that may be substituted by 1 to 3 substituents selected from Group C described below, a C1-C6 alkylthio group that may be substituted by 1 to 3 substituents selected from Group C described below, a mono-C1-C6 alkylamino group that may be substituted by 1 to 3 substituents selected from Group C described below, or a di-C1-C6 alkylamino group that may be substituted by 1 to 3 substituents selected from Group C described below:

Group C: a C1-C6 alkoxy group, hydroxy group, halogen atom, amino group, mono-C1-C3 alkylamino group, di-C1-C3 alkylamino group, C3-C7 cycloalkyl group, heterocycle, and aryl ring which may be substituted by 1 to 3 substituents selected from the group consisting of a hydroxy group, C1-C6 alkoxy group, halogen atom, amino group, mono-C1-C6 alkylamino group, and di-C1-C6 alkylamino group; and X represents an oxygen atom or sulfur atom.

9. The compound of claim 8, or a pharmaceutically acceptable salt, or a hydrate thereof, wherein Y is a group represented by formula (6):

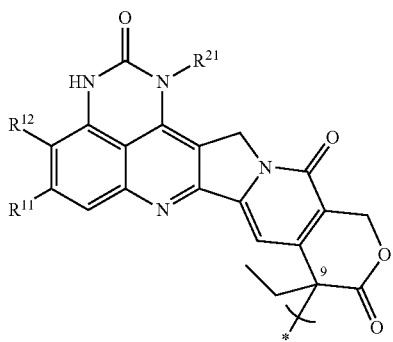

(6)

wherein * indicates a linkage site; and
R¹¹, R¹², and R²¹ are defined as in claim 8.

10. The compound of claim 9, or a pharmaceutically acceptable salt, or a hydrate thereof, wherein R¹¹ and R¹² are hydrogen atoms; and
R²¹ represents a hydrogen atom, or a C1-C8 alkyl group that may be substituted by a substituent selected from Group D described below:
Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring which may be substituted by 1 to 3 substituents selected from the group consisting of a hydroxy group, C1-C3 alkoxy group, and halogen atom.

11. The compound of claim 9, or a pharmaceutically acceptable salt, or a hydrate thereof, wherein Y is a residue of a compound Y—OH comprising at least one alcoholic hydroxyl group, wherein the compound is selected from the group consisting of:
a) (9S)-1-butyl-9-ethyl-9-hydroxy-1H,12H-pyrano [3",4":6',7']indolizino[1',2':6,5]pyrido[4,3,2-de]quinazoline-2,10,13(3H,9H,15H)-trione;

b) (9S)-9-ethyl-9-hydroxy-1-[2-(4-morpholino)ethyl]-1H,12H-pyrano [3",4":6',7']indolizino[1',2':6,5]pyrido[4,3,2-de]quinazoline-2,10,13(3H,9H,15H)-trione;

c) (9S)-1-[3-(dimethylamino)propyl]-9-ethyl-9-hydroxy-1H,12H-pyrano [3",4":6',7']indolizino[1',2':6,5]pyrido[4,3,2-de]quinazoline-2,10,13(3H,9H,15H)-trione;

d) (9S)-9-ethyl-9-hydroxy-1-phenethyl-1H,12H-pyrano [3",4":6',7']indolizino[1',2':6,5]pyrido[4,3,2-de]quinazoline-2,10,13(3H,9H,15H)-trione;

e) (9S)-9-ethyl-9-hydroxy-1-[2-(pyridin-2-yl)ethyl]-1H,12H-pyrano [3",4":6',7']indolizino[1',2':6,5]pyrido[4,3,2-de]quinazoline-2,10,13(3H,9H,15H)-trione;

f) (9S)-9-ethyl-1-heptyl-9-hydroxy-1H,12H-pyrano [3",4":6',7']indolizino[1',2':6,5]pyrido[4,3,2-de]quinazoline-2,10,13(3H,9H,15H)-trione;

g) (9S)-9-ethyl-9-hydroxy-1-propyl-1H,12H-pyrano [3",4":6',7']indolizino[1',2':6,5]pyrido[4,3,2-de]quinazoline-2,10,13(3H,9H,15H)-trione;

h) (9S)-9-ethyl-9-hydroxy-1-[2-(pyridin-3-yl)ethyl]-1H,12H-pyrano [3",4":6',7']indolizino[1',2':6,5]pyrido[4,3,2-de]quinazoline-2,10,13(3H,9H,15H)-trione;

i) (9S)-9-ethyl-9-hydroxy-1-(3-phenylpropyl)-1H,12H-pyrano[3",4":6',7']indolizino[1',2':6,5]pyrido[4,3,2-de]quinazoline-2,10,13(3H,9H,15H)-trione;

j) (9S)-9-ethyl-9-hydroxy-1-(2-methylpropyl)-1H,12H-pyrano[3",4":6',7']indolizino[1',2':6,5]pyrido[4,3,2-de]quinazoline-2,10,13(3H,9H,15H)-trione;

k) (9S)-9-ethyl-1-hexyl-9-hydroxy-1H,12H-pyrano[3",4":6',7']indolizino[1',2':6,5]pyrido[4,3,2-de]quinazoline-2,10,13(3H,9H,15H)-trione;

l) (9S)-9-ethyl-9-hydroxy-1-pentyl-1H,12H-pyrano[3",4":6',7']indolizino[1',2':6,5]pyrido[4,3,2-de]quinazoline-2,10,13(3H,9H,15H)-trione;

m) (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-2,10,13(3H,9H,15H)-trione;

n) (9S)-1-benzyl-9-ethyl-9-hydroxy-1H,12H-pyrano[3",4":6',7']indolizino[1',2':6,5]pyrido[4,3,2-de]quinazoline-2,10,13(3H,9H,15H)-trione;

o) (9S)-9-ethyl-9-hydroxy-1-(3-methylbutyl)-1H,12H-pyrano[3",4":6',7']indolizino[1',2':6,5]pyrido[4,3,2-de]quinazoline-2,10,13(3H,9H,15H)-trione;

p) (9S)-1,9-diethyl-9-hydroxy-1H,12H-pyrano[3",4":6',7']indolizino[1',2':6,5]pyrido[4,3,2-de]quinazoline-2,10,13(3H,9H,15H)-trione;

q) (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-2,10,13(3H,9H,15H)-trione;

r) (9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-2,10,13(3H,9H,15H)-trione;

s) (9S)-9-ethyl-9-hydroxy-1-(1-methylethyl)-1H,12H-pyrano[3",4":6',7']indolizino[1',2':6,5]pyrido[4,3,2-de]quinazoline-2,10,13(3H,9H,15H)-trione; and t) (9S)-1-(3,3-dimethylbutyl)-9-ethyl-9-hydroxy-1H,12H-pyrano[3",4":6',7']indolizino[1',2':6,5]pyrido[4,3,2-de]quinazoline-2,10,13(3H,9H,15H)-trione.

12. The compound of claim 8, or a pharmaceutically acceptable salt, or a hydrate thereof, wherein Y is a group represented by formula (7):

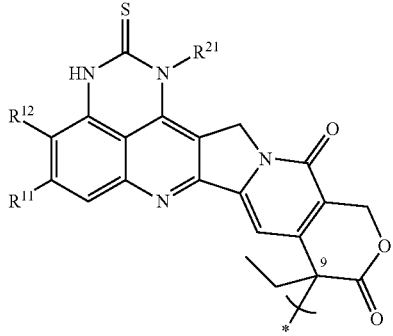

(7)

wherein,
* indicates a linkage site; and
$R^{11}$, $R^{12}$, and $R^{21}$ are defined as in claim 8.

13. The compound of claim 12, or a pharmaceutically acceptable salt, or a hydrate thereof, wherein $R^{11}$ and $R^{12}$ are hydrogen atoms; and
$R^{21}$ is a hydrogen atom, or a C1-C8 alkyl group that may be substituted by a substituent selected from Group D described below:
Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring which may be substituted by 1 to 3 substituents selected from the group consisting of a hydroxy group, C1-C3 alkoxy group, and halogen atom.

14. The compound of claim 12, or a pharmaceutically acceptable salt, or a hydrate thereof, wherein Y is a residue of a compound Y—OH comprising at least one alcoholic hydroxyl group, wherein the compound is selected from the group consisting of:
 a) (9S)-9-ethyl-9-hydroxy-1-(3-methylbutyl)-1H,12H-pyrano[3",4":6',7']indolizino[1',2':6,5]pyrido[4,3,2-de]quinazoline-2(3H)-thione-10,13(9H,15H)-dione;
 b) (9S)-9-ethyl-9-hydroxy-1-phenethyl-1H,12H-pyrano[3",4":6',7']indolizino[1',2':6,5]pyrido[4,3,2-de]quinazoline-2(3H)-thione-10,13(9H,15H)-dione; and
 c) (9S)-9-ethyl-9-hydroxy-1-pentyl-1H,12H-pyrano[3",4":6',7']indolizino[1',2':6,5]pyrido[4,3,2-de]quinazoline-2(3H)-thione-10,13(9H,15H)-dione.

15. The compound of claim 8, or a pharmaceutically acceptable salt, or a hydrate thereof, wherein Y is a group represented by formula (8):

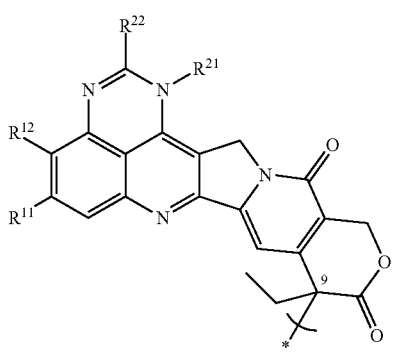

(8)

wherein,
* indicates a linkage site; and
$R^{11}$, $R^{12}$, $R^{21}$, and $R^{22}$ are defined as in claim 8.

16. The compound of claim 15, or a pharmaceutically acceptable salt, or a hydrate thereof, wherein $R^{11}$ is a hydrogen atom;
$R^{12}$ is a hydrogen atom or C1-C3 alkyl group;
$R^{21}$ is a hydrogen atom, or a C1-C8 alkyl group that may be substituted by 1 to 3 substituents selected from Group D described below; and
$R^{22}$ is a hydrogen atom, amino group, or a C1-C6 alkyl group that may be substituted by 1 to 3 substituents selected from Group D described below, a C1-C6 alkoxy group that may be substituted by 1 to 3 substituents selected from Group D described below, a C1-C6 alkylthio group that may be substituted by 1 to 3 substituents selected from Group D described below, a mono-C1-C6 alkylamino group that may be substituted by 1 to 3 substituents selected from Group D described below, or a di-C1-C6 alkylamino group that may be substituted by 1 to 3 substituents selected from Group D described below:
Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring which may be substituted by 1 to 3 substituents selected from the group consisting of a hydroxy group, C1-C3 alkoxy group, and halogen atom.

17. The compound of claim 15, or a pharmaceutically acceptable salt, or a hydrate thereof, wherein Y is a residue of a compound Y—OH comprising at least one alcoholic hydroxyl group, wherein the compound is selected from the group consisting of:
 a) (9S)-1-butyl-9-ethyl-9-hydroxy-1H,12H-pyrano[3",4":6',7']indolizino[1',2':6,5]pyrido[4,3,2-de]quinazoline-10,13(9H,15H)-dione;
 b) (9S)-9-ethyl-9-hydroxy-1-[2-(4-morpholino)ethyl]-1H,12H-pyrano[3",4":6',7']indolizino[1',2':6,5]pyrido[4,3,2-de]quinazoline-10,13(9H,15H)-dione;
 c) (9S)-9-ethyl-9-hydroxy-1-propyl-1H,12H-pyrano[3",4":6',7']indolizino[1',2':6,5]pyrido[4,3,2-de]quinazoline-10,13(9H,15H)-dione;
 d) (9S)-1-benzyl-9-ethyl-9-hydroxy-1H,12H-pyrano[3",4":6',7']indolizino[1',2':6,5]pyrido[4,3,2-de]quinazoline-10,13(9H,15H)-dione;
 e) (9S)-9-ethyl-9-hydroxy-1-phenethyl-1H,12H-pyrano[3",4":6',7']indolizino[1',2':6,5]pyrido[4,3,2-de]quinazoline-10,13(9H,15H)-dione;
 f) (9S)-2,9-diethyl-9-hydroxy-1-phenethyl-1H,12H-pyrano[3",4":6',7']indolizino[1',2':6,5]pyrido[4,3,2-de]quinazoline-10,13(9H,15H)-dione;
 g) (9S)-9-ethyl-9-hydroxy-1-(3-phenylpropyl)-1H,12H-pyrano[3",4":6',7']indolizino[1',2':6,5]pyrido[4,3,2-de]quinazoline-10,13(9H,15H)-dione;
 h) (9S)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;
 i) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;
 j) (9S)-2,9-diethyl-9-hydroxy-1-(2-methylpropyl)-1H,12H-pyrano[3",4":6',7']indolizino[1',2':6,5]pyrido[4,3,2-de]quinazoline-10,13(9H,15H)-dione;
 k) (9S)-9-ethyl-1-heptyl-9-hydroxy-1H,12H-pyrano[3",4":6',7']indolizino[1',2':6,5]pyrido[4,3,2-de]quinazoline-10,13(9H,15H)-dione;

l) (9S)-9-ethyl-9-hydroxy-1-methyl-1H,12H-pyrano[3",4":6',7']indolizino[1',2':6,5]pyrido[4,3,2-de]quinazoline-10,13(9H,15H)-dione;

m) (9S)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione;

n) (9S)-9-ethyl-1-hexyl-9-hydroxy-1H,12H-pyrano[3",4":6',7']indolizino[1',2':6,5]pyrido[4,3,2-de]quinazoline-10,13(9H,15H)-dione;

o) (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione;

p) (9S)-1,9-diethyl-9-hydroxy-1H,12H-pyrano[3",4":6',7']indolizino[1',2':6,5]pyrido[4,3,2-de]quinazoline-10,13(9H,15H)-dione;

q) (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-10,13(9H,15H)-dione;

r) (9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-10,13(9H,15H)-dione;

s) (9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-10,13H-(9H,15H)-dione;

t) (9S)-9-ethyl-1-[2-(4-fluorophenyl)ethyl]-9-hydroxy-2-methyl-1H,12H-pyrano[3",4":6',7']indolizino[1',2':6,5]pyrido[4,3,2-de]quinazoline-10,13(9H,15H)-dione;

u) (9S)-9-ethyl-9-hydroxy-1-(1-methylethyl)-1H,12H-pyrano[3",4":6',7']indolizino[1',2':6,5]pyrido[4,3,2-de]quinazoline-10,13(9H,15H)-dione;

v) (9S)-1-(3,3-dimethylbutyl)-9-ethyl-9-hydroxy-1H,12H-pyrano[3",4":6',7']indolizino[1',2':6,5]pyrido[4,3,2-de]quinazoline-10,13(9H,15H)-dione;

w) (9S)-9-ethyl-9-hydroxy-2-methoxy-1-(3-methylbutyl)-1H,12H-pyrano[3",4":6',7']indolizino[1',2':6,5]pyrido[4,3,2-de]quinazoline-10,13(9H,15H)-dione;

x) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

y) (9RS)-9-ethyl-9-hydroxy-4-methyl-1-pentyl-1H,12H-pyrano[3",4":6',7']indolizino[1',2':6,5]pyrido[4,3,2-de]quinazoline-10,13(9H,15H)-dione;

z) (9S)-9-ethyl-9-hydroxy-1-(2-hydroxyethyl)-1H,12H-pyrano[3",4":6',7']indolizino[1',2':6,5]pyrido[4,3,2-de]quinazoline-10,13(9H,15H)-dione;

aa) (9S)-9-ethyl-9-hydroxy-1-(2-hydroxyethyl)-2-methyl-1H,12H-pyrano[3",4":6',7']indolizino[1',2':6,5]pyrido[4,3,2-de]quinazoline-10,13(9H,15H)-dione;

bb) (9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15)-dione;

cc) (9S)-2,9-diethyl-9-hydroxy-1-pentyl-1H,12H-pyrano[3",4":6',7']indolizino[1',2':6,5]pyrido[4,3,2-de]quinazoline-10,13(9H,15H)-dione;

dd) (9S)-9-ethyl-9-hydroxy-1-pentyl-2-propyl-1H,12H-pyrano[3",4":6',7']indolizino[1',2':6,5]pyrido[4,3,2-de]quinazoline-10,13(9H,15H)-dione;

ee) (9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione;

ff) (9S)-9-ethyl-9-hydroxy-2-hydroxymethyl-1-(2-methylpropyl)-1H,12H-pyrano[3",4":6',7']indolizino[1',2':6,5]pyrido[4,3,2-de]quinazoline-10,13(9H,15H)-dione;

gg) (9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione;

hh) (9S)-2-chloromethyl-9-ethyl-9-hydroxy-1-(3-methylbutyl)-1H,12H-pyrano[3",4":6',7']indolizino[1',2':6,5]pyrido[4,3,2-de]quinazoline-10,13(9H,15)-dione;

ii) (9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H,15H)-dione;

jj) (9S)-9-ethyl-9-hydroxy-1-pentyl-2-trifluoromethyl-1H,12H-pyrano[3",4":6',7']indolizino[1',2':6,5]pyrido[4,3,2-de]quinazoline-10,13(9H,15H)-dione;

kk) (9S)-9-ethyl-9-hydroxy-1-(3-methylbutyl)-2-methylthio-1H,12H-pyrano[3",4":6',7']indolizino[1',2':6,5]pyrido[4,3,2-de]quinazoline-10,13(9H,15H)-dione;

ll) (9S)-9-ethyl-2-ethylthio-9-hydroxy-1-(3-methylbutyl)-1H,12H-pyrano[3",4":6',7']indolizino[1',2':6,5]pyrido[4,3,2-de]quinazoline-10,13(9H,15H)-dione;

mm) (9S)-2-(dimethylamino)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione; and nn) (9S)-2-(butylamino)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione.

18. The compound of claim 1 represented by formula (2) or formula (3), or a pharmaceutically acceptable salt, or a hydrate thereof, comprising at least one compound selected from the group consisting of:

(a) (9S)-9-ethyl-9-{[methyl-(2-methylamino-ethyl)-amino]-acetoxy}-1-pentyl-1H,12H-pyrano[3",4":6',7']indolizino[1',2':6,5]pyrido[4,3,2-de]quinazoline-10,13(9H,15H)-dione;

(b) (9S)-9-ethyl-9-(glycyl-sarcosyloxy)-1-pentyl-1H,12H-pyrano[3",4":6',7']indolizino[1',2':6,5]pyrido[4,3,2-de]quinazoline-10,13(9H,15H)-dione;

(c) (9S)-9-{[(2-amino-ethyl)-methyl-amino]-acetoxy}-9-ethyl-1-pentyl-1H,12H-pyrano[3",4":6',7']indolizino[1',2':6,5]pyrido[4,3,2-de]quinazoline-10,13(9H,15H)-dione;

(d) (9S)-9-ethyl-9-(sarcosyl-sarcosyloxy)-1-pentyl-1H,12H-pyrano[3",4":6',7']indolizino[1',2':6,5]pyrido[4,3,2-de]quinazoline-10,13(9H,15H)-dione;

(e) (9S)-9-[2-(2-aminoethanesulfonyl)ethoxycarbonyloxy]-9-ethyl-1-pentyl-1H,12H-pyrano[3",4":6',7']indolizino[1',2':6,5]pyrido[4,3,2-de]quinazoline-10,13(9H,15H)-dione;

(f) (aminoacetyl-methyl-amino)-acetic acid (S)-4-ethyl-3,13-dioxo-3,4,12,13-tetrahydro-1H-2-oxa-6,12a-diaza-dibenzo[b,h]fluoren-4-yl ester;

(g) (9S)-9-{2-[(R-2-amino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione;

(h) (9S)-9-{2-[(R-2-amino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2de]quinazoline-10,13(9H,15H)-dione;

(i) (9S)-9-ethyl-9-(N-methylalanyl-N-methylalanyloxy)-1-pentyl-1H,12H-pyrano[3",4":6',7']indolizino[1',2':6,5]pyrido[4,3,2-de]quinazoline-10,13(9H,15H)-dione; and (j) (9S)-9-ethyl-9-(sarcosyl-N-methylalanyloxy)-1-pentyl-1H,12H-pyrano[3",4":6',7']indolizino[1',2':6,5]pyrido[4,3,2-de]quinazoline-10,13(9H,15H)-dione.

19. A pharmaceutical composition comprising the compound of claim 1, or a pharmaceutically acceptable salt, or a hydrate thereof, as an effective ingredient.

20. A method of producing a compound represented by formula (2);

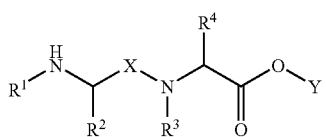
(2)

wherein,

X represents a C=O or C1-C3 alkylene group;

$R^1$ represents a hydrogen atom, or C1-C6 alkyl group;

$R^2$ and $R^4$ each independently represents a hydrogen atom, C1-6 alkyl group, or amino acid side chain; and $R^3$ represents a C1-C6 alkyl group;

Y is a group represented by formula (4):

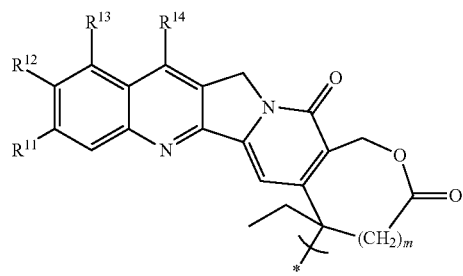
(4)

wherein,

* indicates a linkage site;

m is either 0 or 1;

$R^{11}$ represents a hydrogen atom, halogen atom, or C1-C6 alkyl group;

$R^{12}$ represents a hydrogen atom, halogen atom, C1-C6 alkyl group, or hydroxyl group;

$R^{13}$ represents a hydrogen atom, amino group, nitro group, or (dimethylamino)methyl group;

$R^{14}$ represents a hydrogen atom, C1-C6 alkyl group, (4-methylpiperazinyl)methyl group, or (tert-butoxyimino)methyl group;

$R^{13}$ and $R^{14}$, and $R^{11}$ and $R^{12}$, may, respectively, be linked to each other to form a 5- or 6-membered ring, wherein the skeleton of the 5- or 6-membered ring consists of carbon atoms or carbon atoms and 1 to 2 heteroatoms selected from N, S and O, and the 5- or 6-membered ring may be substituted by 1 to 3 substituents selected from Group A described below, wherein the substituents of Group A may be further substituted by 1 to 3 substituents selected from Group B described below:

Group A: a C1-C10 alkyl group, amino group, mono-C1-C8 alkylamino group, di-C1-C8 alkylamino group, C1-C8 alkoxy group, C1-C8 alkylthio group, and group represented by X= wherein X represents an oxygen atom or sulfur atom;

Group B: a C1-C6 alkoxy group, hydroxy group, halogen atom, amino group, mono-C1-C6 alkylamino group, di-C1-C6 alkylamino group, C3-C7 cycloalkyl group, heterocycle, and aryl ring which may comprise 1 to 3 substituents selected from the group consisting of a hydroxy group, C1-C6 alkoxy group, halogen atom, amino group, mono-C1-C6 alkylamino group, and di-C1-C6 alkylamino group wherein the method comprises the step of:

reacting a compound represented by formula (9)

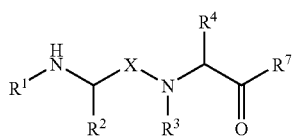
(9)

wherein, X, $R^1$, $R^2$, $R^3$, and $R^4$ are defined as in formula (2);

$R^7$ represents a halogen atom or group represented by $OR^8$ wherein $R^8$ represents a hydrogen atom or C1-C6 alkyl group; and the nitrogen atom binding to $R^1$ may be protected by a protecting group with a compound represented by Y—OH which includes an alcoholic hydroxyl group to obtain the compound represented by formula (2).

* * * * *

UNITED STATES PATENT AND TRADEMARK OFFICE
CERTIFICATE OF CORRECTION

| | | |
|---|---|---|
| PATENT NO. | : 7,910,593 B2 | Page 1 of 1 |
| APPLICATION NO. | : 11/547036 | |
| DATED | : March 22, 2011 | |
| INVENTOR(S) | : Isao Umeda, Jun Ohwada and Sawako Ozawa | |

It is certified that error appears in the above-identified patent and that said Letters Patent is hereby corrected as shown below:

Col. 34, line 60, "Removal of the amino group" should be --Removal of the amino protecting group--.

Signed and Sealed this
Twenty-eighth Day of June, 2011

David J. Kappos
*Director of the United States Patent and Trademark Office*